(12) United States Patent
Keller et al.

(10) Patent No.: US 8,871,494 B2
(45) Date of Patent: Oct. 28, 2014

(54) OVER-PRODUCTION OF SECONDARY METABOLITES BY OVER-EXPRESSION OF THE VEA GENE

(75) Inventors: Nancy P. Keller, Madison, WI (US); Saori Amaike, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 654 days.

(21) Appl. No.: 12/799,505

(22) Filed: Apr. 26, 2010

(65) Prior Publication Data
US 2011/0076682 A1    Mar. 31, 2011

Related U.S. Application Data

(60) Provisional application No. 61/172,514, filed on Apr. 24, 2009.

(51) Int. Cl.
*C12N 1/00* (2006.01)
*C12Q 1/68* (2006.01)

(52) U.S. Cl.
CPC ........ *C12Q 1/6895* (2013.01); *C12Q 2600/158* (2013.01)
USPC ..................... 435/254.3; 435/243; 435/254.11

(58) Field of Classification Search
None
See application file for complete search history.

(56) References Cited

U.S. PATENT DOCUMENTS

| | | | |
|---|---|---|---|
| 4,469,863 | A | 9/1984 | Ts'o et al. |
| 4,683,195 | A | 7/1987 | Mullis et al. |
| 5,034,506 | A | 7/1991 | Summerton et al. |
| 5,216,141 | A | 6/1993 | Benner |
| 5,235,033 | A | 8/1993 | Summerton et al. |
| 5,386,023 | A | 1/1995 | Sanghvi et al. |
| 5,602,240 | A | 2/1997 | De Mesmaeker et al. |
| 5,637,684 | A | 6/1997 | Cook et al. |
| 5,644,048 | A | 7/1997 | Yau |
| 5,952,174 | A | 9/1999 | Nikiforov et al. |

OTHER PUBLICATIONS

Dreyer et al., Applied and Environmental Microbiology, 2007; 73(10): 3412-22.*
Bowie et al (Science, 1990, 257:1306-1310).*
Adams, et al., Microbiol. Mol. Biol. Rev. 62:35-54 (1998).
Bayram, et al., Fungal Genet. Biol. 45:127-138 (2008).
Bayram, et al., Science 320:1504-1506 (2008).
Brakhage, FEMS Microbiol. Lett. 148:1-10 (1997).
Bok, et al., Eukaryotic Cell 3:527-535 (2004).
Bok, et al., Eukaryotic Cell 4:1574-1582 (2005).
Bok, et al., Mol. Microbiol. 61:1636-1645 (2006).
Brodhagen, et al., Mol. Microbiol. 67:378-391 (2008).
Busch, et al., Mol. Microbiol. 49:717-730 (2003).
Busch, et al., Proc. Natl. Acad. Sci USA 104:8089-8094 (2007).
Calvo, et al., Microbiol. Mol. Biol. Rev. 66:447-459 (2002).
Calvo, et al., Appl. Environ. Microbiol. 65:3668-3673 (1999).
Calvo, et al., Appl. Environ. Microbiol. 70:4733-4739 (2004).
Chaveroche, et al., Nucleic Acids Res. 28:e97 (2000).
Cho, et al., The Journal of Microbiology 41:46-51 (2003).
Champe, et al., J. Gen. Microbiol. 133:1383-1387 (1987).
Chen, et al., Proc. Natl. Acad. Sci. USA 101:5048-5052 (2004).
Chen, et al., Genes Dev. 20:1150-1161 (2006).
Cseke, et al., Handbook of Molecular and Cellular Methods in Biology and Medicine, 2nd ed., CRC Press, Boca Raton, FL (2004), Index only.
Dagenais, et al., Infect. Immun. 76:3214-3220 (2008).
Diener, et al., Ann. Rev. Phytopathol. 25:249-270 (1987).
Dreyer, et al., Appl. Environ. Microbiol. 73:3412-3422 (2007).
Duran, et al., Appl. Microbiol. Biotechnol. 73:1158-1168 (2007).
Duran, et al., Open Mycol. J. 3:27-36 (2009).
Eng, et al., J. Am. Soc. Mass. Spectrom 5:976-989 (1994).
Etxebeste, et al., Eukaryotic Cell 7(1):38-48 (2008).
Feinberg, et al., Anal. Biochem. 132:6-13 (1983).
Fernandez-Abalos, et al., Mol. Microbiol. 27(1):121-130 (1998).
Fray, Ann. Bot. 89:245-253 (2002).
Georgianna, et al., Fungal Genet. Biol. 46:113-125 (2009).
Ausubel, et al. (ed.), Current Protocols in Molecular Biology, Contents, vols. 1-5, John Wiley & Sons, Inc. (2007), Index only.
Gyuris, et al., Cell 75:791-803 (1993).
Greenspan, et al., J. Cell Biol. 100:965-973 (1985).
Hanahan, et al., Methods Enzymol. 204:63-113 (1991).
Hicks, et al., The Mycota XI, Kempken (Ed.), Springer-Verlag Berlin Heidelberg, pp. 55-69 (2002).
Hu, et al., Mol. Cell 9:789-798 (2002).
Hornby, et al., Appl. Environ. Microbiol. 67:2982-2992 (2001).
Brown, et al., Appl. Environ. Microbiol. 74:5674-5685 (2008).
Jensen, et al., Appl. Environ. Microbiol. 58:2505-2508 (1992).
Kale, et al., Fungal Genet. Biol. 45:1422-1429 (2008).
Kato, et al., Eukaryotic Cell 2:1178-1186 (2003).
Kim, et al., Fungal Genet. Biol. 37:72-80 (2002).
Klich, Mol. Plant Pathol. 8:713-722 (2007).
Keller, et al., Nat. Rev. Microbiol. 3:937-947 (2005).
Keller, et al., Appl. Environ. Microbiol. 60:1444-1450 (1994).
Kolar, et al., Gene 62:127-134 (1998).
Krappmann, et al., Eukaryotic Cell 4:1298-1307 (2005).
Krappmann, et al., Mol. Microbiol. 61(1):76-88 (2006).

(Continued)

*Primary Examiner* — Gary Nickol
*Assistant Examiner* — Lakia Tongue
(74) *Attorney, Agent, or Firm* — Quarles & Brady, LLP

(57) ABSTRACT

The invention provides a general and facile method to obtain secondary metabolites from fungal sources. The invention is based on the discovery that the fungal gene veA and protein encoded thereby regulates the activity of multiple secondary metabolite gene clusters in fungi. Over expression of the gene veA provides increased production of secondary metabolites in engineered cells. In particular, such a method of increasing secondary metabolite production allows the production of improved yields of valuable secondary metabolite products.

2 Claims, 23 Drawing Sheets
(13 of 23 Drawing Sheet(s) Filed in Color)

(56) References Cited

OTHER PUBLICATIONS

Kunkel, Proc. Natl. Acad. Sci. USA 82:488-492 (1985).
Li, et al., Mol. Microbiol. 62(5):1418-1432 (2006).
Link, et al., Nat. Biotechnol. 17:676-682 (1999).
Lillie, et al., Histopathologic Technic and Practical Histochemistry, 4th ed., McGraw-Hill Book Company, New York, NY (1976), contents/index only.
Maggio-Hall, et al., Mol. Microbiol. 54:1173-1185 (2004).
Maggio-Hall, et al., Mol. Plant-Microbe Interact. 18:783-793 (2005).
Michailides, et al., Plant Pathol. 56:352 (2007).
Miller, et al., Mol. Cell. Biol. 5:1714-1721 (1985).
Mooney, et al., Genes Dev. 4:1473-1482 (1990).
Muyrers, et al., Genet. Eng. 22:77-98 (2000).
Muture, et al., East Afr. Med. J. 82:275-279 (2005).
Nayak, et al., Genetics 172:1557-1566 (2006).
Ni, et al., PLoS One 2(10):e970 (2007).
Perrin, et al., PLoS Pathog. 3(4):e50 (2007).
Puig, et al., Methods 24:218-229 (2001).
Punt, et al., Methods Enzymol 216:447-457 (1992).
Purschwitz, et al., Curr. Biol. 18:255-259 (2008).
Pettit, Yellow Mold and Aflatoxin, p. 35-36, in D. M. Porter, D. H. Smith, and R. Rodriguez-Kabana (ed.) Compendium of Peanut Diseases. The American Phytopathological Society, St. Paul, MN (1984).
Robens, et al., The Costs of Mycotoxin Management in the United States, p. 1-13. In H. K. Abbas (ed.) Aflatoxin and Food Safety. CRC Press, Boca Raton, FL (2005).
Rohila, et al., Plant J. 38:172-181 (2004).
Saiki, et al., Nature 324:163-166 (1986).
Sambrook, et al., Molecular Cloning: A Laboratory Manual, Second Edition, Cold Spring Harbor Laboratory Press, NY (1989), Index only.
Seiler, et al., Mol. Biol. Cell 17:4080-4092 (2006).
Shevchenko, et al., Anal. Chem 68, 850-858 (1996).
Shwab, et al., Eukaryotic Cell 6:1656-1664 (2007).
Southern, J. Mol. Biol. 98:503-517 (1975).
Sprote, et al., Arch. Microbiol. 188:69-79 (2007).
Stinnett, et al., Mol. Microbiol. 63(1):242-255 (2007).
Shchepin, et al., Chem. Biol. 10:743-750 (2003).
Shimizu, K., et al., Genetics 157:591-600 (2001).
Smart, et al., Phytopathology 80:1287-1294 (1990).
Szewczyk, et al., Nat. Protoc. 1:3111-3120 (2006).
Thompson, et al., Nucleic Acids Res 22:4673-4680 (1994).
Tsitsigiannis, et al., Mol. Microbiol. 59:882-892 (2006).
Tsitsigiannis, et al., Microbiology 151:1809-1821 (2005).
Tsitsigiannis, et al., J. Biol. Chem. 279:11344-11353 (2004).
Williams, Microbiology 153:3923-3938 (2007).
Wilson, et al., Microbiology 150:2881-2888 (2004).
Woloshuk, et al., Appl. Environ. Microbiol. 60:2408-2414 (1994).
Yu, et al., Fungal Genet. Biol. 41:973-981 (2004).
Yu, et al., Rev. Iberoam. Micol. 22:194-202 (2005).
Yu, et al., Mycotoxin Production and Prevention of Aflatoxin Contamination in Food and Feed. In G. H. Goldman and S. A. Osmani (ed.), The Aspergilli. CRC Press, Boca Raton, FL (2008), pp. 457-472.

* cited by examiner

SEQ ID NO: 116 - VeA protein [*Aspergillus nidulans*]
GENBANK REF: AAD42946.

| | |
|---|---|
| matlaapppp lgesgnsnsv sritregkki tyklnimqqp kraracgqgs kshtdrrpvd | 61 |
| pppvielnif esdphddsnk tditfvynan fflfatlepe rpiatgklmt nqgspvltgv | 121 |
| pvagvayldk pnragyfifp dlsvrnegsy rfsfhlfeqi kdpkdategt qpmpspvpgk | 181 |
| lsspqeflef rlevisnpfi vysakkfpgl ttstpisrmi aeqgcrvrir rdvrmrrrgd | 241 |
| krtedydydn ergynnrrpd qyagsdayan aperprstsi stnmdpysyp srrpsaveyg | 301 |
| qpiaqpyqrp mastpapsst pipapipmpg pvalppstps pasahapapp svplaapppl | 361 |
| htpsyqshls fgatqtqypa pqlshipqqt ttpthpyspr ssishsrnqs iseyepsmgy | 421 |
| pgsqtrlsae rpsygqpsqt tslpplrhsl epsvnsrskt psnmitslpp iqslselpst | 481 |
| tsqpssaigs spanepgprl wetnsmlskr tyeesfghdd rplyngmrpd sesypggmqr | 541 |
| rpsyerssil dgpdqmaykr angrmvskpa tmr | |

FIG. 12

```
                        SEQUENCE LISTING

<160> NUMBER OF SEQ ID NOS: 146

<210> SEQ ID NO 1
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 1
tttggccatg ggtggtagcg gtggtatggt gagcaagggc gaggagctg                    49

<210> SEQ ID NO 2
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 2
aaaatttaag cttctacttg tacagttcgt ccatgccgtg                              40

<210> SEQ ID NO 3
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 3
actcacgaat ccacgggata cat                                                23

<210> SEQ ID NO 4
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 4
ggcctgagtg gccgggtggg atacggtcca tcgaaa                                  36

<210> SEQ ID NO 5
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 5
ggccatctag gccgaccgta tattgtttca taaatcctt                               39

<210> SEQ ID NO 6
<211> LENGTH: 24
<212> TYPE: DNA
<213> ORGANISM: Artificial Sequence
<220> FEATURE:
<223> OTHER INFORMATION: Synthetic oligonucleotide
```

```
<400> SEQUENCE: 6
tatgaccgcg tgagcaaata ggac                                      24

<210> SEQ ID NO 7
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 7
atgtttgaga tgggcccggt ggg                                       23

<210> SEQ ID NO 8
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 8
ttatcttaat ggtttcctag cctggt                                    26

<210> SEQ ID NO 9
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 9
atgtacgctg ttgaggatag ggc                                       23

<210> SEQ ID NO 10
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 10
ttagtattcg ttatccagac catcg                                     25

<210> SEQ ID NO 11
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 11
ctcgagttag tattcgttat ccagaccatc g                              31

<210> SEQ ID NO 12
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 12
ccatggatgg ctacacttgc agcaccacca                                30

<210> SEQ ID NO 13
<211> LENGTH: 32
```

-continued

<210> SEQ ID NO 13
<211> LENGTH: 32 (implied)
<212> TYPE: DNA
<213> ORGANISM: Artificial Sequence
<220> FEATURE:
<223> OTHER INFORMATION: Synthetic oligonucleotide

<400> SEQUENCE: 13
ctcgagttaa cgcatggtgg caggctttga ga                            32

<210> SEQ ID NO 14
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 14
atggtgagca agggcgagga g                                        21

<210> SEQ ID NO 15
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 15
ggtggtggtg ctgcaagtgt agccatcgtg gcgatggagc gcatgatata g       51

<210> SEQ ID NO 16
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 16
atggccgaca agcagaagaa c                                        21

<210> SEQ ID NO 17
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 17
acgagttccc accgggccca tctcaaacat gtggttcatg accttctgtt tcag    54

<210> SEQ ID NO 18
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 18
ggaatgcgcc ctatcctcaa cagcgtacat gtggttcatg accttctgtt tcag    54

<210> SEQ ID NO 19
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 19

```
gaattcatgc agcagcccaa gcgcgcgaga g                                    31
```

<210> SEQ ID NO 20
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 20

```
aaagggcccc gagaatgtcc gcctgacccg tgc                                  33
```

<210> SEQ ID NO 21
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 21

```
ccaagtctgc ccgacaagct cactg                                           25
```

<210> SEQ ID NO 22
<211> LENGTH: 66
<212> TYPE: DNA
<213> ORGANISM: Artificial Sequence
<220> FEATURE:
<223> OTHER INFORMATION: Synthetic oligonucleotide

<400> SEQUENCE: 22

```
cgccacagcg acgaggacga tggtctggat aacgaatacg gtggtagcgg tggtatggtg     60
agcaag                                                                66
```

<210> SEQ ID NO 23
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 23

```
gtattcgtta tccagaccat cgtc                                            24
```

<210> SEQ ID NO 24
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 24

```
ctgcacatat accaggctag gaaaccatta agaggtggta gcggtggtat ggtgagc        57
```

<210> SEQ ID NO 25
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 25

```
tcttaatggt ttcctagcct ggta                                            24
```

<210> SEQ ID NO 26
<211> LENGTH: 26

```
<212> TYPE: DNA
<213> ORGANISM: Artificial Sequence
<220> FEATURE:
<223> OTHER INFORMATION: Synthetic oligonucleotide

<400> SEQUENCE: 26
cctcgccctc ctgcatcaat attcgg                                          26

<210> SEQ ID NO 27
<211> LENGTH: 78
<212> TYPE: DNA
<213> ORGANISM: Artificial Sequence
<220> FEATURE:
<223> OTHER INFORMATION: Synthetic oligonucleotide

<400> SEQUENCE: 27
gagacggcta tgaaattctt tttccatctt ctcttaccac cgctaccacc tcttaatggt     60
ttcctagcct ggtatatg                                                   78

<210> SEQ ID NO 28
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 28
gagcaggcgc tctacatgag catgccctgc ccctgagagc aaaaggcgac cacatccagg     60

<210> SEQ ID NO 29
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 29
tcgtcaaccg cctcagctgg aacc                                            24

<210> SEQ ID NO 30
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 30
cctcctcgcc gcctctagta ccgtc                                           25

<210> SEQ ID NO 31
<211> LENGTH: 64
<212> TYPE: DNA
<213> ORGANISM: Artificial Sequence
<220> FEATURE:
<223> OTHER INFORMATION: Synthetic oligonucleotide

<400> SEQUENCE: 31
gaaattcttt ttccatcttc tcttaccacc gctaccaccg tattcgttat ccagaccatc     60
gtcc                                                                  64

<210> SEQ ID NO 32
<211> LENGTH: 62
<212> TYPE: DNA
<213> ORGANISM: Artificial Sequence
<220> FEATURE:
```

<223> OTHER INFORMATION: Synthetic oligonucleotide

<400> SEQUENCE: 32
cgagcaggcg ctctacatga gcatgccctg cccctgaaga ccgtatattg tttcataaat        60
cc        62

<210> SEQ ID NO 33
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 33
cggctgttta cattgtgttt tctgg        25

<210> SEQ ID NO 34
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 34
ccgtgaagaa cttggcgttg tag        23

<210> SEQ ID NO 35
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 35
ggaccgtcta attcaactca cag        23

<210> SEQ ID NO 36
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 36
cttccagcgg ttatcctccg ttg        23

<210> SEQ ID NO 37
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 37
atctgacaga gcggccgcaa ttgattacg        29

<210> SEQ ID NO 38
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 38
atatatgcgg ccgctcttgc atctttgttt        30

<210> SEQ ID NO 39
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 39
gataccaaac ggaactggct gttatgg                                          27

<210> SEQ ID NO 40
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 40
atcgacgcaa ccatcgaagc agc                                              23

<210> SEQ ID NO 41
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 41
gatctttgcc cggtgtatga aacc                                             24

<210> SEQ ID NO 42
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 42
tcggaggagg ccatggtgat gtctgctcaa gc                                    32

<210> SEQ ID NO 43
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 43
gacatcacca tggcctcctc cgaggacgtc atc                                   33

<210> SEQ ID NO 44
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 44
ggctccagcg cctgcaccag ctccggcgcc ggtggagtgg cggc                       44

<210> SEQ ID NO 45
<211> LENGTH: 44
<212> TYPE: DNA
<213> ORGANISM: Artificial Sequence
<220> FEATURE:

```
<223> OTHER INFORMATION: Synthetic oligonucleotide

<400> SEQUENCE: 45
ggagctggtg caggcgctgg agccactggc ggcaaatctg gtgg            44

<210> SEQ ID NO 46
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 46
atctggaggg gacaggcagt ttat                                  24

<210> SEQ ID NO 47
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 47
gggtttcgaa ctacatcaag ggtccaagac cgacatcgag gctctgtaca gtgaccggtg  60

<210> SEQ ID NO 48
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 48
agggaattct cagggcagg gcatgc                                 26

<210> SEQ ID NO 49
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 49
gaaggtcgat gatggtgtga tg                                    22

<210> SEQ ID NO 50
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 50
ctagaggtaa agatcaaggt ag                                    22

<210> SEQ ID NO 51
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 51
ctgatggctg aatgaagcac ag                                    22
```

<210> SEQ ID NO 52
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 52
tgctttacga cgatagccat gc                                              22

<210> SEQ ID NO 53
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 53
ggtgaagagc attgtttgag gcagcggcca gtctttagac aaatg                     45

<210> SEQ ID NO 54
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 54
agtgcctcct ctcagacaga ataggataac gaatactaaa gaccg                     45

<210> SEQ ID NO 55
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 55
tatgcactgg cactcaagca accg                                            24

<210> SEQ ID NO 56
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 56
gtgcatgacg gtcgtatctg gtcc                                            24

<210> SEQ ID NO 57
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 57
ggctgtagtc gctttgtt                                                   18

<210> SEQ ID NO 58
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 58
gcccagtgta agaaagga                                                  18

<210> SEQ ID NO 59
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 59
gctgtcgatc tttgtaccct g                                              21

<210> SEQ ID NO 60
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 60
cgttcctgga tgtggtcgcc t                                              21

<210> SEQ ID NO 61
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 61
atataagctt aatggctaca cttgcagcac cac                                 33

<210> SEQ ID NO 62
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 62
atatgtcgac ttaacgcatg gtggcaggct ttg                                 33

<210> SEQ ID NO 63
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 63
atataagctt aatgcagcag cccaagcgcg cgag                                34

<210> SEQ ID NO 64
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 64
atatgaattc atgagtgcgg cgaactatcc ag                                  32

<210> SEQ ID NO 65
<211> LENGTH: 33

```
<212> TYPE: DNA
<213> ORGANISM: Artificial Sequence
<220> FEATURE:
<223> OTHER INFORMATION: Synthetic oligonucleotide

<400> SEQUENCE: 65
atatgtcgac tcaccgagga gttccgttcg ctg                                    33

<210> SEQ ID NO 66
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 66
atatgaattc atgtttgaga tgggcccggt gggaac                                 36

<210> SEQ ID NO 67
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 67
atatgtcgac ttatcttaat ggtttcctag cctg                                   34

<210> SEQ ID NO 68
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 68
atataagctt atcaacgagc atcagcacaa ac                                     32

<210> SEQ ID NO 69
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 69
atatgtcgac tccatattcc actgccgacg gac                                    33

<210> SEQ ID NO 70
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 70
atatgaattc tctgatagga cagccatgca aatc                                   34

<210> SEQ ID NO 71
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 71
```
atatgaattc atgtacgctg ttgaggatag         30

<210> SEQ ID NO 72
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 72
atatgtcgac ttagtattcg ttatccagac ca         32

<210> SEQ ID NO 73
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 73
atatgaattc acggtagcgc gggtatcgga g         31

<210> SEQ ID NO 74
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 74
atatgaattc atgtcttcat cgtatccacc ac         32

<210> SEQ ID NO 75
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 75
atatctcgag accaggcacc gggacggaga tg         32

<210> SEQ ID NO 76
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 76
atatctcgag agtaggaata gtccctactc gtg         33

<210> SEQ ID NO 77
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 77
atatctcgag tccaggccct ggagtaactg gctg         34

<210> SEQ ID NO 78
<211> LENGTH: 23
<212> TYPE: DNA
<213> ORGANISM: Artificial Sequence

```
<220> FEATURE:
<223> OTHER INFORMATION: Synthetic oligonucleotide

<400> SEQUENCE: 78
ttcgctagac agctcattct acg                                              23

<210> SEQ ID NO 79
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 79
tagtattcgt tatccagacc atcg                                             24

<210> SEQ ID NO 80
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 80
atacctggat aaaccaaatc gagc                                             24

<210> SEQ ID NO 81
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 81
aggttcattc gcagggctag ac                                               22

<210> SEQ ID NO 82
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 82
accactacag ctaccactct cc                                               22

<210> SEQ ID NO 83
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 83
tttcgatgct ctctgagacg gc                                               22

<210> SEQ ID NO 84
<211> LENGTH: 16
<212> TYPE: PRT
<213> ORGANISM: Aspergillus nidulans

<400> SEQUENCE: 84

Arg Leu Glu Val Ile Ser Asn Pro Phe Ile Val Tyr Ser Ala Lys Lys
1               5                   10                  15
```

-continued

```
<210> SEQ ID NO 85
<211> LENGTH: 16
<212> TYPE: PRT
<213> ORGANISM: Aspergillus nidulans

<400> SEQUENCE: 85

Arg Leu Glu Val Ile Ser Asn Pro Phe Ile Val Tyr Ser Ala Lys Lys
1               5                   10                  15

<210> SEQ ID NO 86
<211> LENGTH: 16
<212> TYPE: PRT
<213> ORGANISM: Aspergillus nidulans

<400> SEQUENCE: 86

Arg Leu Glu Val Ile Ser Asn Pro Phe Ile Val Tyr Ser Ala Lys Lys
1               5                   10                  15

<210> SEQ ID NO 87
<211> LENGTH: 15
<212> TYPE: PRT
<213> ORGANISM: Aspergillus nidulans

<400> SEQUENCE: 87

Lys Ile Gly Val Trp Phe Val Leu Gln Asp Leu Ser Val Arg Thr
1               5                   10                  15

<210> SEQ ID NO 88
<211> LENGTH: 18
<212> TYPE: PRT
<213> ORGANISM: Aspergillus nidulans

<400> SEQUENCE: 88

Lys Ser Val Ser Asp Leu Pro Gln Ser Asp Ile Ala Glu Val Ile Asn
1               5                   10                  15

Lys Gly

<210> SEQ ID NO 89
<211> LENGTH: 14
<212> TYPE: PRT
<213> ORGANISM: Aspergillus nidulans

<400> SEQUENCE: 89

Arg Ile Trp Ser Leu Gln Val Val Gln Gln Pro Ile Arg Ala
1               5                   10

<210> SEQ ID NO 90
<211> LENGTH: 16
<212> TYPE: PRT
<213> ORGANISM: Aspergillus nidulans

<400> SEQUENCE: 90

Lys Glu Ile His Ala Tyr Asn Ile Leu His Ile Tyr Gln Ala Arg Lys
1               5                   10                  15

<210> SEQ ID NO 91
<211> LENGTH: 14
<212> TYPE: PRT
<213> ORGANISM: Aspergillus nidulans

<400> SEQUENCE: 91

Arg Tyr Ala Val Ala Gly Gly Pro Ala Pro Trp Asn Arg Asn
1               5                   10
```

```
<210> SEQ ID NO 92
<211> LENGTH: 17
<212> TYPE: PRT
<213> ORGANISM: Aspergillus nidulans

<400> SEQUENCE: 92

Arg Val Ser Glu Ser Leu Ile Tyr Ala Pro His Pro Thr Asn Gly Arg
1               5                   10                  15

Phe

<210> SEQ ID NO 93
<211> LENGTH: 16
<212> TYPE: PRT
<213> ORGANISM: Aspergillus nidulans

<400> SEQUENCE: 93

Lys Ile Ile Gln Val Ala Leu Asp Gly Leu Glu Asn Ile Leu Lys Val
1               5                   10                  15

<210> SEQ ID NO 94
<211> LENGTH: 13
<212> TYPE: PRT
<213> ORGANISM: Aspergillus nidulans

<400> SEQUENCE: 94

Lys Ile Gln Ala Val Ile Glu Ala Gly Ile Pro Arg Arg
1               5                   10

<210> SEQ ID NO 95
<211> LENGTH: 20
<212> TYPE: PRT
<213> ORGANISM: Aspergillus nidulans

<400> SEQUENCE: 95

Lys Thr Pro Gln Pro Asp Trp Asn Thr Ile Ala Pro Ala Leu Pro Val
1               5                   10                  15

Leu Ala Lys Leu
            20

<210> SEQ ID NO 96
<211> LENGTH: 22
<212> TYPE: PRT
<213> ORGANISM: Aspergillus nidulans

<400> SEQUENCE: 96

Lys Gly Thr Ala Pro Ile Leu Ala Ser Thr Phe Ser Glu Pro Phe Gln
1               5                   10                  15

Val Phe Ser Ala Lys Lys
            20

<210> SEQ ID NO 97
<211> LENGTH: 15
<212> TYPE: PRT
<213> ORGANISM: Aspergillus nidulans

<400> SEQUENCE: 97

Lys Ile Gly Val Trp Phe Val Leu Gln Asp Leu Ser Val Arg Thr
1               5                   10                  15

<210> SEQ ID NO 98
<211> LENGTH: 18
<212> TYPE: PRT
<213> ORGANISM: Aspergillus nidulans
```

```
<400> SEQUENCE: 98

Lys Ser Val Ser Asp Leu Pro Gln Ser Asp Ile Ala Glu Val Ile Asn
1               5                   10                  15

Lys Gly

<210> SEQ ID NO 99
<211> LENGTH: 18
<212> TYPE: PRT
<213> ORGANISM: Aspergillus nidulans

<400> SEQUENCE: 99

Lys Asp Ala Thr Glu Gly Thr Gln Pro Met Pro Ser Pro Val Pro Gly
1               5                   10                  15

Lys Leu

<210> SEQ ID NO 100
<211> LENGTH: 15
<212> TYPE: PRT
<213> ORGANISM: Aspergillus nidulans

<400> SEQUENCE: 100

Lys Lys Phe Pro Gly Leu Thr Thr Ser Thr Pro Ile Ser Arg Met
1               5                   10                  15

<210> SEQ ID NO 101
<211> LENGTH: 28
<212> TYPE: PRT
<213> ORGANISM: Aspergillus nidulans

<400> SEQUENCE: 101

Lys Leu Met Thr Asn Gln Gly Ser Pro Val Leu Thr Gly Val Pro Val
1               5                   10                  15

Ala Gly Val Ala Tyr Leu Asp Lys Pro Asn Arg Ala
            20                  25

<210> SEQ ID NO 102
<211> LENGTH: 16
<212> TYPE: PRT
<213> ORGANISM: Aspergillus nidulans

<400> SEQUENCE: 102

Lys Glu Ile His Ala Tyr Asn Ile Leu His Ile Tyr Gln Ala Arg Lys
1               5                   10                  15

<210> SEQ ID NO 103
<211> LENGTH: 11
<212> TYPE: PRT
<213> ORGANISM: Aspergillus nidulans

<400> SEQUENCE: 103

Arg Ile Gln Gln Leu Ala Ala Asp Val Lys Ser
1               5                   10

<210> SEQ ID NO 104
<211> LENGTH: 14
<212> TYPE: PRT
<213> ORGANISM: Aspergillus nidulans

<400> SEQUENCE: 104

Arg Tyr Ala Val Ala Gly Gly Pro Ala Pro Trp Asn Arg Asn
1               5                   10
```

```
<210> SEQ ID NO 105
<211> LENGTH: 20
<212> TYPE: PRT
<213> ORGANISM: Aspergillus nidulans

<400> SEQUENCE: 105

Lys Asp Val Asp Asn Thr Asp Gly Gly Phe Phe Val Trp Gly Asp Leu
1               5                   10                  15

Ser Ile Lys Val
            20

<210> SEQ ID NO 106
<211> LENGTH: 22
<212> TYPE: PRT
<213> ORGANISM: Aspergillus nidulans

<400> SEQUENCE: 106

Arg Leu Lys Asp Val Asp Asn Thr Asp Gly Gly Phe Phe Val Trp Gly
1               5                   10                  15

Asp Leu Ser Ile Lys Val
            20

<210> SEQ ID NO 107
<211> LENGTH: 16
<212> TYPE: PRT
<213> ORGANISM: Aspergillus nidulans

<400> SEQUENCE: 107

Lys Glu Ile His Ala Tyr Asn Ile Leu His Ile Tyr Gln Ala Arg Lys
1               5                   10                  15

<210> SEQ ID NO 108
<211> LENGTH: 22
<212> TYPE: PRT
<213> ORGANISM: Aspergillus nidulans

<400> SEQUENCE: 108

Arg Trp Tyr Asn Leu Ala Val Ser Glu Ser Ile Glu Asn Leu Ser Leu
1               5                   10                  15

Ala Pro Phe Ser Arg Val
            20

<210> SEQ ID NO 109
<211> LENGTH: 14
<212> TYPE: PRT
<213> ORGANISM: Aspergillus nidulans

<400> SEQUENCE: 109

Arg Tyr Ala Val Ala Gly Gly Pro Ala Pro Trp Asn Arg Asn
1               5                   10

<210> SEQ ID NO 110
<211> LENGTH: 22
<212> TYPE: PRT
<213> ORGANISM: Aspergillus nidulans

<400> SEQUENCE: 110

Lys Gly Thr Ala Pro Ile Leu Ala Ser Thr Phe Ser Glu Pro Phe Gln
1               5                   10                  15

Val Phe Ser Ala Lys Lys
            20

<210> SEQ ID NO 111
```

```
-continued

<211> LENGTH: 18
<212> TYPE: PRT
<213> ORGANISM: Aspergillus nidulans

<400> SEQUENCE: 111

Lys Ser Val Ser Asp Leu Pro Gln Ser Asp Ile Ala Glu Val Ile Asn
1               5                   10                  15

Lys Gly

<210> SEQ ID NO 112
<211> LENGTH: 14
<212> TYPE: PRT
<213> ORGANISM: Aspergillus nidulans

<400> SEQUENCE: 112

Arg Ile Trp Ser Leu Gln Val Val Gln Gln Pro Ile Arg Ala
1               5                   10

<210> SEQ ID NO 113
<211> LENGTH: 16
<212> TYPE: PRT
<213> ORGANISM: Aspergillus nidulans

<400> SEQUENCE: 113

Arg Leu Glu Val Ile Ser Asn Pro Phe Ile Val Tyr Ser Ala Lys Lys
1               5                   10                  15

<210> SEQ ID NO 114
<211> LENGTH: 21
<212> TYPE: PRT
<213> ORGANISM: Aspergillus nidulans

<400> SEQUENCE: 114

Arg Arg Pro Asp Gln Tyr Ala Gly Ser Asp Ala Tyr Ala Asn Ala Pro
1               5                   10                  15

Glu Arg Pro Arg Ser
            20

<210> SEQ ID NO 115
<211> LENGTH: 19
<212> TYPE: PRT
<213> ORGANISM: Aspergillus nidulans

<400> SEQUENCE: 115

Arg Arg Pro Ser Ala Val Glu Tyr Gly Gln Pro Ile Ala Gln Pro Tyr
1               5                   10                  15

Gln Arg Pro

<210> SEQ ID NO 116
<211> LENGTH: 573
<212> TYPE: PRT
<213> ORGANISM: Aspergillus nidulans

<400> SEQUENCE: 116

Met Ala Thr Leu Ala Ala Pro Pro Pro Leu Gly Glu Ser Gly Asn
1               5                   10                  15

Ser Asn Ser Val Ser Arg Ile Thr Arg Glu Gly Lys Lys Ile Thr Tyr
                20                  25                  30

Lys Leu Asn Ile Met Gln Gln Pro Lys Arg Ala Arg Ala Cys Gly Gln
            35                  40                  45

Gly Ser Lys Ser His Thr Asp Arg Arg Pro Val Asp Pro Pro Val
        50                  55                  60
```

```
Ile Glu Leu Asn Ile Phe Glu Ser Asp Pro His Asp Ser Asn Lys
 65                  70                  75                  80

Thr Asp Ile Thr Phe Val Tyr Asn Ala Asn Phe Phe Leu Phe Ala Thr
                 85                  90                  95

Leu Glu Pro Glu Arg Pro Ile Ala Thr Gly Lys Leu Met Thr Asn Gln
            100                 105                 110

Gly Ser Pro Val Leu Thr Gly Val Pro Val Ala Gly Val Ala Tyr Leu
            115                 120                 125

Asp Lys Pro Asn Arg Ala Gly Tyr Phe Ile Phe Pro Asp Leu Ser Val
            130                 135                 140

Arg Asn Glu Gly Ser Tyr Arg Phe Ser Phe His Leu Phe Glu Gln Ile
145                 150                 155                 160

Lys Asp Pro Lys Asp Ala Thr Glu Gly Thr Gln Pro Met Pro Ser Pro
                165                 170                 175

Val Pro Gly Lys Leu Ser Ser Pro Gln Glu Phe Leu Glu Phe Arg Leu
            180                 185                 190

Glu Val Ile Ser Asn Pro Phe Ile Val Tyr Ser Ala Lys Lys Phe Pro
            195                 200                 205

Gly Leu Thr Thr Ser Thr Pro Ile Ser Arg Met Ile Ala Glu Gln Gly
210                 215                 220

Cys Arg Val Arg Ile Arg Arg Asp Val Arg Met Arg Arg Gly Asp
225                 230                 235                 240

Lys Arg Thr Glu Asp Tyr Asp Tyr Asp Asn Glu Arg Gly Tyr Asn Asn
                245                 250                 255

Arg Arg Pro Asp Gln Tyr Ala Gly Ser Asp Ala Tyr Ala Asn Ala Pro
            260                 265                 270

Glu Arg Pro Arg Ser Thr Ser Ile Ser Thr Asn Met Asp Pro Tyr Ser
            275                 280                 285

Tyr Pro Ser Arg Arg Pro Ser Ala Val Glu Tyr Gly Gln Pro Ile Ala
            290                 295                 300

Gln Pro Tyr Gln Arg Pro Met Ala Ser Thr Pro Ala Pro Ser Ser Thr
305                 310                 315                 320

Pro Ile Pro Ala Pro Ile Pro Met Pro Gly Pro Val Ala Leu Pro Pro
                325                 330                 335

Ser Thr Pro Ser Pro Ala Ser Ala His Ala Pro Ala Pro Pro Ser Val
            340                 345                 350

Pro Leu Ala Ala Pro Pro Leu His Thr Pro Ser Tyr Gln Ser His
            355                 360                 365

Leu Ser Phe Gly Ala Thr Gln Thr Gln Tyr Pro Ala Pro Gln Leu Ser
            370                 375                 380

His Ile Pro Gln Gln Thr Thr Thr Pro Thr His Pro Tyr Ser Pro Arg
385                 390                 395                 400

Ser Ser Ile Ser His Ser Arg Asn Gln Ser Ile Ser Glu Tyr Glu Pro
                405                 410                 415

Ser Met Gly Tyr Pro Gly Ser Gln Thr Arg Leu Ser Ala Glu Arg Pro
            420                 425                 430

Ser Tyr Gly Gln Pro Ser Gln Thr Thr Ser Leu Pro Pro Leu Arg His
            435                 440                 445

Ser Leu Glu Pro Ser Val Asn Ser Arg Ser Lys Thr Pro Ser Asn Met
            450                 455                 460

Ile Thr Ser Leu Pro Pro Ile Gln Ser Leu Ser Glu Leu Pro Ser Thr
465                 470                 475                 480
```

```
Thr Ser Gln Pro Ser Ser Ala Ile Gly Ser Ser Pro Ala Asn Glu Pro
                485                 490                 495

Gly Pro Arg Leu Trp Glu Thr Asn Ser Met Leu Ser Lys Arg Thr Tyr
            500                 505                 510

Glu Glu Ser Phe Gly His Asp Asp Arg Pro Leu Tyr Asn Gly Met Arg
            515                 520                 525

Pro Asp Ser Glu Ser Tyr Pro Gly Gly Met Gln Arg Arg Pro Ser Tyr
        530                 535                 540

Glu Arg Ser Ser Leu Leu Asp Gly Pro Asp Gln Met Ala Tyr Lys Arg
545                 550                 555                 560

Ala Asn Gly Arg Met Val Ser Lys Pro Ala Thr Met Arg
                565                 570

<210> SEQ ID NO 117
<211> LENGTH: 369
<212> TYPE: PRT
<213> ORGANISM: Aspergillus nidulans

<400> SEQUENCE: 117

Met Tyr Ala Val Glu Asp Arg Ala His Ser Gly His His Pro Pro Pro
1               5                   10                  15

Leu Ser Met Asp Arg Ile Pro Pro Ser Thr Met Tyr Pro Ser Ser
            20                  25                  30

Ala Gly Pro Ser Ala Met Val Ser Pro Ala Gly Gln Pro Glu Pro Glu
            35                  40                  45

Ser Leu Ser Thr Val His Asp Gly Arg Ile Trp Ser Leu Gln Val Val
        50                  55                  60

Gln Gln Pro Ile Arg Ala Arg Met Cys Gly Phe Gly Asp Lys Asp Arg
65                  70                  75                  80

Arg Pro Ile Thr Pro Pro Cys Ile Arg Leu Ile Val Lys Asp Ala
                85                  90                  95

Gln Thr Gln Lys Glu Val Asp Ile Asn Ser Leu Asp Ser Ser Phe Tyr
            100                 105                 110

Val Val Met Ala Asp Leu Trp Asn Ala Asp Gly Thr His Glu Val Asn
        115                 120                 125

Leu Val Lys His Ser Ala Thr Ser Pro Ser Ile Ser Thr Ala Met Ser
    130                 135                 140

Ser Ser Tyr Pro Pro Pro Pro His Pro Thr Ser Ser Asp Tyr Pro Ala
145                 150                 155                 160

Ser Tyr Gln Thr Asn Pro Tyr Gly Gln Pro Val Gly Gln Pro Val Gly
                165                 170                 175

Gln Pro Val Gly Tyr Ala Gly Val Gly Asn Tyr Tyr Gly Gly Ser Thr
            180                 185                 190

Gln Leu Gln Tyr Gln Asn Ala Tyr Pro Asn Pro Gln Ala Gln Tyr Tyr
        195                 200                 205

Gln Pro Met Tyr Gly Gly Met Ala Gln Pro Gln Met Pro Ala Ala Gln
    210                 215                 220

Pro Val Thr Pro Gly Pro Gly Gly Met Phe Thr Arg Asn Leu Ile Gly
225                 230                 235                 240

Cys Leu Ser Ala Ser Ala Tyr Arg Leu Tyr Asp Thr Glu Asp Lys Ile
                245                 250                 255

Gly Val Trp Phe Val Leu Gln Asp Leu Ser Val Arg Thr Glu Gly Ile
            260                 265                 270

Phe Arg Leu Lys Phe Ser Phe Val Asn Val Gly Lys Ser Val Ser Asp
        275                 280                 285
```

Leu Pro Gln Ser Asp Ile Ala Glu Val Ile Asn Lys Gly Thr Ala Pro
    290                 295                 300

Ile Leu Ala Ser Thr Phe Ser Glu Pro Phe Gln Val Phe Ser Ala Lys
305                 310                 315                 320

Lys Phe Pro Gly Val Ile Glu Ser Thr Pro Leu Ser Lys Val Phe Ala
                325                 330                 335

Asn Gln Gly Ile Lys Ile Pro Ile Arg Lys Asp Gly Val Lys Gly Gln
            340                 345                 350

Gly Ser Arg Gly Arg His Ser Asp Glu Asp Asp Gly Leu Asp Asn Glu
        355                 360                 365

Tyr

<210> SEQ ID NO 118
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 118
acaaccctgg actctggaat                                              20

<210> SEQ ID NO 119
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 119
cgaagagggt gaagagcatt gtttgaggca gaggacgcgt tgactgtgat g          51

<210> SEQ ID NO 120
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 120
tgacgacaat acctcccgac gatacctggg ttgattcctg cttttcctcc              50

<210> SEQ ID NO 121
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 121
tctcgttctc ccatttacct                                              20

<210> SEQ ID NO 122
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 122
tgcctcaaac aatgctcttc                                              20

```
<210> SEQ ID NO 123
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 123
caaggtatcg tcgggaggt                                                    19

<210> SEQ ID NO 124
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 124
aatcacggac ctcgaagcag                                                   20

<210> SEQ ID NO 125
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 125
ggggtcttga tatggcgaat                                                   20

<210> SEQ ID NO 126
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 126
caacaagacc gacatcacct tc                                                22

<210> SEQ ID NO 127
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 127
ccattcttgg gatagctgca ac                                                22

<210> SEQ ID NO 128
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 128
caacgaacta gtccgcctgc ccttaacctc ca                                     32

<210> SEQ ID NO 129
<211> LENGTH: 32
<212> TYPE: DNA
<213> ORGANISM: Artificial Sequence
<220> FEATURE:
<223> OTHER INFORMATION: Synthetic oligonucleotide
```

```
<400> SEQUENCE: 129
gcatacacta gtctcgcatg ccagtggatg gg                              32

<210> SEQ ID NO 130
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 130
catcggttga ctacgctcgc a                                         21

<210> SEQ ID NO 131
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 131
gacctgtggt gaaacctgag g                                         21

<210> SEQ ID NO 132
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 132
ctagctggtc attatttgat ctcg                                      24

<210> SEQ ID NO 133
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 133
gttgtagagt ggacgatcat catg                                      24

<210> SEQ ID NO 134
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 134
ccttgtatga tgtatgtatg atgagc                                    26

<210> SEQ ID NO 135
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 135
gacagcgaaa gtgaagagga catc                                      24

<210> SEQ ID NO 136
<211> LENGTH: 20
```

```
<212> TYPE: DNA
<213> ORGANISM: Artificial Sequence
<220> FEATURE:
<223> OTHER INFORMATION: Synthetic oligonucleotide

<400> SEQUENCE: 136
gaagcggtct gaatctcctg                                                   20

<210> SEQ ID NO 137
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 137
acagtccaag cgtggtatcc                                                   20

<210> SEQ ID NO 138
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 138
agagtcttcc ttcagccagg tc                                                22

<210> SEQ ID NO 139
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 139
gtggggcttt tcttcattct cg                                                22

<210> SEQ ID NO 140
<211> LENGTH: 3662
<212> TYPE: DNA
<213> ORGANISM: Aspergillus flavus

<400> SEQUENCE: 140
acctcacagc tggctgagtt cccactggat cggccattct tcttttttta cccctcttc       60
tgtgacacca tccaccttcc cccatttag tgccatccgt gctgacccaa tacccaccat       120
atcggctcag tcgtgcagag ttagtgccgt cgtacatacc agctccatta gaaggtactg     180
tacatacgcc atgtatctac ggggtaattc cggttgccgt cgtcagaacg gataaacatc     240
tcctattgac cctctcgata agaaagagca agttcagagc gaataaaatg ctcgaagcgc     300
agaaatgcga ccgtagaccc atggtaccgg gatatttaag aacgcaagtt atgtatgggg     360
ccgtcagccc gatcaccatg ttgttggaac ttggaaccga tggaaaccgt caccgtcggt     420
aatcttacag taccacggct ccggagacga gacggttagg gtgttatagt tggttgcgat     480
agtgtgtgta cctgccgatt ctcaggctga ctcgtccttt gacttttccc gtcctcgctc     540
gctccacccc ctctcattca ttattcttcg tcccccccgt atcaccaact tgactttgt     600
tactcctctc ccatacctct tttcctcatc ctggacgggt caatcgctgg attgtctgtt    660
gtactgcctc ggcgcagcgg acccagttta aattttttt tttttttaatt tcattatcct     720
tcttttcccc ttttggtcga cagttggaat ctctctcgtt ttccgtttcg cagacgactt    780
```

```
cgagaacatc cttgaccgac tggtcggttt cacggcttgc attcgtggga gtcacgcccg      840
acataaccag cacactagaa gaaaaccaga ttcacacggg aaacggggat agattacttg      900
cttgacgcaa gcactttccc atagcgttga ttttgtttgg ttggaccgag ggattgccaa      960
gtaagtccca agcttcattg ctagctggtc attatttgat ctcgaccatg aaattgtggt     1020
caattacgcc cgtcgaatct tgttgtgcta atcctggcag ttttttcgcat cacagtcaag     1080 gcgtctccaa aatggcgaca cgagctcctt tggcgcctcc gccgaacgag acggaagcct     1140
ccgtcagccg gatcactcga gagggcaaga agctcaccta taaactcaat gtcatgcaac     1200
agcctgagcg tgcgcgagcc tgcggtgcag gtgcaaagtg tatgcgtcca accagcactc     1260
cataaccgga tagcatcaaa ctgatggttc tgactttata tagcctctgc ggaccgtcgt     1320
ccagtcgatc ctccaccggt cgtcgaactt cgagtgtacg agtccgatcc caacgacgac     1380
ctcaacaaga ccgacatcac cttcgcatac aacgccaatt tcttcctgta cgccactttg     1440
gaaaccgctc gtcccatggc caaggccgt tttgccccga atccgacttg tccagtattg      1500
accggtgtgc ccgtggctgg agtggcttac ttggaccgcc catctcaagc cggttacttc     1560
atcttccccg atctttccgt gcggcatgaa ggtgtatatc gattgaactt ccacctgtac     1620
gaggaaacca aggagagcaa ggatgcgaac gagaatgctc cgatccagtc catgtccaac     1680
ccaatgccat cgaagccgat ggcgccgaag tcattcctgg agtttcgtct cgaggtcgtt     1740
tccgttccgt tcaccgtatt taacgccaag aagttcccag gattggccac gagtacctcc     1800
ctgagtcggg tcattgcgga gcaaggttgt cgtgtgcgga ttcgacgtga tgtccgcatg     1860
agacgtcggg gagagaagcg caccgatgac tacgactacg atgaggagag agtctaccga     1920
tcttctgacc gaatctctac cccagatacc cacgggtacg ccggcactcc cgttgaacgt     1980
cctcgatcaa ccagtaccag cacggtggat ccctcattcc cctacggtgt cgatgctcag     2040
cgccggtcat ctggcgcgac cgagtatggt ttccagggtg cacagccgta ccaacgacca     2100
ttgccgcctg ctccgggtcc cgcaccagcc gctgtttcca cgcccgctcc tcccgctcct     2160
cccgcgccac catcccataa tcctggatat caatcgcatc tttcctttgg ctcgactcaa     2220
actcaatatc cagctcccca gctgcctcca actccacaga ccgcgtcgac attggcagct     2280
ccgtactcgc cccatccatc gtattctcat gctcggaatc catcgacgag ggccgagtat     2340
gaaacgcccg gttactccta tccgccatca cggatgtcaa cggaacgttc cagctatccc     2400
aagaatggct tgcctccgct ccgcttggaa ccgcctaagc cactaaatat gccatccggc     2460
gagccacgct cgtccgatct gaacgcatat cattccgtgg ctcaatcggc ggcacccgg      2520 tctcagacac cgtcatccag tctggtgcct tcccttccgc ccctcaaggc tctatcgggg     2580
gattatccca acaacctctc tcaatcatcc agcagtacct ctcagagccc cagtcacgat     2640
ctcggcgctg gcaagaagtt cttctgggat acgggcgcca gcctgtccaa gcggtcgtac     2700
gaagattcgt ttggccatga tgatcgtcca ctctacaacg gcatgcgccc cgatacggaa     2760
agttatcctc ggaggctgtc agatgccagt cggaacttct acaacgaaac gcgcgatgaa     2820
atggcgtaca aacgagccaa cgggagaatg ccacgaagaa tatcccctgc actccagtaa     2880
aacaagttga ttcctgcttt tcctcccgct catatagtga cggcgtcttg gcgtaacggt     2940
cgtcgattga tttctttccc gtaatctgtt ccttttccta atgtactctg gtgtgatggg     3000
cttcagggac tctttaacg acccagactt tgatgttta taccaccgtt cttttcttc       3060 tttcctcgat ctttggcatt attgtacatg atgctctgca tgtggtttc aagatattcc      3120 ccggattgtt cttgtcttca gtttatatac ggccgctctc gtgtttatta tccgctgtgt     3180
```

```
ttccaggtcg gctggacctg gggcctctcc cttcccgcga atagaagtga gtgagcaata    3240
caaatgtgac attgtccaaa agtttggtga tctgaacgcg caacctggat gcattgatcc    3300
gagacaatca cggggtctta gacatgcgac atgtctgatt cactccttcg accatttcct    3360
tgtttatcca tgaccatgcc ccatccactg gcatgcgaga atgacgtatg cgacagataa    3420
gatcgacgat ctgccttata tatccgaatt gatccgattg tcaatactct ctcttagtgt    3480
tgtataagta tatatatgtg ctgtagagta tgtcctggct gtctcccata cagaagaagc    3540
catgtcgaga aagggtatgt ccaccagagt aagattgtac attccttgga catgtcattg    3600
tcatttcaca ggaaatatcg aagggtcatg gattcggagg aacattccag ggaagagaca    3660
cc                                                                  3662

<210> SEQ ID NO 141
<211> LENGTH: 4406
<212> TYPE: DNA
<213> ORGANISM: Aspergillus flavus

<400> SEQUENCE: 141
aatcacggac ctcgaagcag tgggccttct ccaccctcga actgcctgtt caagttgtta      60 ggttttgta tttaattat tattttctt ttgtctgaat tttctcacaa cttatttgtt     120
atgcagccaa tgtctaaacc ccaccggacc caatgaccaa gccggccgca gtcgccatga    180
cccaacgacc gtaaccgcct gcccttaacc tccagctggc tgagttccca ctggatcggc    240
cattcttctt tttttacccc ctcttctgtg acaccatcca ccttccccca ttttagtgcc    300
atccgtgctg acccaatacc caccatatcg gctcagtcgt gcagagttag tgccgtcgta    360
cataccagct ccattagaag gtactgtaca tacgccatgt atctacgggg taattccggt    420
tgccgtcgtc agaacggata acatctcct attgaccctc tcgataagaa agagcaagtt    480
cagagcgaat aaaatgctcg aagcgcagaa atgcgaccgt agacccatgg taccgggata    540
tttaagaacg caagttatgt atggggccgt cagcccgatc accatgttgt tggaacttgg    600
aaccgatgga aaccgtcacc gtcggtaatc ttacagtacc acggctccgg agacgagacg    660
gttagggtgt tatagttggt tgcgatagtg tgtgtacctg ccgattctca ggctgactcg    720
tcctttgact tttcccgtcc tcgctcgctc caccccctct cattcattat tcttcgtccc    780
ccccgtatca ccaacttgac ttttgttact cctctcccat accttctttc ctcatcctgg    840
acgggtcaat cgctggattg tctgttgtac tgcctcggcg cagcggaccc agtttaaatt    900 ttttttttt tttaatttca ttatccttct ttttcccttt tggtcgacag ttggaatctc    960
tctcgttttc cgtttcgcag acgacttcga gaacatcctt gaccgactgg tcggtttcac   1020
ggcttgcatt cgtgggagtc acgcccgaca taaccagcac actagaagaa accagattc    1080 acacgggaaa cggggataga ttacttgctt gacgcaagca ctttcccata gcgttgattt   1140
tgtttggttg gaccgaggga ttgccaagta agtcccaagc ttcattgcta gctggtcatt   1200
atttgatctc gaccatgaaa ttgtggtcaa ttacgcccgt cgaatcttgt tgtgctaatc   1260
ctggcagttt ttcgcatcac agtcaaggcg tctctgcctc aaacaatgct cttccaaaat   1320
ggcgacacga gctcctttgg cgcctccgcc gaacgagacg gaagcctccg tcagccggat   1380
cactcgagag ggcaagaagc tcacctataa actcaaatgt catgcaacag cctgagcgtg   1440
cgcgagcctg cggtgcaggt gcaaagtgta tgcgtccaac cagcactcca taaccggata   1500
gcatcaaact gatggttctg actttatata gcctctgcgg accgtcgtcc agtcgatcct   1560
```

```
ccaccggtcg tcgaacttcg agtgtacgag tccgatccca cgacgacct  caacaagacc   1620 gacatcacct tcgcatacaa cgccaatttc ttcctgtacg ccactttgga accgctcgtc   1680
ccatggccca aggccgtttt gccccgaatc cgacttgtcc agtattgacc ggtgtgcccg   1740
tggctggagt ggcttacttg gaccgcccat ctcaagccgg ttacttcatc ttccccgatc   1800
tttccgtgcg gcatgaaggt gtatatcgat tgaacttcca cctgtacgag gaaaccaagg   1860
agagcaagga tgcgaacgag aatgctccga tccagtccca tgtccaaccc aatgccatcg   1920
aagcccgatg gcgccgaagt cattcctgga gtttcgtctc gaggtcgttt ccgttccgtt   1980
caccgtattt agcgccaaga agttcccagg attggccacg agtacctccc tgagtcgggt   2040
cattgcggag caaggttgtc gtgtgcggat tcgacgtgat gtccgcatga gacgtcgggg   2100
agagaagcgc accgatgact acgactacga tgaggagaga gtctaccgat cttctgaccg   2160
aatctctacc ccagatacc  acgggtacgc cggcactccc gttgaacgtc ctcgatcaac   2220
cagtaccagc acgtggatc  cctcattccc ctacggtgtc gatgctcagc gccggtcatc   2280
tggcgcgacc gagtatggtt tccagggtgc acagccgtac caacgaccat tgccgcctgc   2340
tccgggtccc gcaccagccg ctgtttccac gcccgctcct cccgctcctc ccgcgccacc   2400
atcccataat cctggatatc aatcgcatct ttcctttggc tcgactcaaa ctcaatatcc   2460
agctccccag ctgcctccaa ctccacagac cgcgtcgaca ttggcagctc cgtactcgcc   2520
ccatccatcg tattctcatg ctcggaatcc atcgacgagc gccgagtatg aaacgcccgg   2580
ttactcctat ccgccatcac ggatgtcaac ggaacgttcc agctatccca agaatggctt   2640
gcctccgctc cgcttggaac cgcctaagcc actaaatatg ccatccggcg agccacgctc   2700
gtccgatccg aacgcatatc attccgtggc tcaatcggcg gcaccccggt ctcagacacc   2760
gtcatccagt ctggtgcctt cccttccgcc cctcaaggct ctatcggggg attatcccaa   2820
caacctctct caatcatcca gcagtacctc tcagagcccc agtcacgatc tcggcgctgg   2880
caagaagttc ttctgggata cgggcgccag cctgtccaag cggtcgtacg aagattcgtt   2940
tggccatgat gatcgtccac tctacaacgg catgcgcccc gatacggaaa gttatcctcg   3000
gaggctgtca gatgccagtc ggaacttcta caacgaaacg cgcgatgaaa tggcgtacaa   3060
acgagccaac gggagaatgg ccacgaagat atcccctgca ctccagtaaa caagttgat   3120 tcctgctttt cctcccgctc ataggacg   gcgtcttggc gaacggtcgt cgattgattt   3180 cttcccgta  atctgttcct tttcctaatg tactctggtg tgatgggctt cagggactct   3240
tttaacgacc cagactttg  atgtttatac caccgttctt tttcttcttt cctcgatctt   3300
tggcattatt gtacatgatg ctctgcatgt ggttttcaag atattccccg gattgttctt   3360
gtcttcagtt tatatacggc cgctctcgtg tttattatcc gctgtgtttc caggtcggct   3420
ggacctgggg cctctcccct cccgcgaata gaagtgagtg agcaatacaa atgtgacatt   3480
gtccaaaagt ttggtgatct gaacgcgcaa cctggatgca ttgatccgag acaatcacgg   3540
ggtcttagac atgcgacatg tctgattcac tccttcgacc atttccttgt ttatccatga   3600
ccatgcccca tccactggca tgcgagaatg acgtatgcga cagataagat cgacgatctg   3660
ccttatatat ccgaattgat tcgattgtca atactctctc ttagtgttgt ataagtatat   3720
atatgtgctg tagagtatgt cctggctgtc tcccatacag aagaagccat gtcgagaaag   3780
ggtatgtcca ccagagtaag attgtacatt ccttggacat gtcattgtca tttcacggaa   3840
aatatcgaag ggtcatggat tcggaggaac attccaggaa gagacaccag aaatgagttg   3900
gcacggatca gtaaacatgt agatctacat aaccttgttc attttcatga tgcactgaca   3960
```

```
ctagagcata gaggcgttta ctttacctct tatcaacgac taattgacat aaccaagcag    4020
tggaattttt atgattcaac gtcccagact atagtgccta ctgttatgat ctacctgcta    4080
ctttgatcgg tttcactttc tttgttggtt gatacttgtt gcgtatcttc tttgattact    4140
tatagtcaat agtccctgtt actatattag cgccgttcct agccattgta tatccttga    4200 tccactactt gaaagaaaat tcgaacaagg gttttaatgg atgtatccat tctatttct    4260 cttttctttg gatgtaatga gatacaaagg tgttctaatc aaaaagtatg tattcaattc    4320
aaatacatct tcccagacaa tctgggaaga ggaataagca agagagataa ttctccgact    4380
cacactattc gccatatcaa gacccc                                        4406
```

<210> SEQ ID NO 142
<211> LENGTH: 4556
<212> TYPE: DNA
<213> ORGANISM: Artificial Sequence
<220> FEATURE:
<223> OTHER INFORMATION: Aspergillus flavus veA knockout with
      Aspergillus fumigatus pyrG

<400> SEQUENCE: 142

```
aatcacggac ctcgaagcag tgggccttct ccaccctcga actgcctgtt caagttgtta      60 ggttttgta ttttaattat tatttctttt ttgtctgaat tttctcacaa cttatttgtt     120
atgcagccaa tgtctaaacc ccaccggacc caatgaccaa gccggccgca gtcgccatga     180
cccaacgacc gtaaccgcct gcccttaacc tccagctggc tgagttccca ctggatcggc     240
cattcttctt ttttaccccc ctcttctgtg acaccatcca ccttcccca ttttagtgcc      300 atccgtgctg acccaatacc caccatatcg gctcagtcgt gcagagttag tgccgtcgta     360
cataccagct ccattagaag gtactgtaca tacgccatgt atctacgggg taattccggt     420
tgccgtcgtc agaacggata aacatctcct attgaccctc tcgataagaa agagcaagtt     480
cagagcgaat aaaatgctcg aagcgcagaa atgcgaccgt agacccatgg taccgggata     540
tttaagaacg caagttatgt atggggccgt cagcccgatc accatgttgt tggaacttgg     600
aaccgatgga aaccgtcacc gtcggtaatc ttacagtacc acggctccgg agacgagacg     660
gttagggtgt tatagttggt tgcgatagtg tgtgtacctg ccgattctca ggctgactcg     720
tcctttgact tttcccgtcc tcgctcgctc caccccctct cattcattat tcttcgtccc     780
ccccgtatca ccaacttgac ttttgttact cctctcccat accttctttc ctcatcctgg     840
acgggtcaat cgctggattg tctgttgtac tgcctcggcg cagcgaccc agtttaaatt      900 ttttttttt tttaatttca ttatccttct tttcccctttt tggtcgacag ttggaatctc      960
tctcgttttc cgtttcgcag acgacttcga gaacatcctt gaccgactgg tcggtttcac    1020
ggcttgcatt cgtgggagtc acgcccgaca taaccagcac actagaagaa aaccagattc    1080
acacgggaaa cggggataga ttacttgctt gacgcaagca cttccccata gcgttgattt    1140
tgtttggttg gaccgaggga ttgccaagta agtcccaagc ttcattgcta gctggtcatt    1200
atttgatctc gaccatgaaa ttgtggtcaa ttacgcccgt cgaatcttgt tgtgctaatc    1260
ctggcagttt ttcgcatcac agtcaaggcg tctctgcctc aaacaatgct cttcacccctc   1320 ttcgcgggtc tgaaataccc tcacctggca acagcaattg gcgcttcatg gctgttttc     1380 cgatctctct acttgtacgg ctatgtgtac tcgggtaagc cacaaggcaa gggcagattg    1440
ctgggaggtt tcttctggtt ttctcaaggc gctctgtggg ctctgagtgt gtttggtgtt    1500
gccaaagaca tgatctctta ctgagagtta ttctgtgtct gacgaaatat gttgtgtata    1560
```

```
tatatatatg tacgttaaaa gttccgtgga gttaccagtg attgaccaat gttttatctt   1620
ctacagttct gcctgtctac cccattctag ctgtacctga ctacagagta gtttaattgt   1680
ggttgacccc acagtcggag gcggaggaat acagcaccga tgtggcctgt ctccatccag   1740
attggcacgc aatttttaca cgcggaaaag atcgagatag agtacgactt taaatttagt   1800
ccccggcggc ttctatttta gaatatttga gatttgattc tcaagcaatt gatttggttg   1860
ggtcaccctc aattggataa tatacctcat tgctcggcta cttcaactca tcaatcaccg   1920 tcatacccccg catataaccc tccattccca cgatgtcgtc caagtcgcaa ttgacttacg   1980
gtgctcgagc cagcaagcac cccaatcctc tggcaaagag acttttttgag attgccgaag   2040 caaagaagac aaacgttacc gtctctgctg atgtgacgac aacccgagaa ctcctggacc   2100
tcgctgaccg tacggaagct gttggatcca atacatatgc cgtctagcaa tggactaatc   2160 aactttgat gatacaggtc tcggtccta catcgccgtc atcaagacac acatcgacat   2220
cctcaccgat ttcagcgtcg acactatcaa tggcctgaat gtgctggctc aaaagcacaa   2280 cttttgatc ttcgaggacc gcaaattcat cgacatcggc aataccgtcc agaagcaata   2340
ccacggcggt gctctgagga tctccgaatg ggcccacatt atcaactgca gcgttctccc   2400
tggcgagggc atcgtcgagg ctctggccca gaccgcatct gcgcaagact tcccctatgg   2460
tcctgagaga ggactgttgg tcctggcaga gatgacctcc aaaggatcgc tggctacggg   2520
cgagtatacc aaggcatcgg ttgactacgc tcgcaaatac aagaacttcg ttatgggttt   2580
cgtgtcgacg cgggccctga cggaagtgca gtcggatgtg tcttcagcct cggaggatga   2640
agatttcgtg gtcttcacga cgggtgtgaa cctctcttcc aaaggagata agcttggaca   2700
gcaataccag actcctgcat cggctattgg acgcggtgcc gactttatca tcgccggtcg   2760
aggcatctac gctgctcccg acccggttga agctgcacag cggtaccaga agaaggctg   2820 ggaagcttat atggccagag tatgcggcaa gtcatgattt cctcttggag caaaagtgta   2880
gtgccagtac gagtgttgtg gaggaaggct gcatacattg tgcctgtcat taaacgatga   2940
gctcgtccgt attggcccct gtaatgccat gttttccgcc cccaatcgtc aaggttttcc   3000
ctttgttaga ttcctaccag tcatctagca agtgaggtaa gctttgccag aaacgccaag   3060
gctttatcta tgtagtcgat aagcaaagtg gactgatagc ttaatatgga aggtccctca   3120
ggacaagtcg acctgtgcag aagagataac agcttggcat cacgcatcag tgcctcctct   3180
cagacagaat aagtcgccat aagttatcga ccgaacctag gtagggtata tttggtgacg   3240 acaataccctc ccgacgatac ctgggttgat tcctgctttt cctcccgctc ataggacg   3300 gcgtcttggc gaacggtcgt cgattgattt cttcccgta atctgttcct tttcctaatg   3360
tactctggtg tgatgggctt cagggactct tttaacgacc cagactttg atgtttatac   3420 caccgttctt tttcttcttt cctcgatctt tggcattatt gtacatgatg ctctgcatgt   3480
ggttttcaag atattcccg gattgttctt gtcttcagtt tatatacggc cgctctcgtg   3540
tttattatcc gctgtgtttc caggtcggct ggacctgggg cctctccctt cccgcgaata   3600
gaagtgagtg agcaatacaa atgtgacatt gtccaaaagt ttggtgatct gaacgcgcaa   3660
cctggatgca ttgatccgag acaatcacgg ggtcttagac atgcgacatg tctgattcac   3720
tccttcgacc atttccttgt ttatccatga ccatgcccca tccactggca tgcgagaatg   3780
acgtatgcga cagataagat cgacgatctg cctatatat ccgaattgat tcgattgtca   3840
atactctctc ttagtgttgt ataagtatat atatgtgctg tagagtatgt cctggctgtc   3900
```

| | |
|---|---|
| tcccatacag aagaagccat gtcgagaaag ggtatgtcca ccagagtaag attgtacatt | 3960 |
| ccttggacat gtcattgtca tttcacagga aatatcgaag ggtcatggat tcggaggaac | 4020 |
| attccaggaa gagacaccag aaatgagttg gcacggatca gtaaacatgt agatctacat | 4080 |
| aaccttgttc attttcatga tgcactgaca ctagagcata gaggcgttta ctttacctct | 4140 |
| tatcaacgac taattgacat aaccaagcag tggaattttt atgattcaac gtcccagact | 4200 |
| atagtgccta ctgttatgat ctacctgcta ctttgatcgg tttcactttc tttgttggtt | 4260 |
| gatacttgtt gcgtatcttc tttgattact tatagtcaat agtccctgtt actatattag | 4320 |
| cgccgttcct agccattgta tatcctttga tccactactt gaaagaaaat tcgaacaagg | 4380 |
| gttttaatgg atgtatccat tctatttttct cttttctttg gatgtaatga gatacaaagg | 4440 |
| tgttctaatc aaaaagtatg tattcaattc aaatacatct tcccagacaa tctgggaaga | 4500 |
| ggaataagca agagagataa ttctccgact cacactattc gccatatcaa gaccccc | 4556 |

<210> SEQ ID NO 143
<211> LENGTH: 9329
<212> TYPE: DNA
<213> ORGANISM: Artificial Sequence
<220> FEATURE:
<223> OTHER INFORMATION: Aspergillus flavus multicopy veA strain with
      Aspergillus fumigatus pyrG in TOPO-TA cloning plasmid

<400> SEQUENCE: 143

| | |
|---|---|
| agcgcccaat acgcaaaccg cctctccccg cgcgttggcc gattcattaa tgcagctggc | 60 |
| acgacaggtt tcccgactgg aaagcgggca gtgagcgcaa cgcaattaat gtgagttagc | 120 |
| tcactcatta ggcaccccag gctttacact ttatgcttcc ggctcgtatg ttgtgtggaa | 180 |
| ttgtgagcgg ataacaattt cacacaggaa acagctatga ccatgattac gccaagcttg | 240 |
| gtaccgagct cggatccact agtccgcctg cccttaacct ccagctggct gagttcccac | 300 |
| tggatcggcc attcttcttt ttttaccccc tcttctgtga caccatccac cttcccccat | 360 |
| tttagtgcca tccgtgctga cccaataccc accatatcgg ctcagtcgtg cagagttagt | 420 |
| gccgtcgtac ataccagctc cattagaagg tactgtacat acgccatgta tctacgggt | 480 |
| aattccggtt gccgtcgtca gaacggataa acatctccta ttgaccctct cgataagaaa | 540 |
| gagcaagttc agagcgaata aaatgctcga agcgcagaaa tgcgaccgta gacccatggt | 600 |
| accgggatat ttaagaacgc aagttatgta tggggccgtc agcccgatca ccatgttgtt | 660 |
| ggaacttgga accgatggaa accgtcaccg tcggtaatct tacagtacca cggctccgga | 720 |
| gacgagacgt ttagggtgtt atagttggtt gcgatagtgt gtgtacctgc cgattctcag | 780 |
| gctgactcgt cctttgactt ttcccgtcct cgctcgctcc accccctctc attcattatt | 840 |
| cttcgtcccc cccgtatcac caacttgact tttgttactc ctctcccata ccttctttcc | 900 |
| tcatcctgga cgggtcaatc gctggattgt ctgttgtact gcctcggcgc agcggaccca | 960 |
| gtttaaattt tttttttttt ttaatttcat tatccttctt ttccccttt ggtcgacagt | 1020 |
| tggaatctct ctcgttttcc gtttcgcaga cgacttcgag aacatccttg accgactggt | 1080 |
| cggtttcacg gcttgcattc gtgggagtca cgcccgacat aaccagcaca ctagaagaaa | 1140 |
| accagattca cacgggaaac ggggatagat tacttgcttg acgcaagcac tttcccatag | 1200 |
| cgttgatttt gtttggttgg accgagggat tgccaagtaa gtcccaagct tcattgctag | 1260 |
| ctggtcatta tttgatctcg accatgaaat tgtggtcaat tacgcccgtc gaatcttgtt | 1320 |
| gtgctaatcc tggcagtttt tcgcatcaca gtcaaggcgt ctccaaaatg gcgacacgag | 1380 |

```
ctcctttggc gcctccgccg aacgagacgg aagcctccgt cagccggatc actcgagagg    1440
gcaagaagct cacctataaa ctcaatgtca tgcaacagcc tgagcgtgcg cgagcctgcg    1500
gtgcaggtgc aaagtgtatg cgtccaacca gcactccata accggatagc atcaaactga    1560
tggttctgac tttatatagc ctctgcggac cgtcgtccag tcgatcctcc accggtcgtc    1620
gaacttcgag tgtacgagtc cgatcccaac gacgacctca acaagaccga catcaccttc    1680
gcatacaacg ccaatttctt cctgtacgcc actttggaaa ccgctcgtcc catgcccaa    1740 ggccgttttg ccccgaatcc gacttgccca gtattgaccg gtgtgcccgt ggctggagtg    1800
gcttacttgg accgcccttc tcaagccggt tacttcatct tccccgatct ttccgtgcgg    1860
catgaaggtg tatatcgatt gaacttccac ctgtacgagg aaaccaagga gagcaaggat    1920
gcgaacgaga atgctccgat ccagtccctg tccaacccaa tgccatcgaa gccgatggcg    1980
ccgaagtcat tcctggagtt tcgtctcgag gtcgtttccg ttccgttcac cgtatttagc    2040
gccaagaagt tcccaggatt ggccacgagt acctccctga gtcgggtcat tgcggagcaa    2100
ggttgtcgtg tgcggattcg acgtgatgtc cgcatgagac gtcggggaga gaagcgcacc    2160
gatgactacg actacgatga ggagagagtc taccgatctt ctgaccgaat ctctaccca    2220 gatacccacg ggtacgccgg cactcccgtt gaacgtcctc gatcaaccag taccagcacg    2280
gtggatccct cattccccta cggtgtcgat gctcagcgcc ggtcatctgg cgcgaccgag    2340
tatggtttcc agggtgcaca gccgtaccaa cgaccattgc cgcctgctcc cggtcccgca    2400
ccagccgctg tttccacgcc cgctcctccc gctcctcccg cgccaccatc ccataatcct    2460
ggatatcaat cgcatctttc ctttggctcg actcaaactc aatatccagc tccccaactg    2520
cctccaactc cacagaccgc gtcgacattg gcagctccgt actcgcccca tccatcgtat    2580
tctcatgctc ggaatccatc gacgagcgcc gagtatgaaa cgcccggtta ctcctatccg    2640
ccatcacgga tgtcaacgga acgttccagc tatcccaaga atggcttgcc tccgctccgc    2700
ttggaaccgc taagccact aaatatgcca tccggcgagc cacgctcgtc cgatccgaac    2760
gcatatcatt ccgtggctca atcggcggca ccccggtctc agacaccgtc atccagtctg    2820
gtgccttccc ttccgcccct caaggctcta tcggggatt atcccaacaa cctctctcaa    2880
tcatccagca gtacctctca gagccccagt cacgatctcg gcgctggcaa gaagttcttc    2940
tgggatacgg gcgccagcct gtccaagcgg tcgtacgaag attcgtttgg ccatgatgat    3000
cgtccactct acaacggcat gcgccccgat acggaaagtt atcctcggag gctgtcagat    3060
gccagtcgga acttctacaa cgaaacgcgc gatgaaatgg cgtacaaacg agccaacggg    3120
agaatggcca cgaagatatc ccctgcactc cagtaaaaca agttgattcc tgcttttcct    3180
cccgctcata taggacggcg tcttggcgaa cggtcgtcga ttgatttctt tcccgtaatc    3240
tgttcctttt cctaatgtac tctggtgtga tgggcttcag ggactctttt aacgacccag    3300
acttttgatg tttataccac cgttcttttt cttctttcct cgatctttgg cattattgta    3360
catgatgctc tgcatgtggt tttcaagata ttccccggat tgttcttgtc ttcagtttat    3420
atacggccgc tctcgtgttt attatccgct gtgtttccag gtcggctgga cctggggcct    3480
ctcccttccc gcgaatagaa gtgagtgagc aatacaaatg tgacattgtc caaaagtttg    3540
gtgatctgaa cgcgcaacct ggatgcattg atccgagaca atcacggggt cttagacatg    3600
cgacatgtct gattcactcc ttcgaccatt tccttgttta tccatgacca tgccccatcc    3660
actggcatgc gagactagta acggccgcca gtgtgctggg cccttccagg tatcgtcggg    3720
aggtattgtc gtcaccaaat atccctacc taggttcggt cgataactta tggcgactta    3780
```

```
ttctgtctga gaggaggcac tgatgcgtga tgccaagctg ttatctcttc tgcacaggtc    3840
gacttgtcct gagggacctt ccatattaag ctatcagtcc actttgctta tcgactacat    3900
agataaagcc ttggcgtttc tggcaaagct tacctcactt gctagatgac tggtaggaat    3960
ctaacaaagg gaaaaccttg acgattgggg gcggaaaaca tggcattaca ggggccaata    4020
cggacgagct catcgtttaa tgacaggcac aatgtatgca gccttcctcc acaacactcg    4080
tactggcact acacttttgc tccaagagga aatcatgact tgccgcatac tctggccata    4140
taagcttccc agccttcttt ctggtaccgc tgtgcagctt caaccgggtc gggagcagcg    4200
tagatgcctc gaccggcgat gataaagtcg gcaccgcgtc caatagccga tgcaggagtc    4260
tggtattgct gtccaagctt atctcctttg aagagaggt tcacacccgt cgtgaagacc     4320
acgaaatctt catcctccga ggctgaagac acatccgact gcacttccgt cagggcccgc    4380
gtcgacacga aacccataac gaagttcttg tatttgcgag cgtagtcaac cgatgccttg    4440
gtatactcgc ccgtagccag cgatcctttg gaggtcatct ctgccaggac caacagtcct    4500
ctctcaggac catagggaa gtcttgcgca gatgcggtct gggccagagc ctcgacgatg     4560
ccctcgccag ggagaacgct gcagttgata atgtgggccc attcggagat cctcagagca    4620
ccgccgtggt attgcttctg gacggtattg ccgatgtcga tgaatttgcg gtcctcgaag    4680
atcaaaaagt tgtgcttttg agccagcaca ttcaggccat tgatagtgtc gacgctgaaa    4740
tcggtgagga tgtcgatgtg tgtcttgatg acggcgatgt agggaccgag acctgtatca    4800
tcaaaagttg attagtccat tgctagacgg catatgtatt ggatccaaca gcttccgtac    4860
ggtcagcgag gtccaggagt tctcgggttg tcgtcacatc agcagagacg gtaacgtttg    4920
tcttctttgc ttcggcaatc tcaaaaagtc tctttgccag aggattgggg tgcttgctgg    4980
ctcgagcacc gtaagtcaat tgcgacttgg acgacatcgt gggaatggag ggttatatgc    5040
ggggtatgac ggtgattgat gagttgaagt agccgagcaa tgaggtatat tatccaattg    5100
agggtgaccc aaccaaatca attgcttgag aatcaaatct caaatattct aaaatagaag    5160
ccgccgggga ctaaatttaa agtcgtactc tatctcgatc ttttccgcgt gtaaaaattg    5220
cgtgccaatc tggatggaga caggccacat cggtgctgta ttcctccgcc tccgactgtg    5280
gggtcaacca caattaaact actctgtagt caggtacagc tagaatgggg tagacaggca    5340
gaactgtaga agataaaaca ttggtcaatc actggtaact ccacggaact tttaacgtac    5400
atatatatat atacacaaca tatttcgtca gacacagaat aactctcagt aagagatcat    5460
gtctttggca acaccaaaca cactcagagc ccacagagcg ccttgagaaa accagaagaa    5520
acctcccagc aatctgccct tgccttgtgg cttacccgag tacacatagc cgtacaagta    5580
gagagatcgg aaaacagcc atgaagcgcc aattgctgtt gccaggtgag ggtatttcag     5640
acccgcgaag agggtgaaga gcattgtttg aggcaaaggg caattcgccc ttaagggcga    5700
attctgcaga tatccatcac actggcgccc gctcgagcat gcatctagag ggcccaattc    5760
gccctatagt gagtcgtatt acaattcact ggccgtcgtt ttacaacgtc gtgactggga    5820
aaaccctggc gttacccaac ttaatcgcct tgcagcacat ccccctttcg ccagctggcg    5880
taatagcgaa gaggcccgca ccgatcgccc ttcccaacag ttgcgcagcc tgaatggcga    5940
atggacgcgc cctgtagcgg cgcattaagc gcggcgggtg tggtggttac gcgcagcgtg    6000
accgctacac ttgccagcgc cctagcgccc gctccttttcg ctttcttccc ttcctttctc   6060
gccacgttcg ccggctttcc ccgtcaagct ctaaatcggg ggctcccttt agggttccga    6120
```

```
tttagtgctt tacggcacct cgaccccaaa aaacttgatt agggtgatgg ttcacgtagt    6180
gggccatcgc cctgatagac ggttttcgc cctttgacgt tggagtccac gttctttaat    6240
agtggactct tgttccaaac tggaacaaca ctcaaccta tctcggtcta ttcttttgat    6300
ttataaggga ttttgccgat ttcggcctat tggttaaaaa atgagctgat ttaacaaaaa    6360
tttaacgcga attttaacaa aattcagggc gcaagggctg ctaaaggaag cggaacacgt    6420
agaaagccag tccgcagaaa cggtgctgac cccggatgaa tgtcagctac tgggctatct    6480
ggacaaggga aaacgcaagc gcaaagagaa agcaggtagc ttgcagtggg cttacatggc    6540
gatagctaga ctgggcggtt ttatggacag caagcgaacc ggaattgcca gctgggcgc    6600 cctctggtaa ggttgggaag ccctgcaaag taaactggat ggctttcttg ccgccaagga    6660
tctgatggcg caggggatca agatctgatc aagagacagg atgaggatcg tttcgcatga    6720
ttgaacaaga tggattgcac gcaggttctc cggccgcttg ggtggagagg ctattcggct    6780
atgactgggc acaacagaca atcggctgct ctgatgccgc cgtgttccgg ctgtcagcgc    6840
aggggcgccc ggttcttttt gtcaagaccg acctgtccgg tgccctgaat gaactgcagg    6900
acgaggcagc gcggctatcg tggctggcca cgacgggcgt tccttgcgca gctgtgctcg    6960
acgttgtcac tgaagcggga agggactggc tgctattggg cgaagtgccg gggcaggatc    7020
tcctgtcatc ccaccttgct cctgccgaga aagtatccat catggctgat gcaatgcggc    7080
ggctgcatac gcttgatccg gctacctgcc cattcgacca ccaagcgaaa catcgcatcg    7140
agcgagcacg tactcggatg gaagccggtc ttgtcgatca ggatgatctg gacgaagagc    7200
atcaggggct cgcgccagcc gaactgttcg ccaggctcaa ggcgcgcatg cccgacggcg    7260
aggatctcgt cgtgacccat ggcgatgcct gcttgccgaa tatcatggtg gaaaatggcc    7320
gcttttctgg attcatcgac tgtggccggc tgggtgtggc ggaccgctat caggacatag    7380
cgttggctac ccgtgatatt gctgaagagc ttggcggcga atgggctgac cgcttcctcg    7440
tgctttacgg tatcgccgct cccgattcgc agcgcatcgc cttctatcgc cttcttgacg    7500
agttcttctg aattgaaaaa ggaagagtat gagtattcaa catttccgtg tcgcccttat    7560 tcccttttt gcggcatttt gccttcctgt ttttgctcac ccagaaacgc tggtgaaagt    7620
aaaagatgct gaagatcagt tgggtgcacg agtgggttac atcgaactgg atctcaacag    7680
cggtaagatc cttgagagtt ttcgccccga agaacgtttt ccaatgatga gcacttttaa    7740
agttctgcta tgtggcgcgg tattatcccg tattgacgcc gggcaagagc aactcggtcg    7800
ccgcatacac tattctcaga atgacttggt tgagtactca ccagtcacag aaaagcatct    7860
tacggatggc atgacagtaa gagaattatg cagtgctgcc ataaccatga gtgataacac    7920
tgcggccaac ttacttctga caacgatcgg aggaccgaag gagctaaccg cttttttgca    7980
caacatgggg gatcatgtaa ctcgccttga tcgttggaa ccggagctga atgaagccat    8040
accaaacgac gagcgtgaca ccacgatgcc tgtagcaatg gcaacaacgt tgcgcaaact    8100
attaactggc gaactactta ctctagcttc ccggcaacaa ttaatagact ggatggaggc    8160
ggataaagtt gcaggaccac ttctgcgctc ggcccttccg gctggctggt ttattgctga    8220
taaatctgga gccggtgagc gtgggtctcg cggtatcatt gcagcactgg ggccagatgg    8280
taagccctcc cgtatcgtag ttatctacac gacggggagt caggcaacta tggatgaacg    8340
aaatagacag atcgctgaga taggtgcctc actgattaag cattggtaac tgtcagacca    8400
agtttactca tatatacttt agattgattt aaaacttcat ttttaattta aaaggatcta    8460
ggtgaagatc cttttgata atctcatgac caaaatccct taacgtgagt ttcgttcca    8520
```

```
ctgagcgtca gaccccgtag aaaagatcaa aggatcttct tgagatcctt tttttctgcg    8580
cgtaatctgc tgcttgcaaa caaaaaaacc accgctacca gcggtggttt gtttgccgga    8640
tcaagagcta ccaactcttt ttccgaaggt aactggcttc agcagagcgc agataccaaa    8700
tactgttctt ctagtgtagc cgtagttagg ccaccacttc aagaactctg tagcaccgcc    8760
tacatacctc gctctgctaa tcctgttacc agtggctgct gccagtggcg ataagtcgtg    8820
tcttaccggg ttggactcaa gacgatagtt accggataag gcgcagcggt cgggctgaac    8880 gggggggttcg tgcacacagc ccagcttgga gcgaacgacc tacaccgaac tgagatacct    8940
acagcgtgag ctatgagaaa gcgccacgct tcccgaaggg agaaaggcgg acaggtatcc    9000
ggtaagcggc agggtcggaa caggagagcg cacgagggag cttccagggg gaaacgcctg    9060
gtatctttat agtcctgtcg ggtttcgcca cctctgactt gagcgtcgat ttttgtgatg    9120
ctcgtcaggg gggcggagcc tatggaaaaa cgccagcaac gcggcctttt tacggttcct    9180
ggccttttgc tggccttttg ctcacatgtt ctttcctgcg ttatccctg attctgtgga     9240 taaccgtatt accgcctttg agtgagctga taccgctcgc cgcagccgaa cgaccgagcg    9300
cagcgagtca gtgagcgagg aagcggaag                                      9329

<210> SEQ ID NO 144
<211> LENGTH: 7814
<212> TYPE: DNA
<213> ORGANISM: Artificial Sequence
<220> FEATURE:
<223> OTHER INFORMATION: Aspergillus flavus laeA knockout with
      Aspergillus fumigatus pyrG

<400> SEQUENCE: 144
gggcgaattg ggcccgacgt cgcatgctcc cggccgccat ggccgagacc tactagttaa      60
tagctccgat cgagtgatac gtaccatcct catgccagac ctctcccagc taggtatcga     120
cttagaaccc gccaacatca agcttcaggt cgaacataag ttccaggacg tagtcaacag     180
actaagttgg aaccatgtca catttttcttc aacgagtgaa ttcgtcaccg catccacctt    240
catgaaccct gacatttacg tttgggaacg gagtcacggt tccctggtga agatcctcga    300
gggtcctaga gaagaactgg gcgtcgtgga atggcaccct tctcgcccta tggttgtcgc    360
ttgcggttta gaatctggat gcatctacac atggtcgatt gtgacgcctc aaaaatggtc    420
cgcgctggca cctgattttg gtgaagtcga ggaaaacgtc gagtatgttg agcgcgaaga    480
cgaatttgac gttcaccctg ccgaagaaat tcaccaacgc cggcttgacc aggaagacga    540
agttcctgac gtattaacga tcgagcccca caaaagcggt acggatgagg agatggaatc    600
cttccgcatg cctgtgcttc tagatatttc tgacagcgaa agtgaagagg acatcattgc    660
cgtcggtccc ggaacaatgc ggaggcgtag ccccggcgct ggccgtgact gggccagcgg    720
agatggtgag aaagaaagta ctggaggtag aaacggtacc tcccggggac aaaagggccg    780
ccggcgttaa agtgatatca ttgtatgagt tcacattata gtattagata atttacagga    840
gcatctgtct tgggtcattg ggtgggcggg tgtcttgaag gctatcgagg cgttttggcg    900
aaatacccaa agactggtat ctcacacact tgcatttccg gttcatgtta gctggtagtg    960
agaccttaca aacgatcaca tggataaaat tctttgcatt gtattatata aattttata    1020 ttcttttta agtgatatcat gttatgaatc tcgaatatag caataaccat gattggatga    1080
tgtcgtcaca gatagaatga actaaaccgg gtatacagtt atcaacatta cactcaccca    1140
aaacgccata aatatgctgt ctttggcaag cgggaaagca tgcaatgcca gggaatgatg    1200
```

```
tggtcctgaa gtgtgatgaa ggagccacag ccaggttaag agcaggcaga gggcagaggg    1260
cagagggcat gccatgccgt gtcctattaa tgacctgcca gtattctgca gcccattgg     1320 ttcgtccata ggggcaagag ctgcatcgcg atgtattttt tggacgaaat gatctttgac    1380
ttgcctgttt ggcctgggta atttgtataa ccccctttcgc aagacgtacg cccgcctcat   1440
gctcggacct atgataatca aagcaaactc tgtatatttc catcaacctt ctaagtgcta    1500
ctggagtgat acaggcagct cagtgcatcg tcgggatagg cgttaattcg cggcatacgg    1560
tgtctaatcc aggtatcgtc gggaggtatt gtcgtcacca aatataccct acctaggttc    1620
ggtcgataac ttatggcgac ttattctgtc tgagaggagg cactgatgcg tgatgccaag    1680
ctgttatctc ttctgcacag gtcgacttgt cctgagggac cttccatatt aagctatcag    1740
tccactttgc ttatcgacta catagataaa gccttggcgt ttctggcaaa gcttacctca    1800
cttgctagat gactggtagg aatctaacaa agggaaaacc ttgacgattg ggggcggaaa    1860
acatggcatt acaggggcca atacggacga gctcatcgtt taatgacagg cacaatgtat    1920
gcagccttcc tccacaacac tcgtactggc actacacttt tgctccaaga ggaaatcatg    1980
acttgccgca tactctggcc atataagctt cccagccttc tttctggtac cgctgtgcag    2040
cttcaaccgg gtcgggagca gcgtagatgc ctcgaccggc gatgataaag tcggcaccgc    2100
gtccaatagc cgatgcagga gtctggtatt gctgtccaag cttatctcct ttggaagaga    2160
ggttcacacc cgtcgtgaag accacgaaat cttcatcctc cgaggctgaa gacacatccg    2220
actgcacttc cgtcagggcc cgcgtcgaca cgaaacccat aacgaagttc ttgtatttgc    2280
gagcgtagtc aaccgatgcc ttggtatact cgcccgtagc cagcgatcct ttggaggtca    2340
tctctgccag gaccaacagt cctctctcag gaccataggg gaagtcttgc gcagatgcgg    2400
tctgggccag agcctcgacg atgccctcgc cagggagaac gctgcagttg ataatgtggg    2460
cccattcgga gatcctcaga gcaccgccgt ggtattgctt ctggacggta ttgccgatgt    2520
cgatgaattt gcggtcctcg aagatcaaaa agttgtgctt ttgagccagc acattcaggc    2580
cattgatagt gtcgacgctg aaatcggtga ggatgtcgat gtgtgtcttg atgacggcga    2640
tgtagggacc gagacctgta tcatcaaaag ttgattagtc cattgctaga cggcatatgt    2700
attggatcca acagcttccg tacggtcagc gaggtccagg agttctcggg ttgtcgtcac    2760
atcagcagag acgtaacgt ttgtcttctt tgcttcggca atctcaaaaa gtctctttgc     2820
cagaggattg gggtgcttgc tggctcgagc accgtaagtc aattgcgact tggacgacat    2880
cgtgggaatg gagggttata tgcggggtat gacggtgatt gatgagttga agtagccgag    2940
caatgaggta tattatccaa ttgagggtga cccaaccaaa tcaattgctt gagaatcaaa    3000
tctcaaatat tctaaaatag aagccgccgg ggactaaatt taaagtcgta ctctatctcg    3060
atcttttccg cgtgtaaaaa ttgcgtgcca atctggatgg agacaggcca catcggtgct    3120
gtattcctcc gcctccgact gtggggtcaa ccacaattaa actactctgt agtcaggtac    3180
agctagaatg gggtagacag gcagaactgt agaagataaa acattggtca atcactggta    3240
actccacgga acttttaacg tacatatata tatatacaca acatatttcg tcagacacag    3300
aataactctc agtaagagat catgtctttg gcaacaccaa acacactcag agcccacaga    3360
gcgccttgag aaaaccagaa gaaacctccc agcaatctgc ccttgccttg tggcttaccc    3420
gagtacacat agccgtacaa gtagagagat cggaaaaaca gccatgaagc gccaattgct    3480
gttgccaggt gagggtattt cagacccgcg aagagggtga agagcattgt ttgaggcaat    3540
```

-continued

```
cactagtggc cgcgtagtac gagtcgtgtg gtggtgaggc catcgccgga agacgctgtc   3600
cagtctggcc gtttccaaac attccgtgtg gtgaagaagg gtcggtaaga agtttggtac   3660
tttaagatgg tgacgagggg aagaatgccg acgtcgatgg cgacaagctg atgtcagtag   3720
cgtggacgct tgtaggttgt gtatatggta tatatattga gtgacgaata aaacatagag   3780
tagaatgggg ctgagcctag tgaatggacg gcaagttcat tcataaattt aagggagtga   3840
aaagcgaaac acaagatatc attcgcagta ttagaaagag agacgaggat tcaggggag    3900 aatcagaaaa gtaaacagag aaaataaga aaagaaaaga aaaaaaatt aaaatcaaaa     3960 atcaaaaatc aaaatcaga atctaaaaaa ataagaaaag ttggagatag gaccaggcag    4020
agaatcaaag gtcacgtcca cttaaacaca gaagggcaga aacggaaaaa ccaagacggt   4080
gaccagccaa aagtaccgac aggcaaagag ataataatag agaacgccgt gctgtctccc   4140
cgcgatgaag cgatgccagt cgggaaatcc acagaagaag tagcggtcac ggcgcaagca   4200
atcactgggc gcaaatcgtc aacaacggac aggagttgtc acggctaacc atggatgggt   4260
ggtcgatcca aggtcatcaa ttgggacgaa ttcacccagc accataccat ggaaaagaag   4320
attaatgagc ggagccctga gggggcgaga attggtagtg gtggacgagg gggaagcgag   4380
aagaagccct gtaatggaaa gcctgccttt aaggttgttg cagccgctgt cttgtccccg   4440
ttgggcccac ggctgcgagg gcggggcggt taaggaagaa gcctgaggct gtccttgcac   4500
tgtccggtaa gtatcctttc gtaatactct ttttctttcc ctctttcctc tctccttttcc  4560 agcagaagat gggcgtaagc aacgctggga tgtatgagca tgccctctat ttgtgtgtta   4620
tttgacagtt caacgaacta atcgccttaa ataaatgtat ccgacaacag agtgtcgatt   4680
tagagaaggt gttgtggttg gtatcccatc ggatttattg gctggagagg ttaaaactgc   4740
ccctccataa accatggtat atcccctaat tagtacctgt ccgtcatcaa caaccctaca   4800
tggattatct tttagtggtt actagtctta aaaagactct ggtagcgccc attcaaccta   4860
tccatggatc ttgaacagcc ggttgcacaa cttggatata atctaggtat gttgtattca   4920
tgtacatata tactgtattc tatagtgtca cctaaatagc ttggcgtaat catggtcata   4980
gctgtttcct gtgtgaaatt gttatccgct cacaattcca cacaacatac gagccggaag   5040
cataaagtgt aaagcctggg gtgcctaatg agtgagctaa ctcacattaa ttgcgttgcg   5100
ctcactgccc gctttccagt cgggaaacct gtcgtgccag ctgcattaat gaatcggcca   5160
acgcgcgggg agaggcggtt tgcgtattgg gcgctcttcc gcttcctcgc tcactgactc   5220
gctgcgctcg gtcgttcggc tgcggcgagc ggtatcagct cactcaaagg cggtaatacg   5280
gttatccaca gaatcagggg ataacgcagg aaagaacatg tgagcaaaag gccagcaaaa   5340
ggccaggaac cgtaaaaagg ccgcgttgct ggcgtttttc cataggctcc gcccccctga   5400
cgagcatcac aaaaatcgac gctcaagtca gaggtggcga aacccgacag gactataaag   5460
ataccaggcg tttccccctg gaagctccct cgtgcgctct cctgttccga ccctgccgct   5520
taccggatac ctgtccgcct ttctcccttc gggaagcgtg gcgctttctc atagctcacg   5580
ctgtaggtat ctcagttcgg tgtaggtcgt tcgctccaag ctgggctgtg tgcacgaacc   5640
ccccgttcag cccgaccgct gcgccttatc cggtaactat cgtcttgagt ccaacccggt   5700
aagacacgac ttatcgccac tggcagcagc cactggtaac aggattagca gagcgaggta   5760
tgtaggcggt gctacagagt tcttgaagtg gtggcctaac tacggctaca ctagaagaac   5820
agtatttggt atctgcgctc tgctgaagcc agttaccttc ggaaaaagag ttggtagctc   5880
ttgatccggc aaacaaacca ccgctggtag cggtggtttt tttgtttgca agcagcagat   5940
```

```
tacgcgcaga aaaaaaggat ctcaagaaga tcctttgatc tttctacgg ggtctgacgc    6000 tcagtggaac gaaaactcac gttaagggat tttggtcatg agattatcaa aaaggatctt    6060
cacctagatc cttttaaatt aaaaatgaag ttttaaatca atctaaagta tatatgagta    6120
aacttggtct gacagttacc aatgcttaat cagtgaggca cctatctcag cgatctgtct    6180
atttcgttca tccatagttg cctgactccc cgtcgtgtag ataactacga tacgggaggg    6240
cttaccatct ggccccagtg ctgcaatgat accgcgagac ccacgctcac cggctccaga    6300
tttatcagca ataaccagc cagccggaag ggccgagcgc agaagtggtc ctgcaacttt      6360
atccgcctcc atccagtcta ttaattgttg ccgggaagct agagtaagta gttcgccagt    6420
taatagtttg cgcaacgttg ttgccattgc tacaggcatc gtggtgtcac gctcgtcgtt    6480
tggtatggct tcattcagct ccggttccca acgatcaagg cgagttacat gatcccccat    6540
gttgtgcaaa aaagcggtta gctccttcgg tcctccgatc gttgtcagaa gtaagttggc    6600
cgcagtgtta tcactcatgg ttatggcagc actgcataat tctcttactg tcatgccatc    6660
cgtaagatgc ttttctgtga ctggtgagta ctcaaccaag tcattctgag aatagtgtat    6720
gcggcgaccg agttgctctt gcccggcgtc aatacgggga ataccgcgc cacatagcag     6780 aactttaaaa gtgctcatca ttggaaaacg ttcttcgggg cgaaaactct caaggatctt    6840
accgctgttg agatccagtt cgatgtaacc cactcgtgca cccaactgat cttcagcatc    6900
ttttactttc accagcgttt ctgggtgagc aaaaacagga aggcaaaatg ccgcaaaaaa    6960
gggaataagg gcgacacgga aatgttgaat actcatactc ttccttttc aatattattg      7020 aagcatttat cagggttatt gtctcatgag cggatacata tttgaatgta tttagaaaaa    7080
taaacaaata ggggttccgc gcacatttcc ccgaaaagtg ccacctgatg cggtgtgaaa    7140
taccgcacag atgcgtaagg agaaaatacc gcatcaggaa attgtaagcg ttaatatttt    7200
gttaaaattc gcgttaaatt tttgttaaat cagctcattt tttaaccaat aggccgaaat    7260
cggcaaaatc ccttataaat caaaagaata gaccgagata gggttgagtg ttgttccagt    7320
ttggaacaag agtccactat taagaacgt ggactccaac gtcaaagggc gaaaaaccgt      7380
ctatcagggc gatggcccac tacgtgaacc atcccctaa tcaagttttt tggggtcgag      7440
gtgccgtaaa gcactaaatc ggaacccta agggagcccc cgatttagag cttgacgggg     7500
aaagccggcg aacgtggcga gaaaggaagg gaagaaagcg aaaggagcgg gcgctagggc    7560
gctggcaagt gtagcggtca cgctgcgcgt aaccaccaca cccgccgcgc ttaatgcgcc    7620
gctacagggc gcgtccattc gccattcagg ctgcgcaact gttgggaagg gcgatcggtg    7680
cgggcctctt cgctattacg ccagctggcg aaagggggat gtgctgcaag gcgattaagt    7740
tgggtaacgc cagggttttc ccagtcacga cgttgtaaaa cgacggccag tgaattgtaa    7800
tacgactcac tata                                                       7814
```

<210> SEQ ID NO 145
<211> LENGTH: 9453
<212> TYPE: DNA
<213> ORGANISM: Artificial Sequence
<220> FEATURE:
<223> OTHER INFORMATION: Partial sequence of plasmid containing
      Aspergillus parasiticusniaD and Aspergillus flavus laeA

<400> SEQUENCE: 145

```
atggatttcc tacgtcttca atacaaacca tcagacgtcc tggaagctat cattacgtcg     60
cgatcgctta acaagtatga tcgtcttttc aagcatctgc ttcgactcct tcgaatggtt    120
```

```
tcggtcgtca aaggtctcat tcgtgattct acggggagag actccctatc tgggcaccct    180
cgaaacgtgt accagaaatt tcgcattgac tgccagcatt tcgtgctctc attgagtgat    240
tattgctttc atgtcggcat tggctcgact tggcagcggt tccaagatag cctggctaag    300
attgaacgct gcctcgaccg cggtgatatt gatggcacga tagaagcagc acattctgtc    360
cctagactta gagattatca tgaagatatt ctcgatcaaa tgcttttttgc gctctttctc    420 agcaaaagac atgctgatgc agcgaagctg ctggaaagta ttttcggtac gattttgaca    480
tttgctccat tgtcgaggat ggatggaacg agcggcgtgc gccacgaaac tgaggctatt    540
gcctatcagc tctttgctac attccggaaa caaacatccc tttttgtgaa ttatctacgc    600
aacttagatg gcgtgaacgc atcttcaaag tctttcggca ggtccggcac gacttttgca    660
tccagagaag cgcctacatg tgtattcgac cacctcctag cgcgcttgga tatgaggaaa    720
tattactgag agtcgaaaac aagctccacc gcaccagctc ttcttggagt tttatattaa    780
agaatattcc cagctcgttg tattattctt tttctaccgt gctaatgtat caaggacttt    840
ggtacctatt aacgttatta ttcgtgtgct attcccaaac ataaccctgt atatgtttcg    900
aacgccgtta tgacccatgt cttacatact cattaagtca ttcccttgga taatcccaat    960
ttagaagaag tgaaggtctg attctttcca tccttccgcc aacagtatcc tccgagccga   1020
ttcttccatg gctggcggac cacaaatcag gaccatactc tcatcttctg gagccgcgta   1080
ctcctttagg agctcttcgg atatgcgtcc tcggcggcca gtccatgagt ccggcgcttt   1140
ggatagggtg tgtattatat tacaccttct gctgtcggtt gccatgaagc cgtcgagctc   1200
agcccggcaa aggatatctt cctcctgtct gtttccattg aggactgtac aagaggtggg   1260
atcttgccgg tcctgaacca cggcgcgcaa gacctggaag atcggtgtga taccggttcc   1320
tccacaaatc atcttaaacg accgaacatg gcgttccttc ccacttatga caactcgtcc   1380
atttccaagg tattcgaatc tgcctgtcgg acccttgcat tccaccacgg agcccaatgg   1440
cagcctatcc agggccatcg tcatcttgcc gcctgccgag gtggctgttg caaagtatac   1500
tttaaccagc aagtccacgg tccctttctg gctggtttca gaaattgggg tgtatgagcg   1560
gatgatggct tcgttgttgg atgatgtgtc gaggactttg atcataagat gctggccgac   1620
tggtaaaccc aatgtttgat cttcgtgttc caatttgaaa ctaaatattc gtgtatccca   1680
ggatatgtct ttccttttctt tcaatgttgc ctttgtccaa gaccgtgatt ggaggaacac   1740
tgggcgaatt tcatcggtgg aggatgatgc atcatccttg agtgcttttta aaccttccgg   1800 atccatcgtt ccaatatggt actcaggcat catcgccttt gccgtctcgc tatctatgga   1860
taggtgtcaa tagatggtac aattgcagtg tgatatttttt gggactcacg aatagcaagg   1920
aattcctcag agacatccag accagcagag gagataatac tctgcgctcc gccagggtgg   1980
ccttcaagaa atgcttgacc atcatacact tctccattca cgatgaacca tggcttctca   2040
tcgcaggaat tctccttgaa ttcttcaaaa ccaatcactc ggcttagccc gtctttcttc   2100
atattaatgt cttgcacggg ctccggctcc gtcggctcct ctccttcgtg tctttctccc   2160
cagttaccat tcgtcaggtc accccccagcc ttttttgacgc gttccatcca tcctgtaggc   2220
atactagggt gggtagggtg ctcgaatctc aagttcccgt tttccttcgt aattgtaacc   2280
cggaaccacg ggttgttcat cattccgaga acggaccagt acatatcgcg aggctgcacg   2340
cccaatgctt cgtccatggc tcttacaagg atggcatcac tgttctcaag ctctgggatg   2400
gtgatgctta gagaccaaaa acaccagcag aagcaagttt cgcgccagta catatctact   2460
```

```
ttgcctccaa aaagctcgcc ttcaaaatca cgatacttgt cttcggcata ttcgatttcc    2520
gccaatctcc aagctataag tccgttagct ttgataagca ttctcacaca tcgagcgagc    2580
gagggtgcgt acatttgcct ttgtctaggg atatttctac cctggtaacc ctgcggcccc    2640
caccggcgta tgcatatcct ctgacagtat atgacggccc tgcgaccagg agatttaaga    2700
cctcattgtt ttggggatat gcaacggcgg agttggtgtt taggtcataa atcgcatacc    2760
gctcatcgtg ccaccaattt cggttatttg atgccatctc aggcgagacc attgttctgg    2820
gttagggagt tagacaaatg atggaaatat aaaataagtg ccctttagac atacggtaag    2880
acgcggttgt cattgatatg gtaccagttg tcgcttggtg catcggtcaa gatcagcctc    2940
ttcagccact taacacttcg tcctcctatt tgaccgggca cgacggccct cagcggacga    3000
ccatgatctg ggcgaagaga ctccccgttc attttatgtg caagcatgat ccccctgttg    3060
gggtccaggg cccagttcaa tttaatagat gtgccgtagt gaccattggg ctgcggcgaa    3120
cttagcaatt atcatcataa gatagaggta cagcatacca gcttatccgc tccttccata    3180
cagacgtatt tcgctttacg caggggtttc gcactgcgga gaatatccgc cagcaatggg    3240
ccagtgaaga gggcagtcga tagtcccgcc gatccccagg aaaaaccttt cgttttacgt    3300
acattgtttt gctctttgcg tcgattgcca gcacatacga gggtgatagg cgctgttatt    3360
tggtcgtact gctgcaacac ttgtcggaag tttagtacca aaggcttctc taccagtcta    3420
tactttggtt aacggatgtt tggcagagaa cctagcacta tactaaccct tcgatgctaa    3480
tttcccagtg agggatatct tcatccttga tatgagggac tgggccatga tttcgaacat    3540
agaagagctc cggcgatgtt aaaaaccctt tcagagtgtg agaatgtaac ggctcaaggg    3600
gacaagcatg acagccggtg caagcaacct gataaggata ggagtggagc agttataact    3660
cataccttct ttatacagat ctgtgagagg tggctcaaca ttaaacggat gaacacccgt    3720
taatctgata agccgagggt cacgaggaac atggctatct ggagttcctt tatctacgct    3780
cagcacttct gtcggccgtt ttgatggcgg tggcagaggg atatcagaca ggtctctcgt    3840
cgagatctct tcgctttcga ttttgatctg acctgtctta agaacgaggt cagttgggac    3900
gagcgcatcc gtccgcacct cggtgatggt tgccatgtta ccggcaggga aggccaatga    3960
aagtaaaatt acgagggagg gagcatgaac aaggatgctg agtatgaata agtcgaatgg    4020
tcagccagtg cattaactcc aaataaggag gcaatccacc acactaaaat actcttgcct    4080
atcgtatgat ggcacgcagt acgtgttacc catgcgcggg cagtggacat tctattaggt    4140
cacggcagta actccttgtt accatataac gcctcggaga aaggtcacaa taagcaatgc    4200
tcctaggaac ccaccagcga tttccgcgga gtcccaaaat cagctcattc tgggaggtgg    4260
gacgctcgaa attagggcaa gccttcaggc tggacggcgt cccaccgctt aaccaagcgt    4320
tgaggcaaat aaatcgcgtt gacccacaca acactctcga ggctccagcc atttgtccgc    4380
tcaaccttgc aggatttctt tttcgtcata ttaattggtt ctttgaagaa tgatggagac    4440
aatgccgtga agccatgtgc aacttccaat tagaagtgtg gttgcttatc gtccgaatga    4500
gcctggttcg cgtggagaat gggccagatg ggagctcacg gctgttagag cggagctact    4560
actctgtacg taccccttcaa aggaattctc ggtaagtttg ttagagggat attgctcacg    4620
tttaattggc actccaggat cctttaaatc caggcaaaaa tcgctcgatc tggcttttttt   4680
tgccaatctt ggaagtctac cgtatacttg tagttacacc cttgaggatt taccacatga    4740
gaagaacacc aacctaactg cgtgatttaa aacgccattg ctatgatgct tgaagagtgc    4800
cggatatatc ggcatctaac ttaggatttg tcttacgtac aatatttatg acctgtggtg    4860
```

```
aaacctgagg caacaagggg gcgcgattta ccagactggc gttcacatac caatacagtg    4920
cttaattgta ggtctcatgg gtggaatgag atgaccttcc ctttcatcta ttcttaagag    4980
gaacagggat ggtacccaca ccatacccog aagagctcgt gatgtaatag acccotttogt   5040 agtatgcggg ttttttattga gatgccgata tgcaaacttg tagtaagact aataataaca   5100
ggtgcaatta attgaatttg gggcctgtta gcttatcctc cacaaagcct ttcgtaaaat    5160
aactaaccaa ctcaccacta tcagcctaaa tgagtcgatc gaacctccta ccagtaccaa    5220
tctgcttcgt atataataga aggttgtcgg ctccttctga caagacataa tctaatctaa    5280
gatttaactg tggcttttgt gcttaatcga tttatctttt ttatctatct acggagtagt    5340
tattcacgga ttttagctg ataatctagg ctacattttc agactgaatt acgcacaatt     5400
ttggggaagt gagaaaacag acagaaagag gagaaaaaaa agaaaagaa aaaagcatgg     5460 gctaatgtgt gcccactgcc cagacatcta taccttgtat gatgtatgta tgatgagcaa    5520
acataactgt acatacatat accatacata ccctataata cacccatacg gggtatattt    5580
acgtaccttt taggtgtacc cgtatgtata ttgtatgcat gcatgtatat atgtacatga    5640
atacaacata cctagattat atccaagttg tgcaaccggc tgttcaagat ccatggatag    5700
gttgaatggg cgctaccaga gtcttttaa gactagtaac cactaaaaga taatccatgt     5760
agggttgttg atgacggaca ggtactaatt aggggatata ccatggttta tggaggggca    5820
gttttaacct ctccagccaa taaatccgat gggataccaa ccacaacacc ttctctaaat    5880
cgacactctg ttgtcggata catttattta aggcgattag ttcgttgaac tgtcaaataa    5940
cacacaaata gagggcatgc tcatacatcc cagcgttgct tacgcccatc ttctgctgga    6000
aaggagagag gaaagaggga aagaaaaaga gtattacgaa aggatactta ccggacagtg    6060
caaggacagc ctcaggcttc ttccttaacc gccccgccct cgcagccgtg ggcccaacgg    6120
ggacaagaca gcggctgcaa caaccttaaa ggcaggcttt ccattacagg gcttcttctc    6180 gcttcccct cgtccaccac taccaattct cgcccctca gggctccgct cattaatctt      6240
cttttccatg gtatggtgct gggtgaattc gtcccaattg atgaccttgg atcgaccacc    6300
catccatggt tagccgtgac aactcctgtc cgttgttgac gatttgcgcc cagtgattgc    6360
ttgcgccgtg accgctactt cttctgtgga tttcccgact ggcatcgctt catcgcgggg    6420
agacagcacg gcgttctcta ttattatctc tttgcctgtc ggtacttttg gctggtcacc    6480
gtcttggttt ttccgtttct gccttctgt gtttaagtgg acgtgacctt tgattctctg     6540
cctggtccta tctccaactt ttcttatttt tttagattct gatttttgat ttttgatttt    6600
tgattttaat tttttttct tttcttttct tattttctc tgtttactttt tctgattctc     6660 cccctgaatc ctcgtctctc tttctaatac tgcgaatgat atcttgtgtt tcgcttttca    6720
ctcccttaaa tttatgaatg aacttgccgt ccattcacta ggctcagccc cattctactc    6780
tatgttttat tcgtcactca atatatatac catatacaca acctacaagc gtccacgcta    6840
ctgacatcag cttgtcgcca tcgacgtcgg cattcttccc ctcgtcacca tcttaaagta    6900
ccaaacttct taccgaccct tcttcaccac acggaatgtt tggaaacggc cagactggac    6960
agcgtcttcc ggcgatggcc tcaccaccac acgactcgta ctactcacag tcattggcat    7020
ctagtcgatc aaggaataac tcggatgcta tggatatcta cgccatcaca gacagagatc    7080
ctccggcacg agaaccctct ggttatagcc agtggtaccg taatggttct ccaagtgtga    7140
attccattca tagcaagtaa ttcttccctg tttccttaaa tctgccgttg aatttctctc    7200
```

```
tgggctgcgt cagttgttca ctctgccgaa gctgttattg ttggacgact aatgttcttc    7260
tctgttgtta ctgtctctct ctaggagttc tgaaaaacag cctttctatg aagaaaacgg    7320
acgaatgtat catgcgtacc gcaaaggggt atatatgcta ccatgcgatg agcaggagca    7380
agatcgcctt gatatcttcc acaaattatt cacggtggca agggtgtcgg atggcctaat    7440
gtacgccccg catcccagga acggccgatt tctagacttg ggctgcggga ccgggatatg    7500
ggcaattgat gttgccaaca atacccaga cgctttcgtt gttggggttg accttgctcc     7560
catacagccc tcaaaccacc caagaattg cgaattttac gccccattcg acttcgagag     7620
tccttgggcc atgggcgagg attcttggga cctgattcac ctgcaaatgg ggtgtggaag    7680
tgtgatggga tggccgaacc tgtaccggag aatattcgct caccttcgac ccggggcttg    7740
gtttgaacag gtggagatcg actttgaacc gcggtgcgat gaccgtcctc tcgagggact    7800
agctattcga cagtggtatc agtatctaaa gcaagctaca caagatgcca tgcgacctat    7860
aaaccacaac tctcgtgata caatccgaga tctgcaggag ctggttttta ccgatattga    7920
tcatcaaatg gtggggttgc ccttaaccc atggcatcaa gacgagcacg aaagaaaggt    7980
tgctcgctgg tacaatttgg ctgtctcgga gagtattgag tcgctcagta tggcgccttt    8040
cagtcgtatt tttaattggg acttggacag aatcaggcgc atttcgtcag aagtcaagtc    8100
ggaggcgttc aacaaagaaa tacacgccta caatatcctt catatatacc aagcacggaa    8160
acctgcgaac tgattcttct accaacatgc gcacgacgga catccaaaca tgcgccagca    8220
gcgtcactag tgcccaagct ccgagttatg gggtgggcga attaccatcc aggcagtcac    8280
ctttatctgc tctttatga gctctccaaa gatgcagcga gttgatatga gcttgtgtgg    8340
tgccacttgt tagcttgcac acaacggtcc cgagcagtca ttgcttgcgt actgcaaagc    8400
aaaatcgaac tcatacgggt ctgtgatctc tatctatctg gaaaatccag tgtgtcggga    8460
gagctccatt actgggtatt cggtccgaga cgtcctgttt aggctgttgg ttatggcagc    8520
cacgaacgat gcactgagct gcctgtatca ctccagtagc acttagaagg ttgatggaaa    8580
tatacagagt ttgctttgat tatcataggt ccgagcatga ggcgggcgta cgtcttgcga    8640
aggggggttat acaaattacc caggccaaac aggcaagtca agatcatttt cgtccaaaaa    8700
atacatcgcg atgcagctct tgcccctatg gacgaaccaa tggggctgca gaatactggc    8760
aggtcattaa taggacacgg catggcatgc cctctgccct ctgccctctg cctgctctta    8820
acctggctgt ggctccttca tcacacttca ggaccacatc attccctggc attgcatgct    8880
ttcccgcttg ccaaagacag catatttatg gcgttttggg tgagtgtaat gttgataact    8940
gtatacccgg tttagttcat tctatctgtg acgacatcat ccaatcatgg ttattgctat    9000
attcgagatt cataacatga tatcacttaa aaagaatata aaaatttata taatacaatg    9060
caaagaattt tatccatgtg atcgtttgta aggtctcact accagctaac atgaaccgga    9120
aatgcaagtg tgtgagatac cagtctttgg gtatttcgcc aaaacgcctc gatagccttc    9180
aagacacccg cccacccaat gacccaagac agatgctcct gtaaattatc taatactata    9240
atgtgaactc atacaatgat atcactttaa cgccggcggc ccttttgtcc ccgggaggta    9300
ccgtttctac ctccagtact ttctttctca ccatctccgc tggcccagtc acggccagcg    9360
ccggggctac gcctccgcat tgttccggga ccgacggcaa tgatgtcctc ttcactttcg    9420
ctgtcagaaa tatctagaag cacaggcatg cgg                                 9453

<210> SEQ ID NO 146
<211> LENGTH: 1455
```

```
<212> TYPE: DNA
<213> ORGANISM: Aspergillus flavus

<400> SEQUENCE: 146
atgtttggaa acgccagac tggacagcgt cttccggcga tggcctcacc accacacgac      60
tcgtactact cacagtcatt ggcatctagt cgatcaagga ataactcgga tgctatggat     120
atctacgcca tcacagacag agatcctccg gcacgagaac cctctggtta tagccagtgg    180
taccgtaatg gttctccaag tgtgaattcc attcatagca agaacggccg atttctagac    240
ttgggctgcg ggaccgggat atgggcaatt gatgttgcca acaaatacccc agacgctttc    300
gttgttgggg ttgaccttgc tcccatacag ccctcaaacc acccaaagaa ttgcgaattt    360
tacgccccat tcgacttcga gagtccttgg gccatgggcg aggattcttg ggacctgatt    420
cacctgcaaa tggggtgtgg aagtgtgatg ggatggccga acctgtaccg gagaatattc    480
gctcaccttc gacccggggc ttggtttgaa caggtggaga tcgactttga accgcggtgc    540
gatgaccgtc ctctcgaggg actagctatt cgacagtggt atcagtatct aaagcaagct    600
acacaagatg ccatgcgacc tataaaccac aactctcgtg atacaatccg agatctgcag    660
gaggctggtt ttaccgatat tgatcatcaa atggtggggt tgccccttaa cccatggcat    720
caagacgagc acgaaagaaa ggttgctcgc tggtacaatt tggctgtctc ggagagtatt    780
gagtcgctca gtatggcgcc tttcagtcgt atttttaatt gggacttgga cagaatcagg    840
cgcatttcgt cagaagtcaa gtcggaggcg ttcaacaaag aaatacacgc ctacaatatc    900
cttcatatat accaagcacg gaaacctgcg aactgattct tctaccaaca tgcgcacgac    960
ggacatccaa acatgcgcca gcagcgtcac tagtgcccaa gctccgagtt atgggggtggg   1020
cgaattacca tccaggcagt caccttttatc tgctctttta tgagctctcc aaagatgcag   1080
cgagttgata tgagcttgtg tggtgccact tgttagcttg cacacaacgg tcccgagcag   1140
tcatttgcgt actgcaaaag caaaatcgaa ctcatacggg tctgtgatct ctatctatct   1200
ggaaaatcca gtgtgtcggg agagctccat tactgggtat tcggtccgag acgtcctgtt   1260
taggctgttg gttatggcag ccacgaacga tgcactgagc tgcctgtatc actccagtag   1320
cacttagaag gttgatggaa atatacagag tttgctttga ttatcatagg tccgagcatg   1380
aggcgggcgt acgtcttgcg aaggggggtta tacaaattac ccaggccaaa caggcaagtc   1440
aaagatcatt tcgtc                                                    1455
```

OVER-PRODUCTION OF SECONDARY METABOLITES BY OVER-EXPRESSION OF THE VEA GENE

CROSS-REFERENCE TO RELATED APPLICATIONS

This application claims priority to U.S. Provisional Application No. 61/172,514 filed Apr. 24, 2009, the entirety of which is incorporated by reference herein for all purposes.

STATEMENT REGARDING FEDERALLY SPONSORED RESEARCH OR DEVELOPMENT

This invention was made with United States government support awarded by the following agencies:
NSF 0236393
USDA/CSREES 09-CRHF-0-6055.
The United States government has certain rights in this invention.

FIELD OF THE INVENTION

The invention relates generally to methods of over-producing secondary metabolites. More particularly, the present invention is directed to methods of over-producing secondary metabolites by manipulating fungal regulatory genes involved in the control of secondary metabolite gene clusters.

BACKGROUND OF THE INVENTION

Secondary metabolites are organic compounds that are not directly involved in the normal growth, development or reproduction of organisms. They are often used as defenses against predators, parasites and diseases, for interspecies competition, and to facilitate the reproductive processes (coloring agents, attractive smells, etc).

Secondary metabolites of fungi include both "friends and foes" of human health. For example, penicillin and derivatives produced by *Aspergillus, Cephalosporium* and *Penicillium* species are widely used antibiotics, lovastatin is a potent cholesterol-lowering drug produced by *Aspergillus terreus* and aflatoxins, produced by several *Aspergillus* species, are highly toxic carcinogens contaminating many crops.

Secondary metabolic pathways are often tightly correlated with the fungal developmental program and response to external cues including light. Since secondary metabolites are usually restricted to a much more limited group of organisms, they have long been of prime importance in taxonomic research. Secondary metabolites are especially useful for drug or other technological development, or as an inspiration for unnatural products. Biosynthetic genes for fungal secondary metabolites are often clustered and regulated by pathway-specific transcription factors. Secondary metabolism is also regulated at an upper hierarchic level by a global epigenetic control mechanism.

However, methods of producing large amounts of secondary metabolites are difficult and provide unpredictable results. Therefore a need exists for methods of producing large amounts of secondary metabolites that address these problems.

The distribution of natural products is characteristically restricted to certain fungal taxa, particularly the Ascomycetes. Perhaps the greatest number of known secondary metabolites has been ascribed to the Ascomycete genus *Emericella* (asexual stage=*Aspergillus*). Much of the current understanding of fungal secondary metabolite regulation arises from studies of the genetic model *Aspergillus nidulans*. This organism produces many natural products including sterigmatocystin ST (ST; the penultimate precursor to aflatoxin) and penicillin and has been used as a heterologous host to study the biosynthesis of other natural products including lovastatin. Critical advances in understanding fungal secondary metabolism have been largely based on primary studies from *A. nidulans* and/or secondary studies in other fungi where researchers were able to exploit the knowledge gained from *A. nidulans* to their fungus of choice.

*A. nidulans*, a mold, produces many compounds relevant to biotechnology and human health and is a well-suited model for the analysis of the interplay between secondary metabolism, light and differentiation. *A. nidulans* grows vegetatively in the soil by hyphal tip extension until competent for development and secondary metabolism. In reproduction, *A. nidulans* forms airborne asexual spores in light but preferentially undergoes sexual reproduction in the dark. Sexual reproduction in the dark results in an increase in secondary metabolism and in the formation of sexual fruit bodies called cleistothecia, which consist of different cell types. Mutations resulting in defects in fungal development often impair secondary metabolism. There is genetic evidence for a connection between fruitbody formation, secondary metabolism, and light in *A. nidulans* reproduction, but the molecular mechanism is not known.

*Aspergillus flavus*, an opportunistic pathogen of oil seeds, occurs as a saprophyte in soils worldwide and colonizes several important agricultural crops, such as maize, peanut, and cottonseed, before and after harvest. The pathogen generates asexual spores, conidia, as the source of inoculum and overwinters as sclerotia which germinate to produce conidia in the subsequent season. *A. flavus* and other aspergilli, such as *Aspergillus parasiticus*, can produce the polyketide-derived carcinogenic secondary metabolite aflatoxin. In the United States, annual yield losses in the million-dollar range from aflatoxin contamination on peanut and maize crops are frequently reported. Aflatoxin-contaminated food and feed is also a major problem in developing countries, especially in Asia and Africa. Recently, an outbreak of aflatoxin poisoning from maize was reported to have killed a hundred people in Kenya. Therefore, measures to control *Aspergillus* infections and aflatoxin production are urgently needed to protect human and animal health. The identification and characterization of molecules necessary for *A. flavus* conidial, sclerotial, and aflatoxin production are critical to develop rational control strategies.

VeA, a conserved velvet protein encoded by the veA gene, increases expression during sexual development. However, VeA transport into the nucleus is inhibited by light. It acts as a negative regulator of asexual development. VeA is required for cleistothecial production in *A. nidulans* and sclerotial production in both *A. parasiticus* and *A. flavus*. In addition, the VeA gene regulates the expression of sterigmatocystin (a precursor of aflatoxin) and penicillin genes in *A. nidulans* and aflatoxin genes in *A. parasiticus* and *A. flavus*. VeA interacts with LaeA in an as-yet-unclear mechanism, although analysis shows that VeA and LaeA negatively regulate each other at the transcript level in *A. nidulans* (1) and LaeA negatively regulates veA in *A. flavus* (21).

LaeA, another protein located in the cell nucleus, is present in numerous fungi and is a master regulator of secondary metabolism in *Aspergilli* and other fungal genera. LaeA is also necessary for sclerotial formation in *A. flavus* and affects cleistothecial development in *A. nidulans*.

The deletion of LaeA silences numerous secondary metabolite gene clusters, including those responsible for the syntheses of the antibiotic penicillin as well as for toxins such as ST or gliotoxin. It has been suggested that LaeA might control the accessibility of binding factors to chromatin regions of secondary metabolite clusters because LaeA prevents heterochromatin maintenance of some clusters.

Other factors have been reported which link morphological development with secondary metabolism. Of particular interest are a family of oxylipin-producing oxygenases (encoded by ppo and lox genes) which have been shown to balance ascospore and conidial production in *A. nidulans* (40, 41) and sclerotial and conidial production in *A. flavus*, as well as secondary metabolite production in both species. Most recently, a density-dependent switch from sclerotial-to-conidial development in *A. flavus* was found to be affected by oxylipin production. Both oxylipin production and the response to oxylipin signaling are dependent on an intact VeA protein. VeA is also required for ppoA expression, and VeAP-poA interactions affect both sexual and asexual development in *A. nidulans*. The impact of the loss of these proteins on pathogenesis has been explored to some degree for LaeA and Ppo mutants but not yet reported for VeA.

LaeA is a key determinant in aspergillosis caused by *A. fumigatus* and seed rot by *A. flavus* and Ppo loss impacts virulence attributes of *A. fumigatus*, *A. nidulans*, and *A. flavus*.

Despite present methodologies, a need exists for improved methods of controlling production of secondary metabolites to obtain improved production of important natural products and/or novel natural products with medicinal value.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 12. Sequence Listing for VeA (*A. nidulans*) (SEQ ID NO: 116).

SUMMARY OF THE INVENTION

Figure 1:
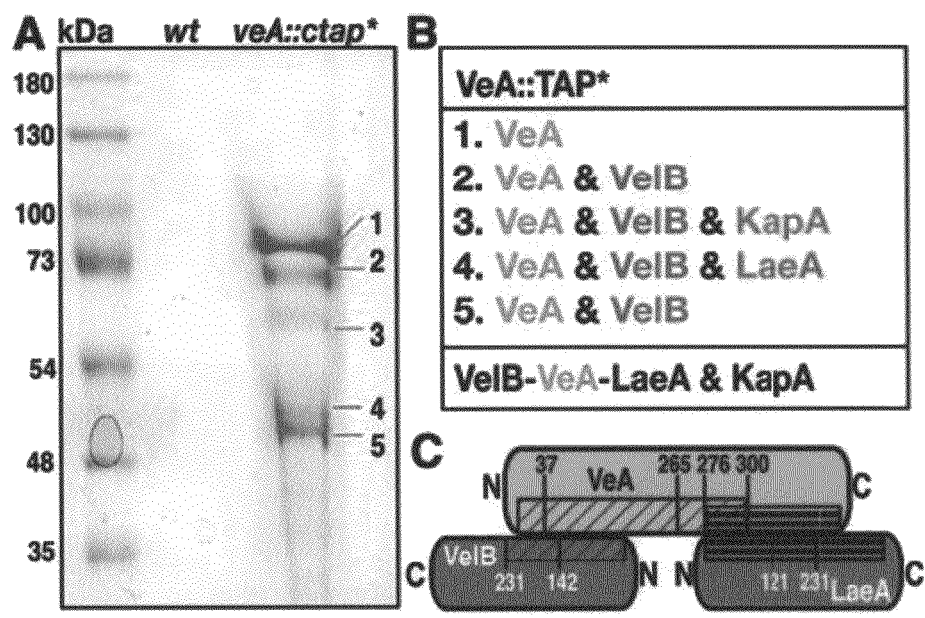
FIG. 1. Identification of VeA-associated proteins in *A. nidulans*. (A) Brilliant blue G-stained 10% SDS polyacrylamidegel electrophoresis of TAP procedure for VeA. kD, kilodaltons. (B) The polypeptides identified from the bands of affinity purification belong to corresponding proteins (details in table 4). (C) Domain mapping of the interactions based on Y2H data (FIG. 4). N, N terminus; C, C terminus.

The present invention provides a novel method of increasing the amount of a secondary metabolite produced by a cell or organism. The method comprises the steps of obtaining a cell or an organism capable of biosynthesizing a secondary metabolite; transforming the cell or organism with a nucleic acid which encodes a veA polypeptide, a polypeptide having substantial sequence identity thereto, or a fragment thereof having secondary metabolite gene cluster regulating activity; and culturing the transformed cell or organism so that an increase in production of the secondary metabolite occurs in the transformed cell or organism as compared to a non-transformed cell or organism. In one embodiment, the cell or organism is an *Aspergillus* species such as *A. nidulans* or *A. flavus*.

In another embodiment, the present invention provides a novel method of decreasing the production of a secondary metabolite by a transformed cell or organism. The method comprises the steps of: obtaining a transformed cell or organism capable of biosynthesizing a secondary metabolite, the transformed cell or organism having a defective veA gene wherein the defective veA gene is no longer biologically active and expression of secondary metabolite gene clusters is reduced; and culturing the transformed cell or organism so that a decrease in production of the secondary metabolite occurs in the transformed cell or organism as compared to a non-transformed cell or organism. In one embodiment, the cell or organism is an *Aspergillus* species such as *A. nidulans* or *A. flavus*.

In another embodiment, the present invention provides a novel method of producing an isolated secondary metabolite. The method comprises the steps of: obtaining a cell or an organism capable of biosynthesizing a secondary metabolite; transforming the cell or organism with a nucleic acid which encodes a veA polypeptide, a polypeptide having substantial sequence identity thereto, or a fragment thereof having secondary metabolite gene cluster regulating activity; culturing the transformed cell or organism under conditions conducive to increasing production of the secondary metabolite in the transformed cell or organism as compared to a non-transformed cell or organism; and recovering the secondary metabolite from the transformed cell or organism or from the culture in which the transformed cell or organism was grown in an isolated form. In one embodiment, the cell or organism is an *Aspergillus* species such as *A. nidulans* or *A. flavus*.

In another embodiment, the present invention provides a novel method for identifying a novel secondary metabolite biosynthesis gene cluster in a fungus. The method comprises the steps of: obtaining a transformed fungus having a disrupted veA gene; isolating a sample of nucleic acids from the transformed fungus, wherein the sample of nucleic acids is representative of the expressed genes of the transformed fungus; hybridizing the sample of nucleic acids isolated above or nucleic acid equivalents of same with an array comprising a plurality of nucleic acids representative of the expressed genes of a non-transformed fungus under conditions conducive to forming one or more hybridization complexes; detecting the hybridization complexes; comparing the detected levels of the hybridization complexes with the level of hybridization complexes detected in a sample of nucleic acids isolated from a veA-expressing fungus, wherein the nucleic acids isolated from a veA-expressing fungus are representative of the expressed genes of the veA-expressing fungus, and wherein an altered level of hybridization complexes detected above compared with a level of hybridization complexes of the sample of nucleic acids from the veA-expressing fungus correlates with and identifies at least one gene under regulatory control of a veA gene product; and examining genomic nucleotide sequence surrounding the at least one gene identified above to determine if the at least one gene is clustered with other secondary metabolite biosynthesis genes, thereby identifying a novel secondary metabolite biosynthesis gene cluster. In one embodiment, the cell or organism is an *Aspergillus* species such as *A. nidulans* or *A. flavus*.

DETAILED DESCRIPTION OF THE INVENTION

I. In General

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by any later-filed nonprovisional applications.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Cell Culture and Somatic Cell Genetics of Plants, Vol. 1 (I. K. Vasil, ed. 1984); R. V. Stanier, J. L. Ingraham, M. L. Wheelis, and P. R. Painter, The Microbial World, (1986) 5th Ed. Prentice-Hall.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

II. Definitions

"VeA", as used herein, refers to the amino acid sequences of the VeA protein obtained from *Aspergillus nidulans*. In addition, VeA shall also refer to the amino acid sequences of VeA obtained from any species (i.e., orthologs), particularly fungi (e.g. other strains and/or species of *Aspergillus*, and other genera), from any source whether natural, synthetic, semi-synthetic, or recombinant. The term encompasses proteins encoded by nucleotide sequences representing allelic variants as well as those containing single nucleotide polymorphisms (SNPs).

"veA", as used herein, refers to the nucleotide sequences of the veA gene obtained from *Aspergillus nidulans*. In addition, veA shall also refer to the nucleotide sequences of the veA gene obtained from any species, particularly fungi (e.g. other strains and/or species of *Aspergillus*, and other genera), from any source whether natural, synthetic, semi-synthetic, or recombinant. The term encompasses allelic variants and single nucleotide polymorphisms (SNPs).

An "allele" or "allelic sequence", as used herein, is an alternative form of the gene encoding VeA. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding VeA, as used herein, include those with deletions, insertions, or substitutions of different nucleotides resulting in a polynucleotide that encodes the same or a functionally equivalent protein to VeA. Included within this definition are polymorphisms which may or may not be readily detectable using a particular oligonucleotide probe of the polynucleotide encoding VeA, and improper or unexpected hybridization to alleles, with a locus other than the normal chromosomal locus for the polynucleotide sequence encoding VeA. The encoded protein may also be "altered" and contain deletions, insertions, or substitutions of amino acid residues which produce a silent change and result in a functionally equivalent VeA. Deliberate amino acid substitutions may be made on the basis of similarity in polarity, charge, solubility, hydrophobicity, hydrophilicity, and/or the amphipathic nature of the residues as long as the biological or immunological activity of VeA is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence", as used herein, refers to an oligopeptide, peptide, polypeptide, or protein sequence, and fragment thereof. Where "amino acid sequence" is recited herein to refer to a particular amino acid sequence "amino acid sequence" and like terms are not meant to limit the amino acid sequence to the complete amino acid sequence referenced but shall be understood to include fragments of the complete amino acid sequence. The term shall further encompass synthetic molecules as well as those occurring naturally. The term "portion" or "fragment", as used herein, with regard to an amino acid sequence (as in "a fragment of SEQ ID NO:1"), specifically refers to segments of that amino acid sequence which are not naturally occurring as fragments and would not be found in the natural state. The segments may range in size from five amino acid residues to the entire amino acid sequence minus one amino acid. Thus, a polypeptide "comprising at least a portion of the amino acid sequence of SEQ ID NO:1" or "including an amino acid sequence as set forth in SEQ ID NO:1 or fragments thereof" encompasses the full-length VeA amino acid sequences and segments thereof.

"Amplification", as used herein, refers to the production of additional copies of a nucleic acid sequence and is generally carried out using polymerase chain reaction (PCR) technologies well known in the art (Dieffenbach, C. W. and G. S. Dveksler (1995) PCR Primer, a Laboratory Manual, Cold Spring Harbor Press, Plainview, N.Y.).

"Antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

"Biologically active", as used herein, refers to a protein, polypeptide, amino acid sequence, or nucleotide sequence encoding a product having structural, regulatory, or biochemical functions of a naturally occurring molecule. Preferably, a biologically active fragment of VeA will have the secondary metabolite gene cluster regulatory capabilities of a naturally occurring VeA molecule disclosed herein.

"Complementary" or "complementarity", as used herein, refer to the natural binding of polynucleotides under permissive salt and temperature conditions by base-pairing. For example, the sequence "A-G-T" binds to the complementary sequence "T-C-A". Complementary between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence", as used herein, refers broadly to any composition containing the given polynucleotide sequence. Compositions comprising polynucleotide sequences encoding VeA or fragments thereof, may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

The phrase "correlates with expression of a polynucleotide", as used herein, indicates that the detection of the presence of ribonucleic acid that is similar to SEQ ID NO:1 by northern analysis or equivalent analysis is indicative of the presence of mRNA encoding VeA in a sample and thereby correlates with expression of the transcript from the polynucleotide encoding the protein.

"Deletion", as used herein, refers to a change in the amino acid or nucleotide sequence and results in the absence of one or more amino acid residues or nucleotides.

"Derivative", as used herein, refers to the chemical modification of a nucleic acid encoding or complementary to veA or the encoded VeA protein itself. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, or any similar process which retains the biological function of the polypeptide from which it was derived.

"Homology", as used herein, refers to sequence similarity between two peptides or between two nucleic acid molecules. Homology may be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (i.e., Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementary (e.g., less than about 30% identity). In the absence of non-specific binding, the probe will not hybridize to the second non-complementary target sequence.

"Identity", as used herein, means the degree of sequence relatedness between polypeptide or polynucleotide sequences, as the case may be, as determined by the match between strings of such sequences. "Substantial sequence identity" as used herein means at least 80% identical, more preferably 95%, 96%, 97%, 98% or 99% identical. "Identity" and "homology" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Preferred methods to determine identity are designed to give the largest match between the sequences tested. Methods to determine identity and homology are codified in publicly available computer programs. Preferred computer program methods to determine identity and homology between two sequences include, but are not limited to, the GCG program package (Devereux, J., et al., Nucleic Acids Research 12(1): 387 (1984)), BLASTP, BLASTN, and FASTA (Atschul, S. F. et al., J. Molec. Biol. 215: 403-410 (1990). The BLAST X program is publicly available from NCBI and other sources (BLAST Manual, Altschul, S., et al, NCBI NLM NIH Bethesda, Md. 20894; Altschul, S., et al., J. Mol. Biol. 215: 403-410 (1990). The well known Smith Waterman algorithm may also be used to determine identity.

"Hybridization", as used herein, refers to any process by which a strand of nucleic acid binds with a complementary strand through base pairing.

"Hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0 t$ or $R_0 t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Isolated" or "purified" or "isolated and purified" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is "isolated" even if it is still present in said organism, which organism may be living or non-living. As so defined, "isolated nucleic acid" or "isolated polynucleotide" includes nucleic acids integrated into a host cell chromosome at a heterologous site, recombinant fusions of a native fragment to a heterologous sequence, recombinant vectors present as episomes or as integrated into a host cell chromosome. As used herein, the term "substantially purified", refers to nucleic or amino acid sequences that are removed from their natural environment, isolated or separated, and are at least 60% free, preferably 75% free, and most preferably 90% free from other components with which they are naturally associated. As used herein, an isolated nucleic acid "encodes" a reference polypeptide when at least a portion of the nucleic acid, or its complement, can be directly translated to provide the amino acid sequence of the reference polypeptide, or when the isolated nucleic acid can be used, alone or as part of an expression vector, to express the reference polypeptide in vitro, in a prokaryotic host cell, or in a eukaryotic host cell.

"Exon", as used herein, refers to a nucleic acid sequence found in genomic DNA that is bioinformatically predicted and/or experimentally confirmed to contribute contiguous sequence to a mature mRNA transcript.

"Open reading frame" and the equivalent acronym "ORF", as used herein, refer to that portion of a transcript-derived nucleic acid that can be translated in its entirety into a sequence of contiguous amino acids. As so defined, an ORF has length, measured in nucleotides, exactly divisible by 3. As so defined, an ORF need not encode the entirety of a natural protein.

"Microarray" refers to an ordered arrangement of hybridizable array elements. The array elements are arranged so that there are preferably at least one or more different array elements, more preferably at least 100 array elements, and most preferably at least 1,000 array elements, on a 1 cm$^2$ substrate surface. The maximum number of array elements is unlimited, but is at least 100,000 array elements. Furthermore, the hybridization signal from each of the array elements is individually distinguishable. In a preferred embodiment, the array elements comprise polynucleotide representative of fungal-derived polynucleotide sequences.

"Modulate", as used herein, refers to a change in the activity of VeA. For example, modulation may cause an increase or a decrease in protein activity, binding characteristics, or any other biological, functional or immunological properties of VeA.

"Nucleic acid sequence" or "nucleotide sequence" or "polynucleotide sequence", as used herein, refers to an oligonucleotide, nucleotide, or polynucleotide, and fragments thereof, and to DNA or RNA of genomic or synthetic origin which may be single- or double-stranded, and represent the sense or antisense strand. Where "nucleic acid sequence" or "nucleotide sequence" or polynucleotide sequence" is recited herein to refer to a particular nucleotide sequence (e.g., the nucleotide sequence set forth in SEQ ID NO:2), "nucleotide sequence", and like terms, are not meant to limit the nucleotide sequence to the complete nucleotide sequence referenced but shall be understood to include fragments of the complete nucleotide sequence.

In this context, the term "fragment" may be used to specifically refer to those nucleic acid sequences which are not naturally occurring as fragments and would not be found in the natural state. Generally, such fragments are equal to or greater than 15 nucleotides in length, and most preferably includes fragments that are at least 60 nucleotides in length. Such fragments find utility as, for example, probes useful in the detection of nucleotide sequences encoding VeA.

"Sample", as used herein, is used in its broadest sense. A biological sample suspected of containing nucleic acid encoding VeA, or fragments thereof, or VeA itself may comprise a bodily fluid, extract from a cell, chromosome, organelle, or membrane isolated from a cell, a cell, genomic DNA, RNA, or cDNA (in solution or bound to a solid support, a tissue, a tissue print, and the like).

A "substitution", as used herein, refers to the replacement of one or more amino acids or nucleotides by different amino acids or nucleotides, respectively. The term "conservative substitution" is used in reference to proteins or peptides to reflect amino acid substitutions that do not substantially alter the activity (specificity or binding affinity) of the molecule. Typically conservative amino acid substitutions involve substitution one amino acid for another amino acid with similar chemical properties (e.g. charge or hydrophobicity). The following six groups each contain amino acids that are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of VeA, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variations on the traditional peptide linkage joining the amino acids making up the polypeptide. Where the terms are recited herein to refer to a polypeptide, peptide or protein of a naturally occurring protein molecule, the terms are not meant to limit the polypeptide, peptide or protein to the complete, native amino acid sequence associated with the recited protein molecule but shall be understood to include fragments of the complete polypeptide. The term "portion" or "fragment", as used herein, with regard to a protein or polypeptide (as in "a fragment of the VeA polypeptide") refers to segments of that polypeptide which are not naturally occurring as fragments in nature. The segments may range in size from five amino acid residues to the entire amino acid sequence minus one amino acid. Thus, a polypeptide "as set forth in SEQ ID NO:1 or a fragment thereof" encompasses the full-length amino acid sequence set forth in SEQ ID NO:1 as well as segments thereof. Fragments of VeA preferably are biologically active as defined herein.

The terms "nucleic acid" or "oligonucleotide" or "polynucleotide" or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) Tetrahedron 49:1925) and references therein; Letsinger (1970) J. Org. Chem. 35:3800; Sprinzl et al. (1977) Eur. J. Biochem. 81: 579; Letsinger et al. (1986) Nucl. Acids Res. 14: 3487; Sawai et al. (1984) Chem. Lett. 805, Letsinger et al.

(1988) J. Am. Chem. Soc. 110: 4470; and Pauwels et al. (1986) Chemica Scripta 26: 1419), phosphorothioate (Mag et al. (1991) Nucleic Acids Res. 19:1437; and U.S. Pat. No. 5,644,048), phosphorodithioate (Briu et al. (1989) J. Am. Chem. Soc. 111: 2321, O-methylphophoroamidite linkages (see Eckstein, Oligonucleotides and Analogues: A Practical Approach, Oxford University Press), and peptide nucleic acid backbones and linkages (see Egholm (1992) J. Am. Chem. Soc. 114:1895; Meier et al. (1992) Chem. Int. Ed. Engl. 31: 1008; Nielsen (1993) Nature, 365: 566; Carlsson et al. (1996) Nature 380: 207). Other analog nucleic acids include those with positive backbones (Denpcy et al. (1995) Proc. Natl. Acad. Sci. USA 92: 6097; non-ionic backbones (U.S. Pat. Nos. 5,386,023, 5,637,684, 5,602,240, 5,216,141 and 4,469, 863; Angew. (1991) Chem. Intl. Ed. English 30: 423; Letsinger et al. (1988) J. Am. Chem. Soc. 110:4470; Letsinger et al. (1994) Nucleoside & Nucleotide 13:1597; Chapters 2 and 3, ASC Symposium Series 580, "Carbohydrate Modifications in Antisense Research", Ed. Y. S. Sanghui and P. Dan Cook; Mesmaeker et al. (1994), Bioorganic & Medicinal Chem. Lett. 4: 395; Jeffs et al. (1994) J. Biomolecular NMR 34:17; Tetrahedron Lett. 37:743 (1996) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghui and P. Dan Cook. Nucleic acids containing one or more carbocyclic sugars are also included within the definition of nucleic acids (see Jenkins et al. (1995), Chem. Soc. Rev. pp 169-176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments. As used herein, oligonucleotide is substantially equivalent to the terms "amplimers", "primers", "oligomers", and "probes", as commonly defined in the art.

The term "heterologous" as it relates to nucleic acid sequences such as coding sequences and control sequences, denotes sequences that are not normally associated with a region of a recombinant construct, and/or are not normally associated with a particular cell. Thus, a "heterologous" region of a nucleic acid construct is an identifiable segment of nucleic acid within or attached to another nucleic acid molecule that is not found in association with the other molecule in nature. For example, a heterologous region of a construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a host cell transformed with a construct which is not normally present in the host cell would be considered heterologous for purposes of this invention.

A "coding sequence" or a sequence which "encodes" a particular polypeptide (e.g. a methyltransferase, etc.), is a nucleic acid sequence which is ultimately transcribed and/or translated into that polypeptide in vitro and/or in vivo when placed under the control of appropriate regulatory sequences. In certain embodiments, the boundaries of the coding sequence are determined by a start codon at the 5' (amino) terminus and a translation stop codon at the 3' (carboxy) terminus. A coding sequence can include, but is not limited to, cDNA from prokaryotic or eukaryotic mRNA, genomic DNA sequences from prokaryotic or eukaryotic DNA, and even synthetic DNA sequences. In preferred embodiments, a transcription termination sequence will usually be located 3' to the coding sequence.

The term "ortholog" refers to genes or proteins which are homologs via speciation, e.g., closely related and assumed to have common descent based on structural and functional considerations. Orthologous proteins function as recognizably the same activity in different species.

Expression "control sequences" or "regulatory elements" refers collectively to promoter sequences, ribosome binding sites, polyadenylation signals, transcription termination sequences, upstream regulatory domains, enhancers, and the like, which collectively provide for the transcription and translation of a coding sequence in a host cell. Not all of these control sequences need always be present in a recombinant vector so long as the desired gene is capable of being transcribed and translated.

"Recombination" refers to the reassortment of sections of DNA or RNA sequences between two DNA or RNA molecules. "Homologous recombination" occurs between two DNA molecules which hybridize by virtue of homologous or complementary nucleotide sequences present in each DNA molecule.

The terms "stringent conditions" or "hybridization under stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993) Laboratory Techniques in Biochemistry and Molecular Biology—Hybridization with Nucleic Acid Probes. Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe.

An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, Sambrook et al. (1989) Molecular Cloning—A Laboratory Manual (2nd ed.) Vol. 1-3, Cold Spring Harbor Laboratory, Cold Spring Harbor Press, NY, for a description of SSC buffer). Often, a high stringency wash is preceded by a low stringency wash to remove background probe signal. An example medium stringency wash for a duplex of, e.g., more than 100 nucleotides, is 1×.SSC at 45° C. for 15 minutes. An example low stringency wash for a duplex of, e.g., more than 100 nucleotides, is 4-6×SSC at 40° C. for 15 minutes. In general, a signal to noise ratio of 2× (or higher) than that observed for an unrelated probe in the particular hybridization assay indicates detection of a specific hybridization. Nucleic acids which do not hybridize to each other under stringent conditions are still substantially identical if the polypeptides which they encode are substantially identical.

This occurs, e.g., when a copy of a nucleic acid is created using the maximum codon degeneracy permitted by the genetic code.

"Expression vectors" are defined herein as nucleic acid sequences that are direct the transcription of cloned copies of genes/cDNAs and/or the translation of their mRNAs in an appropriate host. Such vectors can be used to express genes or cDNAs in a variety of hosts such as bacteria, bluegreen algae, plant cells, insect cells and animal cells. Expression vectors include, but are not limited to, cloning vectors, modified cloning vectors, specifically designed plasmids or viruses. Specifically designed vectors allow the shuttling of DNA between hosts, such as bacteria-yeast or bacteria-animal cells. An appropriately constructed expression vector preferably contains: an origin of replication for autonomous replication in a host cell, a selectable marker, optionally one or more restriction enzyme sites, optionally one or more constitutive or inducible promoters. In preferred embodiments, an expression vector is a replicable DNA construct in which a DNA sequence encoding VeA or a fragment thereof is operably linked to suitable control sequences capable of effecting the expression of the products in a suitable host. Control sequences include a transcriptional promoter, an optional operator sequence to control transcription and sequences which control the termination of transcription and translation, and so forth.

A "polymorphism" is a variation in the DNA sequence of some members of a species. A polymorphism is thus said to be "allelic," in that, due to the existence of the polymorphism, some members of a species may have the unmutated sequence (i.e. the original "allele") whereas other members may have a mutated sequence (i.e. the variant or mutant "allele"). In the simplest case, only one mutated sequence may exist, and the polymorphism is said to be diallelic. In the case of diallelic diploid organisms, three genotypes are possible. They can be homozygous for one allele, homozygous for the other allele or heterozygous. In the case of diallelic haploid organisms, they can have one allele or the other, thus only two genotypes are possible. The occurrence of alternative mutations can give rise to trialleleic, etc. polymorphisms. An allele may be referred to by the nucleotide(s) that comprise the mutation.

"Single nucleotide polymorphism" or "SNPs are defined by their characteristic attributes. A central attribute of such a polymorphism is that it contains a polymorphic site, "X," most preferably occupied by a single nucleotide, which is the site of the polymorphism's variation. Methods of identifying SNPs are well known to those of skill in the art (see, e.g., U.S. Pat. No. 5,952,174).

Abbreviations used herein include "aa", amino acid; "MMG", minimal media glucose; "MMT", minimal media threonine; "OE", over expression; "LB", Luria-Bertani; "nt", nucleotide; "ORF", open reading frame; "PCR", polymerase chain reaction; "PEG", polyethyleneglycol; "R", resistant; "WT", wild-type; and "TS", temperature sensitive.

III. The Invention

The present invention provides a novel method for producing secondary metabolites by inducing the over-expression of the fungal gene veA (SEQ ID NO: 116—see FIG. 12). Such methods include steps of: (a) obtaining a cell or an organism capable of biosynthesizing a secondary metabolite; (b) transforming the cell or organism with an nucleic acid encoding a VeA polypeptide capable of regulating biosynthesis of the secondary metabolite; and (c) culturing the transformed cell or organism so that an increase in production of the secondary metabolite occurs in the transformed cell or organism as compared to a non-transformed cell or organism.

In one embodiment of the present invention, methods of increasing the amount of a secondary metabolite as described and claimed herein are practiced in an *Aspergillus* species such as *A. nidulans*. *A. flavus* or *A. terreus*. Secondary metabolites increased by the methods include but are not limited to lovastatin or penicillin.

The invention also provides methods of decreasing the production of a secondary metabolite in a transformed cell or organism. Such methods include the steps of: (a) obtaining a transformed cell or organism capable of biosynthesizing a secondary metabolite, the transformed cell or organism having a defective veA gene wherein the defective veA gene is no longer biologically active and expression of secondary metabolite gene clusters is reduced; and (b) culturing the transformed cell or organism so that a decrease in production of the secondary metabolite occurs in the transformed cell or organism as compared to a non-transformed cell or organism. Such a gene replacement exercise could be carried out by one of skill in the art using techniques presently known in the field. Such a method would be useful in reducing or eliminating production of toxic secondary metabolites in certain organisms. For example, a non-functional variant of veA would be useful in reducing or eliminating aflatoxin production in an *A. parasiticus* or *A. flavus* strain transformed thereby. In addition, veA may be targeted by a therapeutic such that veA's ability to regulate secondary metabolite gene cluster activity is inhibited. This approach would provide a therapeutic compound able to reduce the virulence of cells or organisms, thereby providing a treatment for medical maladies involving fungal infections. Methods of identifying inhibitors of target molecules are well known in the art.

In yet another embodiment, the present invention encompasses methods of producing an isolated secondary metabolite. These methods include steps of: (a) obtaining a cell or an organism capable of biosynthesizing a secondary metabolite; (b) transforming the cell or organism with a nucleic acid encoding a VeA polypeptide capable of regulating biosynthesis of the secondary metabolite; (c) culturing the transformed cell or organism under conditions conducive to increasing production of the secondary metabolite in the transformed cell or organism as compared to a non-transformed cell or organism; and (d) recovering the secondary metabolite from the transformed cell or organism in an isolated form.

The invention also provides methods for identifying yet undiscovered secondary metabolite biosynthesis gene clusters in a variety of fungi based on the nucleic acids and transformed cells disclosed herein. Such methods are preferably carried out in a microarray format. For example, using standard microarray technology now commonly employed in the field, one of skill in the art may construct a microarray containing, for example, nucleic acids representative of the expressed genes of wild-type *A. nidulans* (see, for example, D. Bowtell and J. Sambrook, DNA Microarrays: A Molecular Cloning Manual (2000) Cold Spring Harbor Laboratory Press and P. Baldi and G. W. Hatfield, DNA Microarrays and Gene Expression: From Experiments to Data Analysis and Modeling (2002) Cambridge University Press describing standard microarray techniques data analyses applicable in the present invention). The entire genome for *A. nidulans* has been sequenced and the sequence is available in annotated form for public use (see the Whitehead Institute/MIT Center for Genome Research website). Construction of the specific nucleic acids affixed to the array substrate may be based on, for example, an expressed sequence tag database provided by the University of Oklahoma.

Using the microarray and standard hybridization techniques known in the field, the expression levels of genes in wild-type *A. nidulans, A. flavus* or other wild-type fungus versus a veA deletion mutant may then be compared to identify genes whose expression is reduced or absent in the veA deletion mutant compared to the wild-type line. The artisan may subsequently examine the genomic sequence available of, for example, *A. nidulans* or *A. flavus* to identify putative secondary metabolite biosynthesis cluster genes in the immediate vicinity of the relevant gene whose expression is initially identified as affected by the absence of veA expression. As secondary metabolite biosynthesis genes are well known to occur in clustered fashion, as described in a plurality of references cited herein, new putative secondary metabolite gene clusters may be identified by this approach.

Further, genes within a putative gene cluster may subsequently be disrupted and the mutant line's production of secondary metabolite products may then be compared with wild-type production in plus/minus fashion to identify the specific natural product produced by the newly-identified gene cluster. The natural product may then be isolated and characterized using standard techniques described and referenced herein.

The above-described screening strategies may be carried out not only between wild-type and veA deletion mutants but also, and more preferably, between veA overexpression mutants and veA deletion mutants to obtain the greatest contrast in veA-influenced secondary metabolite biosynthesis gene expression. As well, the screening methodology described herein is not limited to any one particular fungus but may be applied to any fungus having a veA ortholog (e.g., *Aspergillus* other than *A. nidulans* and *A. flavus*). For example, the genome for *Fusarium graminearum* is now available and screens utilizing veA overexpression or disruption strains to identify new *F. graminearum* secondary metabolite gene clusters may certainly be carried out based on the novel materials and teachings provided herein (also see Whitehead Institute/MIT Center for Genomic Research website).

In another embodiment of the invention, nucleotide sequences or fragments thereof which encode VeA may be used in recombinant DNA molecules to direct expression of VeA, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express VeA.

As will be understood by those of skill in the art, it may be advantageous to produce VeA-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter VeA-encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding VeA may be ligated to a heterologous sequence to encode a fusion protein. For example, to screen peptide libraries for inhibitors of VeA activity, it may be useful to encode a chimeric VeA protein that can be recognized by a commercially available antibody. A fusion protein may also be engineered to contain a cleavage site located between the VeA encoding sequence and the heterologous protein sequence, so that VeA may be cleaved and purified away from the heterologous moiety.

In another embodiment, sequences encoding VeA may be synthesized, in whole or in part, using chemical methods well known in the art. Alternatively, the protein itself may be produced using chemical methods to synthesize the amino acid sequence of VeA, or a fragment thereof. For example, peptide synthesis can be performed using various solid-phase techniques and automated synthesis may be achieved, for example, using the ABI 431A Peptide Synthesizer (Perkin Elmer).

The newly synthesized peptide may be substantially purified by preparative high performance liquid chromatography. The composition of the synthetic peptides may be confirmed by amino acid analysis or sequencing. Additionally, the amino acid sequence of VeA, or any part thereof, may be altered during direct synthesis and/or combined using chemical methods with sequences from other proteins, or any part thereof, to produce a variant polypeptide.

In order to express a biologically active VeA, the nucleotide sequences encoding VeA or functional equivalents may be inserted into an appropriate expression vector, i.e., a vector which contains the necessary elements for the transcription and translation of the inserted coding sequence. Methods which are well known to those skilled in the art may be used to construct expression vectors containing sequences encoding VeA and appropriate transcriptional and translational control elements. These methods include in vitro recombinant DNA techniques, synthetic techniques, and in vivo genetic recombination.

A variety of expression vector/host systems may be utilized to contain and express sequences encoding VeA. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, La Jolla, Calif.) or PSPORT1 plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding VeA, vectors based on SV40 or EBV may be used with an appropriate selectable marker.

The following examples describing materials and methodology are offered for illustrative purposes only, and are not intended to limit the scope of the present invention.

III. Examples

Example 1

Figure 2:
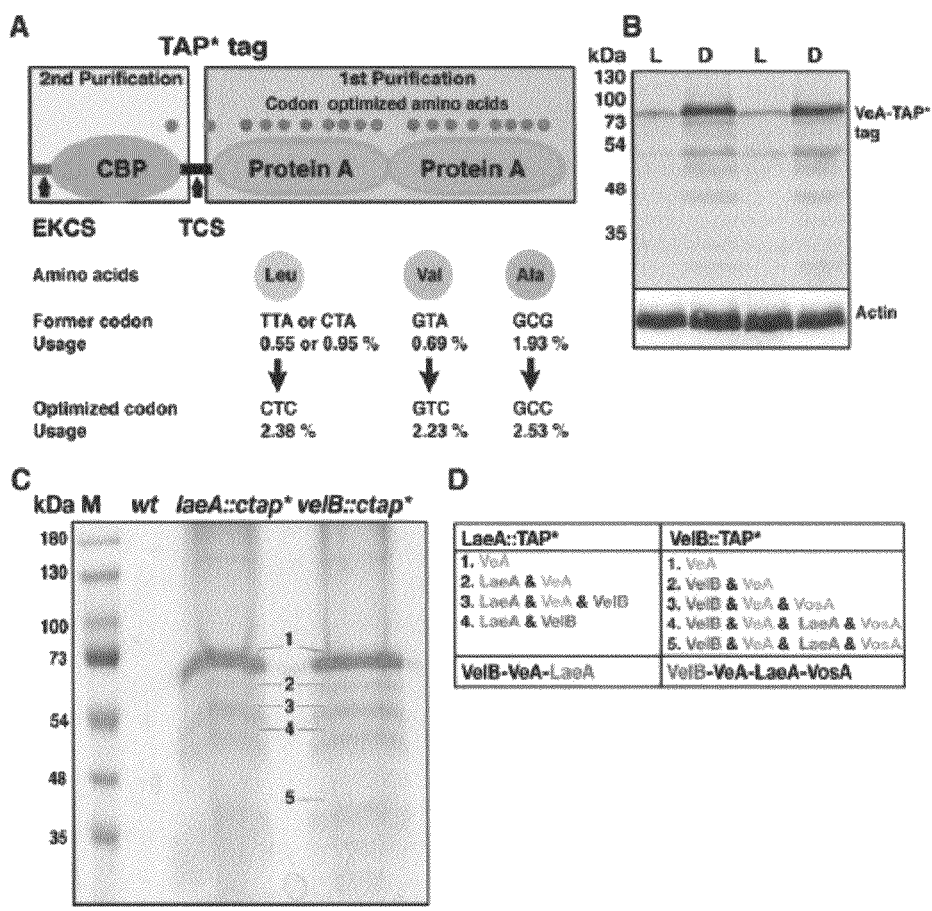
FIG. 2. Modified TAP tag* and VeA expression. (A) Depiction of the TAP tag. The codons for 18 amino acids were changed by site-directed mutagenesis and are designated as differently colored spheres. (B) Immunoblotting with antibody against calmodulin binding peptide: 85 kDa VeA::TAP* tag. In the light (L), expression is relatively low in comparison to the expression in the dark (D); as a control antiactin antibody was used. (C) Brilliant Blue G-stained 10% SDS-PAGE gel of the TAP for VelB and LaeA. (D) The polypeptides identified from the bands of two affinity purifications belong to corresponding proteins (see Table 4).

In the present invention, tandem affinity purification (TAP) was used to identify VeA-interacting proteins (FIG. 1A and FIG. 2A). Final eluates of dark- and light-grown *A. nidulans* carrying the functional veA gene tagged at its C terminus by TAP tag (veA::ctap*) were analyzed by mass spectrometry. The velvet-like protein B (VelB) (FIG. 3A, 3B), the regulator LaeA, and the α importin KapA were identified as proteins that interact with VeA in the dark (FIG. 1B and Table 4). (Importin is a type of protein that moves other protein molecules into the nucleus by binding to a specific recognition sequence, called the nuclear localization signal (NLS)).

In the light, tagged VeA protein is hardly expressed (FIG. 2B) and only copurifies with VelB. Reciprocal affinity purifications of tagged VelB and LaeA in the dark confirmed the interaction partners, except for the α importin KapA (FIGS. 2C and D). Only tagged VelB can additionally recruit the regulator of sporogenesis VosA in the dark, which seems to be an alternative binding partner for this protein.

Yeast two-hybrid (Y2H) analysis confirmed the VeA-VelB and VeA-LaeA interactions, where VelB and LaeA do not interact in this assay, suggesting that VeA acts as a bridge between VelB and LaeA (FIG. 1C).

Figure 4:
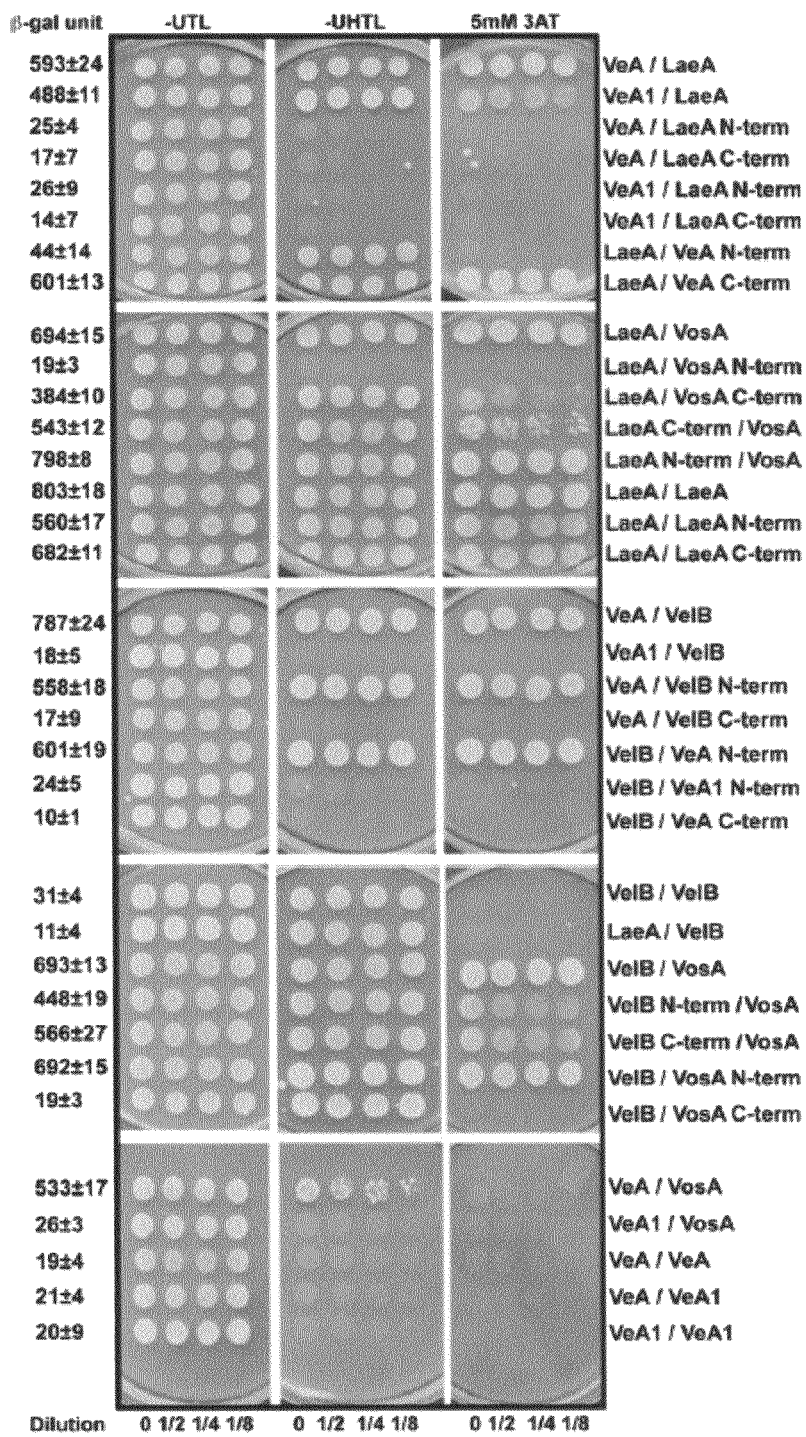
FIG. 4. Interaction domain mapping among VeA, VeA1, VosA, LaeA and VelB by yeast two-hybrid assay. Derivatives of yeast strain L40 expressing the different bait and prey fusion proteins were spotted in serial dilutions for growth on -UHTL (uracil, histidine, tryptophan and leucine), -UHTL with 5 mM 3-AT and -UTL media, and then incubated at 30° C. for 5 days. Their β-galactosidase activities were analyzed using ONPG.

The Y2H VosA-LaeA interaction supports a role of LaeA in development (FIG. 4). The C-terminal part of VeA interacts with LaeA, whereas the N-terminal part of VeA, which includes the nuclear localization signal (NLS), is required for interaction with VelB (FIG. 1C and FIG. 4).

Figure 3:
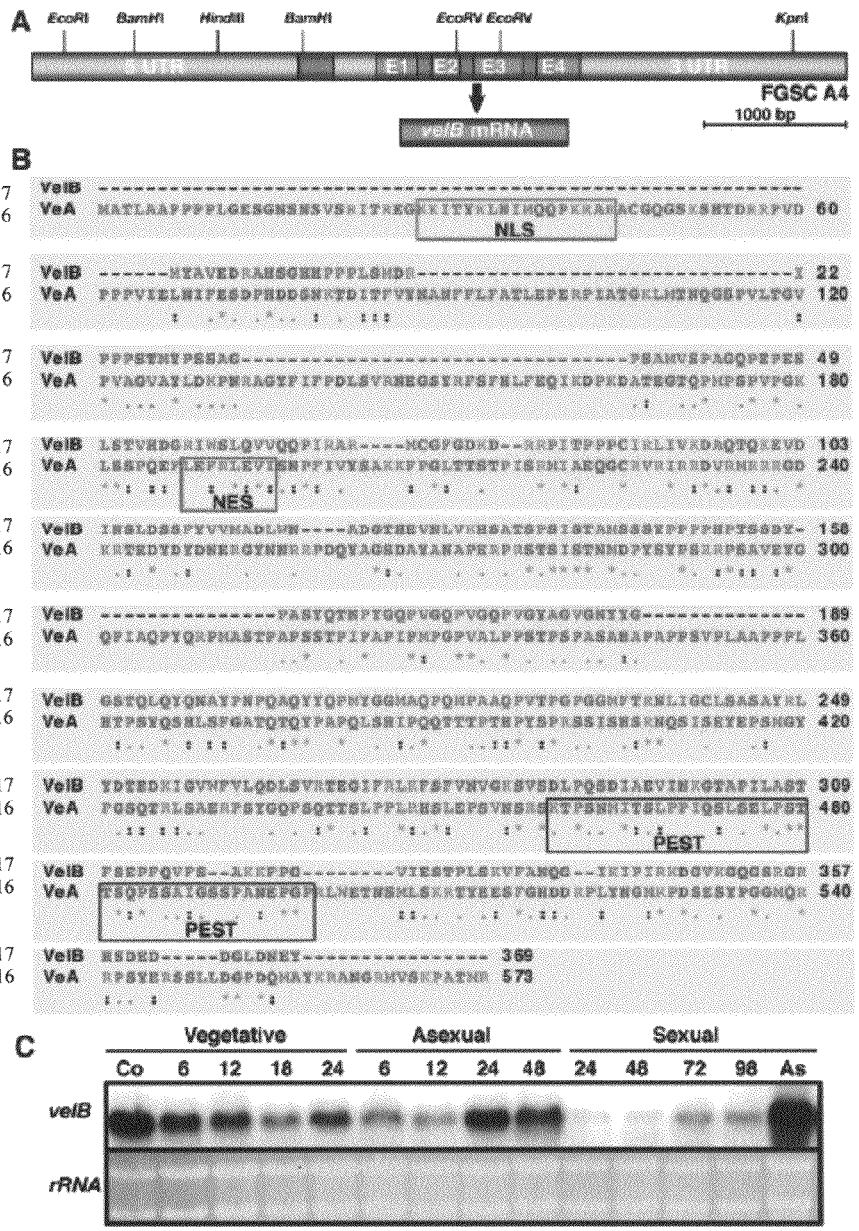
FIG. 3. velB gene structure and alignment of VeA (SEQ ID NO: 116) and VelB (SEQ ID NO: 117; Genbank Accession No. CBF89638). (A) Architecture of the velB locus of *A. nidulans*. Exons are indicated as E1, E2, E3, E4 (confirmed in cDNA) and recognition sites of common restriction endonucleases are shown. (B) Local alignment of the VelB and VeA proteins. Identical residues are indicated by an asterisk (*), conserved amino acid substitutions (similar amino acids) as two dots (:), and semi-conserved amino acid substitutions as one dot (.). The red rectangle indicates a putative nuclear localization signal (NLS) of VeA, the blue rectangle indicates a putative nuclear export signal (NES) and the black rectangle marks a conserved PEST (Pro, Glu (or Asp), Ser, Thr) motif. Red: small and hydrophobic (including aromatic amino acid), Blue: acidic, Magenta: basic, Green: hydroxyl, amine and basic amino acids. (C) Northern hybridization of VelB during different life stages of *A. nidulans*. It is highly expressed in asexual conidia and sexual ascospores. VelB expression stays at basal levels during vegetative growth and increases during late asexual (24, 48 h) or sexual (98 h and ascospores) development.
Figure 5:
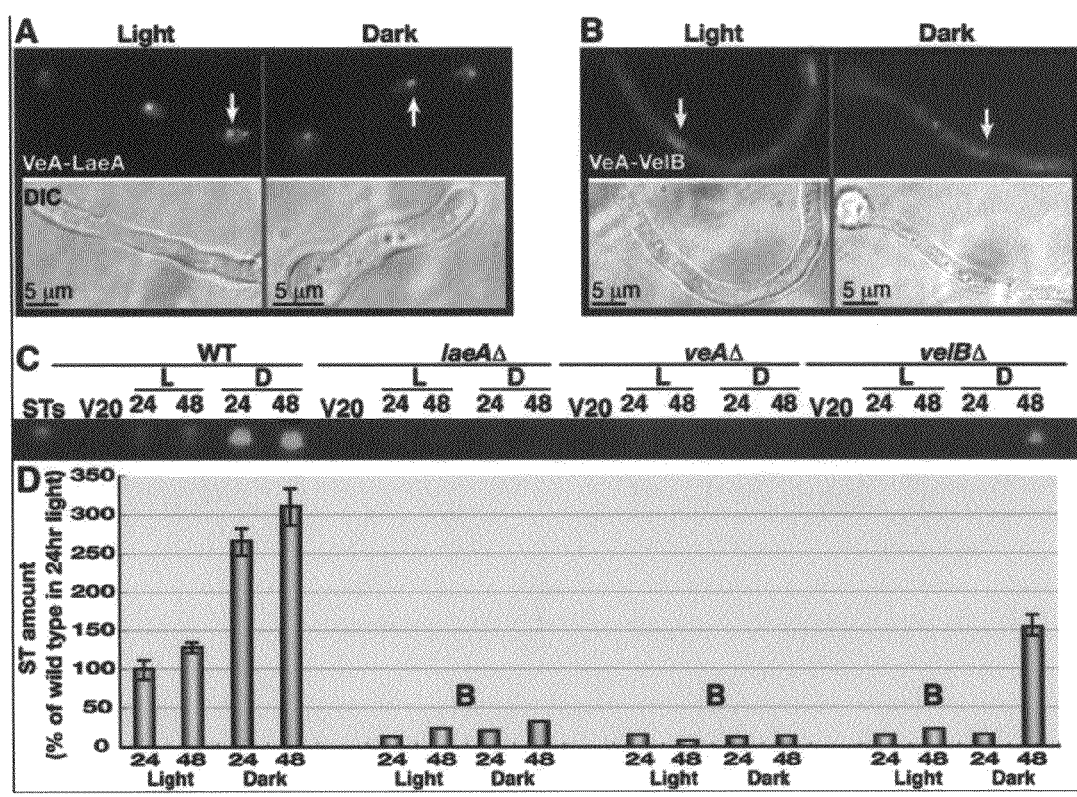
FIG. 5. BiFC studies of velvet complex components and their effect on ST production. (A) Enhanced yellow fluorescent protein fused to the N terminus of veA gene (N-EYFP::VeA) interacts with C-EYFP::LaeA in vivo, which is indicated as yellowish green specks in the nucleus. Histone 2A red fluorescent protein (H2A::mRFP) fusion visualizes the entire nucleus. Interaction does not take place in the whole nucleus but in certain points (gene clusters) that LaeA probably acts on (indicated by arrows). Differential interference contrast (DIC) shows hyphal cells. (B) N-EYFP::VeA fusion protein interacts with C-EYFP::VelB in the cytoplasm and nucleus. (C) ST production in respective mutant backgrounds and WT at different time points. STs, ST standard; V20, 20 hours vegetative growth; L, light; D, dark. 24 and 48 hour time points are shown. (D) Quantification of ST production using thin layer chromatography: In the dark, more ST is produced in the WT. Deletion of either laeA or veA results in no ST above background (denoted by B) fluctuations. Loss of velB results in basal ST production in dark.

VelB, which is conserved in the fungal kingdom, shares 18% amino acid identity with VeA but has no typical NLS (FIG. 3B). Transcript analysis reveals that VelB expression increases like that of VeA at late developmental stages (FIG. 3C). The VeA-LaeA and VeA-VelB interactions were visualized by bimolecular fluorescence complementation (BiFC) in living cells. Distinct fluorescent specks show that the VeA-LaeA interaction occurs in the nucleus, whereas VeA and VelB interact in the cytoplasm and within the nucleus (FIGS. 5A and B).

The physical interaction of VeA with VelB, as well as with LaeA, leads to the novel understanding of the present invention that VeA and VelB are functionally interdependent. Similar to veAD, the velBD mutant (FIG. 6A) no longer displays a light-dependent developmental pattern and is unable to form sexual fruit bodies, even in the dark. Asexual sporulation in velBD is impaired but not as strongly as in a veA deletion strain.

Figure 6:
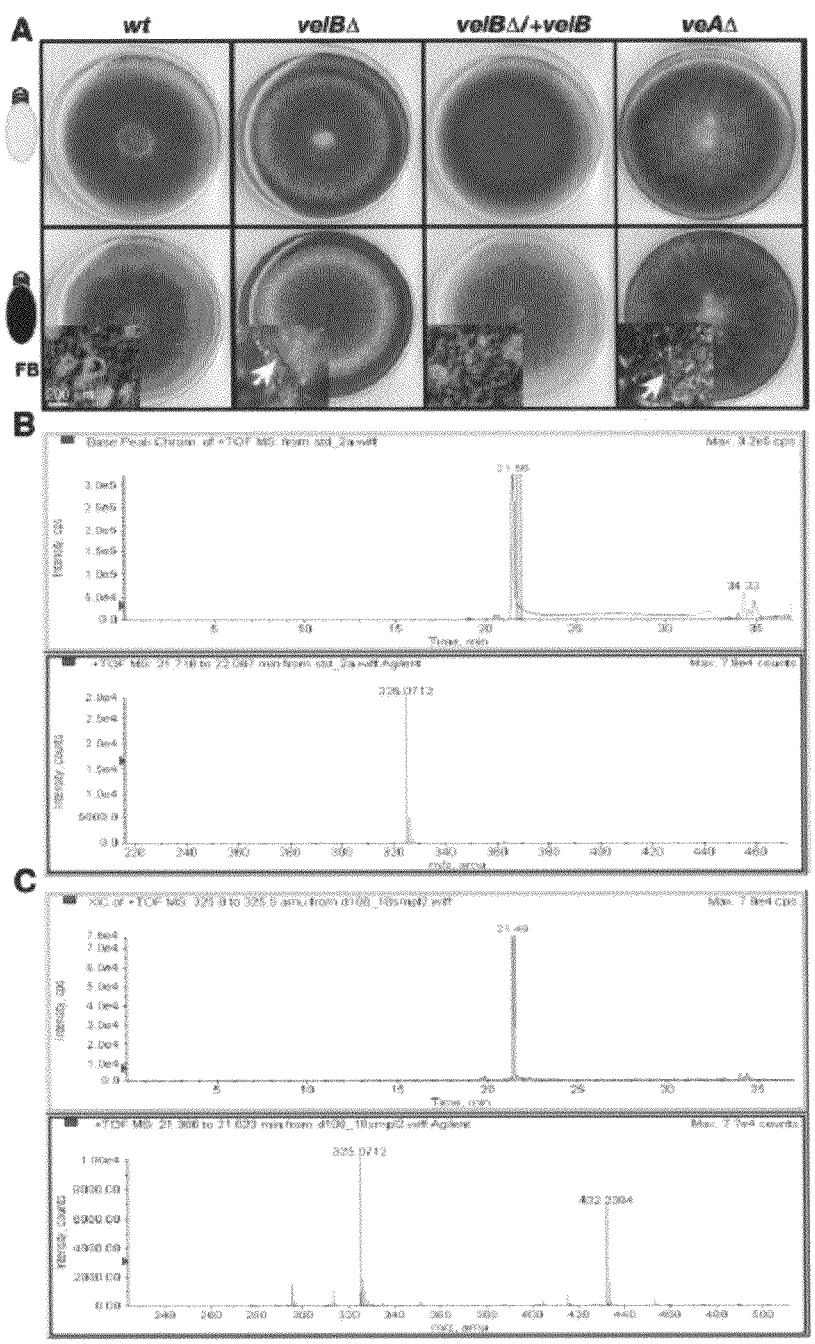
FIG. 6. Deletion of velB and impairment of sexual fruit body formation. (A) Phenotypic characterization of the velBΔ deletion strain AGB279. Defects are restored in AGB280 (+velB). Fruit body formation (FB) in TNO2A3 and AGB280 appeared as normal (red arrows), whereas aerial hyphae (white arrows) and red pigment accumulation accompanied by a lack of fruit bodies were evident for velBΔ and veAΔ strains. Pictures of cleistothecia and hyphae were taken at $10^8$-fold magnification. (B) ST standard HPLC (retention time (RT): 21.58) and the corresponding mass spectrum. (C) Confirmation of sterigmatocystin (ST) production by LC-MS in the velBΔ mutant. HPLC condition: A=0.1% formic acid in water, B=acetonitrile+0.1% formic acid, gradient=2% B to 100% B in 30 min, re-equil=18 min/flow rate=0.200 ml/min, column=ZORBAX C-18 SB, 2.1×50 mm (100 Å, 1.8 U Agilent), Temperature=40° C. Mass spectrum condition: Agilent ESITOF, source Temp=325° C., electrospray=3500 V, drying gas=91/min, nebulizer gas=30 PSI. Tolerance=less than 3 ppm. Actual was 1.6 ppm at Mass 325.0712.
Figure 7:
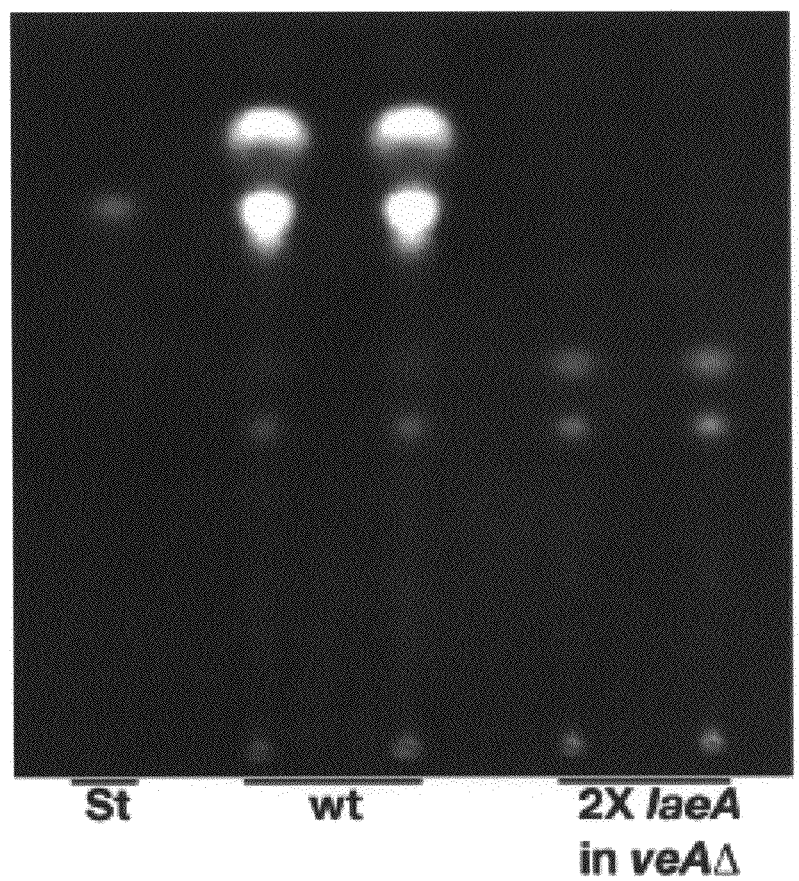
FIG. 7. Expression of extra copy of laeA in the veAΔ background. RDIT9.32 (wild-type) and RJW108.1 (veAΔ:: argB; trpC::laeA) were grown on sexual induction condition and metabolites extracted and run on a thin layer chromatography plate (chloroform:acetone=4:1). An extra copy of laeA does not restore sterigmatocystin in the veAΔ background. ST=sterigmatocystin standard.

Reintroduction of the velB locus fully rescued all of the defects (FIG. 6A). The veAD/velBD double mutant exhibited a near-identical phenotype to that of the veAD single mutant. Neither VelB overexpression in a veAD background nor VeA overexpression in a velBD background rescued the defects of the individual mutants; likewise, LaeA overexpression could not rescue secondary metabolite defects of veAD (FIG. 7).

Unlike overproduction of VeA, overexpression of VelB in a veA+ background does not cause excessive production of cleistothecia, but it induces a twofold increase in asexual sporulation in comparison to the wild type (WT). This suggests that VeA controls the number of sexual structures, whereas VelB has additional developmental functions. Secondary metabolism is impaired in veAD, resulting in a similar brownish pigment as is produced by the velBD strain.

Figure 8:
FIG. 8. Northern blot analyses. Levels of veA, velB, laeA mRNA in WT. (RDIT9.32), laeAΔ (RJW41.A), veAΔ (RJW112.2) and velBΔ (RNI18.2). All strains were grown in liquid *Aspergillus* rich medium at 37° C., 250 rpm for 20 h (shown as V20 in the figure) and then transferred onto solid MM plus supplements with or without 0.1% casamino acids for the concomitant induction. The strains grown on MM without casamino acids were incubated at 37° C. under white fluorescent light (shown as L in the figure), while the strains grown on MM with casamino acids were sealed with parafilm, wrapped with foil and incubated at 37° C. in the darkness (shown as D in the figure). Samples for RNA extraction were collected at 24 h and 48 h after induction. Twenty microgram of total RNA were loaded in each lane. EtBr-stained rRNA evaluated equal loading of total RNA.
Figure 9:
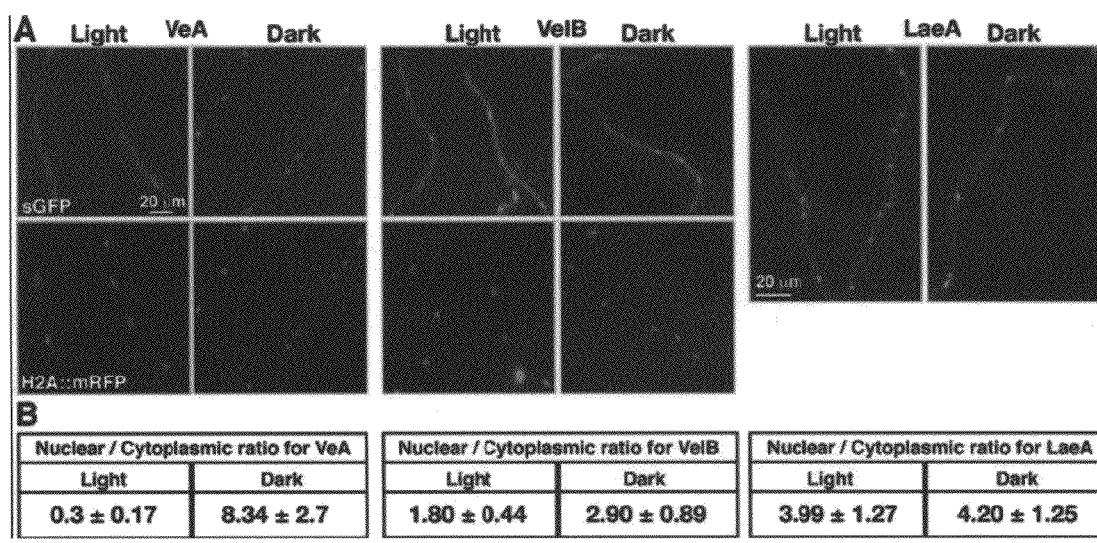
FIG. 9. Subcellular localization of the subunits of the velvet complex. (A) VeA-, LaeA-, and VelB-sGFP localizations in the presence or absence of light. VeA-sGFP shows light-dependent nuclear enrichment (counterstained with H2A::mRFP for visualization of the entire nucleus). (B) Nuclear/cytoplasmic GFP signal ratio of 100 hyphal cells each (Openlab software 5.0.1). Growth in the dark results in increased nuclear and decreased cytoplasmic fluorescence for VeA. VelB and LaeA distribution is hardly affected by illumination.

Changes in gene expression and in LaeA activity were monitored in the veAD and velBD strains (FIGS. 5C and D, FIGS. 6B and C, and FIG. 8). ST production is abolished in veAD and laeAD strains. In contrast, reduced and delayed but significant ST production in VelBD suggests residual activity of a VeA/LaeA complex in the dark. VeA is enriched in the nucleus in the dark, whereas VelB was found in both the nucleus and the cytoplasm and is hardly affected by illumination (FIGS. 9A and B).

Figure 10:
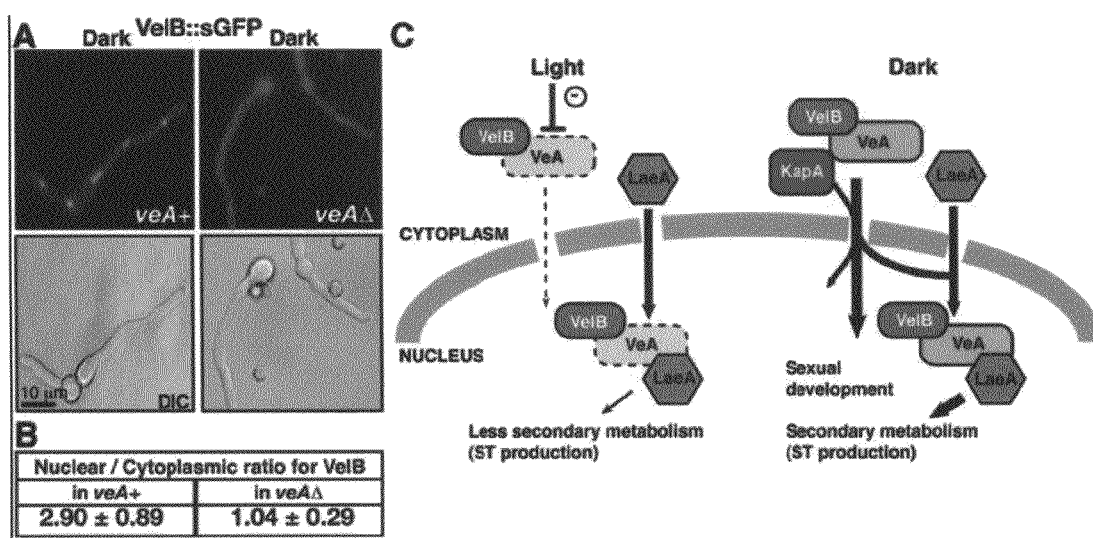
FIG. 10. VeA supports nuclear localization of VelB and formation of the velvet complex. (A) Fluorescence patterns in strains expressing velB::sgfp in the dark in veA+ and veAD backgrounds. (B) Nuclear/cytoplasmic GFP signal ratio of 100 hyphal cells each. Nuclear signal intensity is higher in the veA+ strain background than in veAD. (C) Model: (Light) VeA is mostly retained in the cytoplasm, VelB supports asexual spore formation, and LaeA shows low activity. (Dark) An increased amount of VeA is imported into the nucleus by KapA and, in addition, supports the nuclear transport of VelB. Dotted lines indicate the decreased amount of VeA that is present in the cell in the light and the impairment of VeA nuclear transport in the light. VelB/VeA control development and LaeA activity by formation of the velvet complex that affects secondary metabolite clusters expression.

Because LaeA is constitutively nuclear (FIGS. 9A and B) and the interaction of VeA and LaeA occurs in the nucleus (FIG. 5A), VelB has to enter the nucleus, despite the lack of an obvious NLS to fully control LaeA. Localization of the VelB-sGFP fusion protein (where GFP is green fluorescent protein) in a veAD background is shifted toward the cytoplasm, whereas the presence of VeA increases the nuclear localization of VelB (FIGS. 10A and B).

This suggests that VeA can assist VelB to allow an enhanced transport into the nucleus. The data provided herein suggest that the mechanism underlying the coordinated regulation of sexual development and secondary metabolism in *A. nidulans* is the interaction between the key developmental regulatory complex VelB/VeA and LaeA.

Accordingly, in the dark the VelB/VeA/LaeA velvet complex interaction controls and presumably supports the epigenetic activity of LaeA, which subsequently controls the expression of secondary metabolite gene clusters. In the light, this interaction is diminished because less VeA protein is present, and the entrance of the bridging factor VeA to the nucleus is decreased.

Because the absence of LaeA has a minor impact on development, VeA and VelB have presumably additional functions in fungal differentiation. This is also supported by the identification of VosA, a recently identified regulator of fungal sporogenesis, as an additional binding partner of VelB (FIGS. 2C and D, and Table 4).

Light triggers asexual development, corresponding to the release of high numbers of asexual spores (conidia) into the environment. These phenotypes correlate with the light-dependent cytoplasmic localization of VeA, the constitutive nuclear function of LaeA, and the partial nuclear localization of VelB, respectively. Under light conditions, when low amounts of VeA and VelB are present in the nucleus, the secondary metabolism regulator LaeA seems to be primarily active in those hyphae that are not exposed to light.

Accordingly, the deletion of laeA results in a loss of mycelial pigmentation at the bottom of the colony. The newly described fungal protein VelB, in conjunction with VeA, connects light-dependent development to LaeA-controlled secondary metabolism in *A. nidulans*. The inventors herein present evidence that the formation of this complex is the molecular basis that synchronizes developmental and metabolic changes to the disappearance of light.

This trimeric complex is designated the "velvet complex". The VelB/VeA is part of the epigenetic control of chromatin remodeling by modulating LaeA methyltransferase activity (FIG. 10C), in which VeA is functionally active in the dark, forms a complex with increased amounts of VelB, and enhances the transport of VelB to the nucleus.

Because VeA and VelB are both partially nuclear, even in the light, we presume a certain threshold is probably necessary to initiate sexual development and control LaeA. Fungal morphogenesis and secondary metabolism have traditionally been viewed as separate fields. The VelB/VeA/LaeA velvet complex elucidates the molecular mechanisms underlying the intimate relation between fungal development and secondary metabolism.

Strains, media, and growth conditions. Fungal strains used in this study are listed in Table 1.

TABLE 1

Fungal Strains.

| Strain | Genotype |
|---|---|
| *Aspergillus nidulans* | |
| FGSC4 | Glasgow wild-type |
| FGSC26 | biA1, veA1 |
| FGSC33 | biA1; pyroA4, veA1 |
| DVAR1 | pabaA1, yA2; argBΔ::trpC; trpC801; veAΔ::argB |
| AGB154 | pabaA1 |
| AGB272 | pveA::veA, ptrA; pabaA1, yA2; argBΔ::trpC; trpC801, veAΔ::argB |
| AGB273 | pveA::veA::ctap* tag, ptrA; pabaA1, yA2; argBΔ::trpC; trpC801, veAΔ::argB |
| AGB274 | pveA::veA::sgfp, ptrA; pgpdA::mrfp::h2A, pgpdA::natR; pabaA1, yA2; argBΔ::trpC; trpC801, veAΔ::argB |
| AGB275 | pniiA::velB::sgfp::niiAT, pgpdA::natR; pabaA1, yA2; argBΔ::trpC; trpC801, veAΔ::argB |
| AGB276 | pniiA::velB::niiAT, pgpdA::natR; pabaA1, yA2; argBΔ::trpC; trpC801, veAΔ::argB |
| AGB152 | pyroA4, pyrG89, veA |
| AGB277 | pniiA::velB::sgfp::niiAT, A.f. pyrG; pgpdA::mrfp::h2A, pgpdA::natR; pyroA4, pyrG89 |
| AGB278 | pniiA::velB::niiAT, A.f. pyrG; pyroA4, pyrG89 |
| TNO2A3 | pyrG89, pyroA4 |
| AGB279 | velBΔ::ptrA; pyrG89, pyroA4, argB2; nkuAΔ::argB |
| AGB280 | pvelB::velB, pgpdA::natR; velBΔ::ptrA; pyrG89, pyroA4, argB2; nkuAΔ::argB |
| AGB281 | pniiA::velB::sgfp::niiAT, A.f. pyrG; velBΔ::ptrA; pyrG89, pyroA4, argB2; nkuAΔ::argB |
| AGB282 | pveA::veA::sgfp, pgpdA::natR; velBΔ::ptrA; pyrG89, pyroA4, argB2; nkuAΔ::argB |
| AGB283 | pniiA::veA::niiAT, A.f. pyrG; velBΔ::ptrA; pyrG89, pyroA4, argB2; nkuAΔ::argB |
| AGB284 | pniiA::velB::niiAT, pgpdA::natR; pabaA1, yA2; argBΔ::trpC; trpC801; veAΔ::argB |
| AGB307 | pniiA::nyfp::veA::niiAT-pniaD::cyfp::laeA::niaDT, A.f. pyrG; pgpdA::mrfp::h2A, pgpdA::natR; pyroA4, pyrG89 |
| AGB308 | pniiA::laeA::sgfp::niiAT, pgpdA::natR |
| AGB310 | pniiA::laeA::sgfp::niiAT, pgpdA::natR; pabaA1, yA2; argBΔ::trpC; trpC801; veAΔ::argB |
| AGB311 | pniiA::laeA::sgfp::niiAT, pgpdA::natR; velBΔ::ptrA; pyrG89, pyroA4, argB2; nkuAΔ::argB |
| AGB388 | pniiA::nyfp::veA::niiAT-pniaD::cyfp::velB::niaDT, A.f. pyrG; pgpdA::mrfp::h2A, pgpdA::natR; pyroA4, pyrG89 |
| AGB389 | velB::ctap*::pgpdA::natR |
| AGB390 | laeA::ctap*::pgpdA::natR |
| RNI16.1 | pyrG89, pyroA4; nkuAΔ::argB; veA1 |
| TNI7.2 | velBΔ::pyrG; pyrG89, pyroA4; nkuAΔ::argB; veA1 |
| RRAW16 | pyrG89, yA2; veA |
| RNI18.2 | velBΔ::pyrG; veA |
| RDIT9.32 | wild type |
| RJW41.A | laeAΔ::metG; veA |
| RJW106.1 | velBΔ::pyrG; laeAΔ::metG, veA |
| RJW108.1 | veAΔ::argB; trpC::laeA |
| RJW112.2 | veAΔ::argB |
| RJW114.11 | vosAΔ::argB; laeAΔ::metG, veA |
| RJW116.2 | vosAΔ::argB; veA |
| RJW117.18 | veAΔ::argB; laeAΔ::metG |
| *Saccharomyces cerevisiae* | |
| EGY48-p1840 | MATa his3 trp1 ura3-52 leu2::3LexAop-LEU2 LexAop-LacZ/URA3 |

*A. nidulans* TNO2A3 which displays a veA+ phenotype served as wild-type for the velB deletion, AGB152 and DVAR1 were used for overexpression experiments. A velB gene replacement cassette comprising 2 kb of velB upstream and downstream flanking regions and the pyrithiamine resistance gene ptrA as selection marker was created (FIG. 11A) and introduced into the nkuAΔ background strain TNO2A3. The velB deletion mutant TNI7.2 was generated by transforming RNI16.1 with the velB deletion construct with pyrG+. RNI18.2 (ΔvelB;veA+) was isolated from a meiotic cross between RRAW16 and TNI7.2. velB and laeA loci were TAP tagged in nkuAΔ background strain TNO2A3 by using clonNat resistance.

Figure 11:
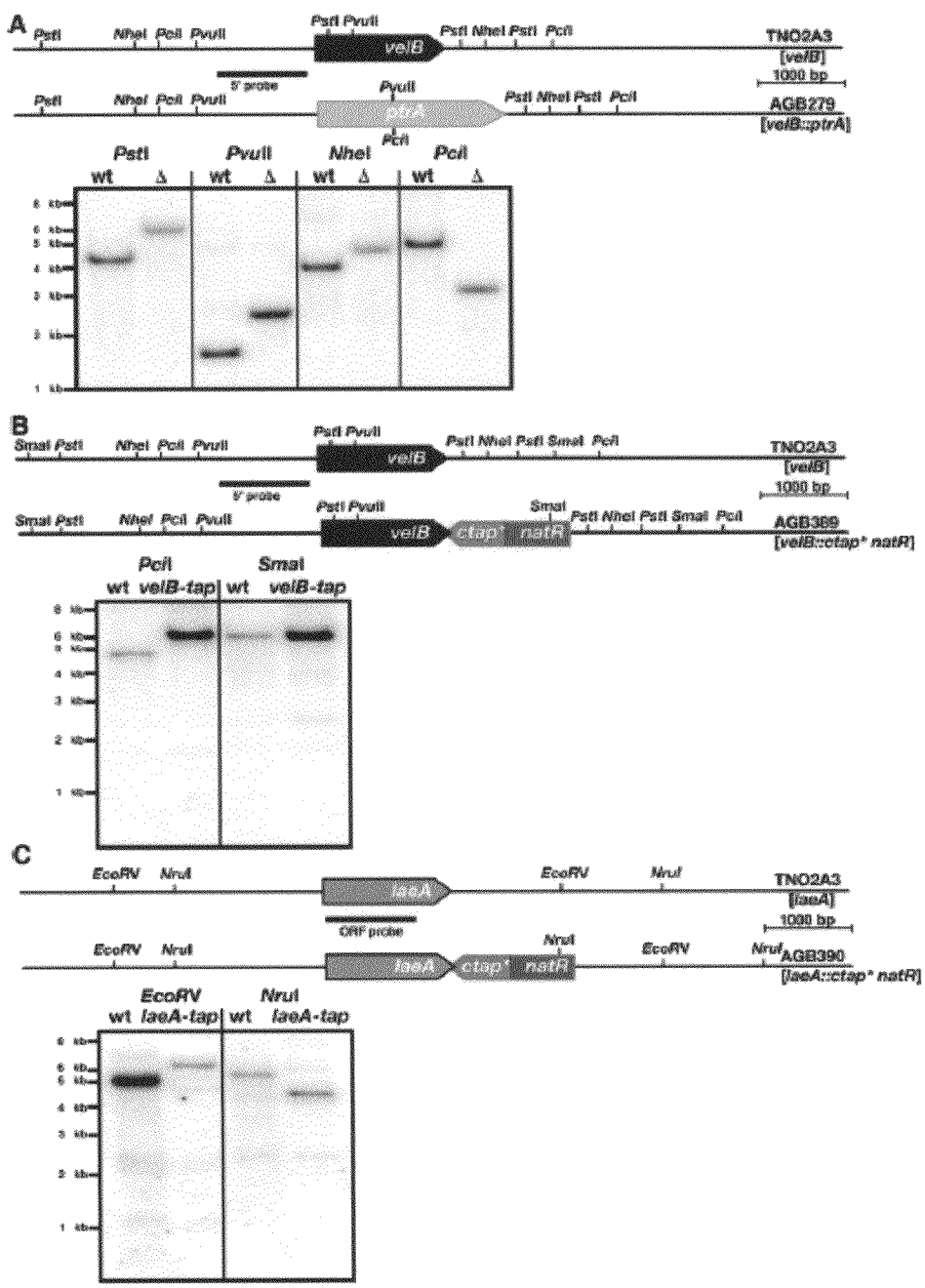
FIG. 11. Deletion of the velB locus and TAP tagging fusion genes at the velB and laeA loci. (A) Comparative depiction of the wild-type velB locus (TNO2A3) and the velB::ptrA locus (AGB279). The black bar indicates the probe for Southern hybridization. (B) The result of TAP tagging of velB locus is depicted. Autoradiography of Southern hybridization confirms the gene replacement (C) The TAP tagged laeA locus is shown. Autoradiography of Southern hybridization confirms the homologous gene replacements for the velB and laeA loci. For the deletion of velB, the ptrA (pyrithiamin resistance gene) marker was used and for the TAP tagging of velB and laeA, the (nourseothricin resistance gene) nat marker was utilized.

Correct gene replacement was confirmed by Southern analyses (FIG. 11A-C). AGB389 (veA+, velB::ctap*) and AGB390 (veA+, laeA::ctap*) strains were obtained from a meiotic cross between TNO2A3 and AGB154. *E. coli* DH5α and MACH-1 (INVITROGEN) were applied for plasmid DNA and were propagated in LB medium (1% tryptone, 0.5% yeast extract, 1% NaCl) supplemented with 100-150 μg·ml$^{-1}$ ampicillin. The bacterial strain KS272 for recombinogenic engineering was propagated in low-salt (0.5% NaCl) LB medium with 25 μg·ml$^{-1}$ chloramphenicol. Minimal medium (0.52 g·l$^{-1}$ KCl, 0.52 g·l$^{-1}$ MgSO4, 1.52 g·$^{-1}$ KH2PO4, 0.1% trace element solution, pH6.5) was used for growth of fungal strains, supplemented with appropriate amounts of 4-aminobenzoic acid (PABA, 1 μg ml$^{-1}$), Biotin (0.02 μg·ml$^{-1}$), Uracil (50 μg·ml$^{-1}$), Pyridoxine (0.05 μg·ml$^{-1}$), nourseothricin-dihydrogen sulfate (100-120 μg·ml$^{-1}$) (clonNAT, WERNER BIOAGENTS), pyrithiamine (TAKARA Bio Inc) (0.1 μg·ml$^{-1}$); 1% D-glucose was used as the source of carbon together with 10 mM ammonium or nitrate as nitrogen source. For TAP experiments, fungal strains were grown in complete medium (0.5% yeast extract, 1% bacto-peptone, 1% glucose). Sterigmatocystin (ST) production of strains was assayed as described.

Transformation procedures. *E. coli* and *A. nidulans* cells were transformed as described.

Plasmid constructions details. The plasmids utilized in this work are listed in Table 2, oligonucleotide sequences are given in Table 3.

TABLE 2

Plasmid Constructs.

| Plasmid | Description & Characteristics |
|---|---|
| pPTRII | autonomously replicating *Aspergillus* plasmid [ptrA, AMA1, bla] |
| pPTRII | Cloning vector for the construction of LexA DNA binding domain |
| pGAD424 | Cloning vector for the construction of GAL4 activation domain |
| pNJ04 | veA ORF in pTLexA |
| pNJ05 | veA ORF in pGAD424 |
| pNJ06 | veA N-terminal (1-300a.a.) in pGAD424 |
| pNJ07 | veA C-terminal (276-stop.) in pGAD424 |
| pNJ08 | veA1 ORF in pTLexA |
| pNJ09 | veA1 ORF in pGAD424 |
| pNJ10 | veA1 N-terminal (1-265a.a.) in pGAD424 |
| pNJ11 | vosA ORF in pGAD424 |
| pNJ12 | vosA-F239 (1-239a,a) in pGAD424 |
| pNJ13 | vosA C-terminal (211a.a-stop) in pGAD424 |
| pNJ14 | laeA ORF in pTLexA |
| pNJ15 | laeA-F231 (1-231a.a.) in pTLexA |
| pNJ16 | laeA-121R (121a.a.-stop) in pTLexA |
| pNJ17 | laeA ORF in pGAD424 |
| pNJ18 | laeA-F231 (1-231a.a.) in pGAD424 |
| pNJ19 | laeA-121R (121a.a.-stop) in pGAD424 |
| pNJ20 | velB ORF in pTLexA |
| pNJ21 | velB-F231 (1-231 a.a) in pTLexA |
| pNJ22 | velB-142R (142a.a.-stop) in pTLexA |
| pNJ23 | velB ORF in pGAD424 |
| pNJ24 | velB-F231 (1-231 a.a) in pGAD424 |
| pNJ25 | velB-142R (142a.a.-stop) in pGAD424 |
| pNV1 | Dominant resistance cloning plasmid |
| pME3024 | ptrA cassette with SfiI sites in EcoRV site of pBluescript II KS |
| pME3154 | veA C-Terminus::ctap* tag::veA 3' UTR in pGEM5 |
| pME3155 | veA 4.6 kb HindIII genomic fragment in pUC19 |
| pME3156 | pveA::veA::ctap* tag in pUC19 |
| pME3157 | pveA::veA::ctap* tag, ptrA, in pUC19 |
| pME3158 | velB deletion cassette [velB::ptrA] |
| pME3159 | 5 kb velB genomic locus amplicon in ApaI site of pNV1 |
| pME3160 | Expression module niiAt-pniiA/pniaD-niaDt-Af pyrG, bla |
| pME3161 | pniiA::veA cDNA in PmeI site of pME3160 |
| pME3162 | pniiA::velB cDNA in PmeI site of pME3160 |
| pME3163 | pniiA::velB::sgfp in PmeI site of pME3160 |
| pME3164 | pniiA::velB cDNA in PmeI site of pME3166 expression module |
| pME3165 | pniiA::velB::sgfp in PmeI site of pME3166 expression module |
| pME3166 | Expression module 2.6 kb amplicon from pME3160 with primers Sv315/318 in ApaI site of pNV1 |
| pME3167 | pveA::veA::sgfp, pgpdA::natR in pUC19 |
| pME3168 | pveA::veA::sgfp in pUC19 |
| pME3169 | pveA::veA::sgfp, ptrA in pUC19 |
| pME3173 | pgpdA::intron::mrfp::h2A cDNA in EcoRV and pgpdA::natR in SmaI of pBluescript II KS |
| pME3178 | veA 4.6 kb HindIII genomic fragment in HindIII and ptrA in NotI site of pBluescript II KS |
| pME3188 | pniiA::n-eyfp::veA cDNA in PmeI, and pniaD::c-eyfp::laeA cDNA in SwaI site of pME3160 expression module |

TABLE 2-continued

Plasmid Constructs.

| Plasmid | Description & Characteristics |
|---|---|
| pME3189 | pniiA::n-eyfp::veA cDNA in PmeI, and pniaD::c-eyfp::velB cDNA in SwaI site of pME3160 expression module |
| pME3190 | pniiA::laeA::sgfp in PmeI site of pME3166 expression module | pBluescript II KS (STRATAGENE) and pUC19 (FERMENTAS) were used as cloning plasmids. The plasmid pME3156 containing veA::ctap* tag fusion was constructed by recombineering an 800 by EarI fragment comprising a C-terminal fusion of the TAP* tag (FIG. 2A) to the veA coding sequence derived from pME3154 with NaeI-linearised pME3155 in E. coli. Recombineering is genetic engineering based on homologous recombination in an E. coli host strain expressing phage-derived proteins. In order to create pME3157, a ptrA pyrithiamine resistance cassette was amplified with oligonucleotides Sv129/130 from pPTRII (TAKARA) and inserted into the SmaI site of pME3156, and the final construct was used in tandem affinity purification experiments.

The veA::sgfp fusion in pME3168 was created by replacing the C-TAP* tag module in pME3154 by an OZG28/29-amplified sgfp fragment digested with NcoI/HindIII. pME3168 was digested with SmaI and a blunt ptrA (Sv129/130) was inserted resulting in pME3169. The Gpd1/Nat2-amplified 1.4 kb pgpdA::natR cassette from pNV1 was cloned into SmaI of pME3168 creating pME3167. To create a velB deletion construct, a 2 kb upstream flanking region was amplified (OZG57/58) and inserted into the EcoRV site of pBluescript KS II (STRATAGENE). The resulting plasmid was then used for insertion of a 2 kb velB downstream flanking region (OZG59/60) into SmaI site, which was then digested with SfiI to insert the SfiI-released ptrA marker from pME3024 generating pME3158, from which a 5.9 kb replacement cassette was used for deletion of velB locus.

For complementation, pME3159 was created by cloning a 5 kb velB genomic fragment (OZG99/100) in the ApaI site of pNV1. For overexpression and localization experiments, the nitrogen source-dependent expression module of pME3160 was exploited, which contains the A. nidulans niiA/niaD intergenic region flanked by the corresponding termination regions to allow expression of two genes in a bidirectional orientation at the same time. The veA and velB cDNAs were amplified and cloned into the PmeI site of pME3160 yielding pME3161 veA and pME3162 velB overexpression constructs, respectively.

The velB cDNA::sgfp fusion construct was created by fusion PCR with OZG63/116 for velB and OZG115/29 for sgfp. To create a dominant expression module, the expression module (niiAT::pniiA/pniaD::niaDT) of pME3160 was amplified with Sv315/318 and cloned into ApaI-digested flushed pNV1 to yield pME3166. The velB cDNA and velB cDNA::sgfp recombinant DNA fragments were cloned into the PmeI site of pME3166. To obtain the pgpdA::mrfp:h2A construct, the gpdA promoter and intron (Sv337/338), mrfp (Sv339/340), h2A cDNA containing terminator (Sv339/340) were amplified. Final products were fused using the double joint PCR procedure. The pgpdA::mrfp:h2A recombinant fragment was cloned into the EcoRV site of pBluescript KS II followed by pgpdA::natR cassette insertion into the SmaI site yielding pME3173. The n-eyfp::veA and c-eyfp::laeA fusion constructs were cloned into the PmeI and SwaI sites of the pME3160, respectively.

For in vivo interaction analyses, n-eyfp (OZG73/74) and veA cDNA (Sv142/143, same as OZG69/70 without restriction sites) were amplified and fused and combined with c-eyfp (OZG75/76) and laeA cDNA (OZG61/62) in plasmid pME3188 and ceyfp (OZG75/77) with velB cDNA (OZG63/64) in pME3189, respectively. The appropriate neyfp:: veA, c-eyfp::laeA or c-eyfp::velB fusion constructs were cloned into the PmeI and SwaI sites of pME3160.

For the construction of the laeA:: sgfp fusion plasmid (pME3190), laeA cDNA (OZG61/162) and sgfp (OZG29/161) were amplified, fused and inserted into the PmeI site of the pME3166 expression module under the niiA promoter.

For construction of the velB and laeA TAP* tag fragments, velB including 400 by of the 5' UTR (OZG210/211) and laeA including 400 by of the 5' UTR (OZG201/202), velB 1.6 kbp 3'UTR (OZG211/100) and laeA 1.6 kbp 3'UTR (OZG204/205) were amplified from genomic DNA.

These fragments were fused to the ctap*::natR module by fusion PCR, which creates the 5'UTR::velB::ctap*::natR::3'UTR (OZG223/224) and 5'UTR::laeA::ctap*::natR::3'UTR (OZG221/222) gene replacement fragments, respectively.

To confirm protein-protein interaction by a yeast two-hybrid assay, the ORF, N-terminal and C-terminal regions of each gene product were amplified by PCR (Table 3) from an A. nidulans cDNA library provided by Kwang-Yeop Jahng (Chonbuk University, Jeonju, Korea). The PCR product of each gene was digested with EcoRI and SalI or XhoI and cloned into the pTLexA or pGAD424 vector, respectively.

TABLE 3

Oligonucleotides utilized for plasmid generations.

| Designation | Sequence | Feature |
|---|---|---|
| OZG28 | 5'-TTT GGC CAT GGG TGG TAG CGG TGG TAT GGT GAG CAA GGG CGA GGA GCT G-3' (SEQ ID NO: 1) | sgfp-GGSGG Spacer (NcoI) |
| OZG29 | 5'-AAA ATT AAG CTC TAC TGT ACA GTT CGT CCA TGC CGT G-3' (SEQ ID NO: 2) | sgfp 3'end (HindIII) |

TABLE 3-continued

Oligonucleotides utilized for plasmid generations.

| Designation | Sequence | Feature |
|---|---|---|
| OZG57 | 5'-ACT CAC GAA TCC ACG GGA TAC AT-3' (SEQ ID NO: 3) | velB 5'UTR-A |
| OZG58 | 5'-GGC CTG AGT GGC CGG GTG GGA TAC GGT CCA TCG AAA-3' (SEQ ID NO: 4) | velB 5'UTR-B (sfiI) |
| OZG59 | 5'-GGC CAT CTA GGC CGA CCG TAT ATT GTT TCA TAA ATC CTT-3' (SEQ ID NO: 5) | velB 3'UTR-A (sfiI) |
| OZG60 | 5'-TAT GAC CGC GTG AGC AAA TAG GAC-3' (SEQ ID NO: 6) | velB 3'UTR-B |
| OZG61 | 5'-ATG TTT GAG ATG GGC CCG GTG GG-3' (SEQ ID NO: 7) | laeA start |
| OZG62 | 5'-TTA TCT TAA TGG TTT CCT AGC CTG GT-3' (SEQ ID NO: 8) | laeA stop |
| OZG63 | 5'-ATG TAC GCT GTT GAG GAT AGG GC-3' (SEQ ID NO: 9) | velB start |
| OZG64 | 5'-TTA GTA TTC GTT ATC CAG ACC ATC G-3' (SEQ ID NO: 10) | velB stop |
| OZG68 | 5'-CTC GAG TTA GTA TTC GTT ATC CAG ACC ATC G-3' (SEQ ID NO: 11) | velB start (XhoI) |
| OZG69 | 5'-CCA TGG ATG GCT ACA CTT GCA GCA CCA CCA-3' (SEQ ID NO: 12) | veA start (NcoI) |
| OZG70 | 5'-CTC GAG TTA ACG CAT GGT GGC AGG CTT TGA GA-3' (SEQ ID NO: 13) | veA stop(XhoI) |
| OZG73 | 5'-ATG GTG AGC AAG GGC GAG GAG-3' (SEQ ID NO: 14) | n-eyfp start |
| OZG74 | 5'-GGT GGT GGT GCT GCA AGT GTA GCC ATC GTG GCG ATG GAG CGC ATG ATA TAG-3' (SEQ ID NO: 15) | n-eyfp::veA fusion maker |
| OZG75 | 5'-ATG GCC GAC AAG CAG AAG AAC-3 (SEQ ID NO: 16) | c-eyfp start |
| OZG76 | 5'-ACG AGT TCC CAC CGG GCC CAT CTC AAA CAT GTG GTT CAT GAC CTT CTG TTT CAG-3' (SEQ ID NO: 17) | c-eyfp:laeA fusion maker |
| OZG77 | 5'-GGA ATG CGC CCT ATC CTC AAC AGC GTA CAT GTG GTT CAT GAC CTT CTG TTT CAG-3' (SEQ ID NO: 18) | c-eyfp velB |
| OZG98 | 5'-TTT GAA TTC ATG CAG CAG CCC AAG CGC GCG AGA G-3' (SEQ ID NO: 19) | veA1 start |
| OZG99 | 5'-AAA GGG CCC CGA GAA TGT CCG CCT GAC CCG TGC-3' (SEQ ID NO: 20) | velB complement-A (ApaI) |
| OZG100 | 5'-CCA AGT CTG CCC GAC AAG CTC ACT G-3' (SEQ ID NO: 21) | velB complement-B |
| OZG115 | 5'-CGC CAC AGC GAC GAG GAC GAT GGT CTG GAT AAC GAA TAC GGT GGT AGC GGT GGT ATG GTG AGC AAG-3' (SEQ ID NO: 22) | velB::sgfp fusion maker |
| OZG116 | 5'-GTA TTC GTT ATC CAG ACC ATC GTC-3' (SEQ ID NO: 23) | velB nostop codon |
| OZG161 | 5'-CTG CAC ATA TAC CAG CTA GGA AAA CCA TTA AGA GGT GGT AGC GGT GGT ATG GTG AGC-3' (SEQ ID NO: 24) | laeA::sgfp fusion maker |
| OZG162 | 5'-TCT TAA TGG TTT CCT AGC CTG GTA-3' (SEQ ID NO: 25) | laeA nostop codon |

TABLE 3-continued

Oligonucleotides utilized for plasmid generations.

| Designation | Sequence | Feature |
|---|---|---|
| OZG201 | 5'-CCT CGC CCT CCT GCA TCA ATA TTC GG-3'<br>(SEQ ID NO: 26) | laeA 5'UTR |
| OZG202 | 5'-GAG ACG GCT ATG AAA TTC TTT TTC CAT CTT CTC TTA CCA CCG CTA CCA CCT CTT AAT GGT TTC CTA GCC TGG TAT ATG-3'<br>(SEQ ID NO: 27) | laeA ctap* fusion maker |
| OZG204 | 5'-GAG CAG GCG CTC TAC ATG AGC ATG CCC TGC CCC TGA GAG CAA AAG GCG ACC ACA TCC AGG-3'<br>(SEQ ID NO: 28) | laeA 3'UTR-A (fusion maker) |
| OZG205 | 5'-TCG TCA ACC GCC TCA GCT GGA ACC-3'<br>(SEQ ID NO: 29) | laeA 3'UTR-B |
| OZG210 | 5'-CCT CCT CGC CGC CTC TAG TAC CGT C-3'<br>(SEQ ID NO: 30) | velB 5'UTR |
| OZG211 | 5'-GAA ATT CTT TTT CCA TCT TCT CTT ACC ACC GCT ACC ACC GTA TTC GTT ATC CAG ACC ATC GTC C-3'<br>(SEQ ID NO: 31) | velB ctap* fusion maker |
| OZG212 | 5'-CGA GCA GGC GCT CTA CAT GAG CAT GCC CTG CCC CTG AAG ACC GTA TAT TGT TTC ATA AAT CC-3'<br>(SEQ ID NO: 32) | velB 3'UTR-A (fusion maker) |
| OZG221 | 5'-CGG CTG TTT ACA TTG TGT TTT CTG G-3'<br>(SEQ ID NO: 33) | laeA-NEST-A for fusion |
| OZG222 | 5'-CCG TGA AGA ACT TGG CGT TGT AG-3'<br>(SEQ ID NO: 34) | laeA-NEST-B for fusion |
| OZG223 | 5'-GGA CCG TCT AAT TCA ACT CAC AG-3'<br>(SEQ ID NO: 35) | velB-NEST-A for fusion |
| OZG224 | 5'-CTT CCA GCG GTT ATC CTC CGT TG-3'<br>(SEQ ID NO: 36) | velB-NEST-A for fusion |
| Sv129 | 5'-ATC TGA CAG AGC GGC CGC AAT TGA TTA CG-3'<br>(SEQ ID NO: 37) | ptrA-A |
| Sv130 | 5'-ATA TAT GCG GCC GCT CTT GCA TCT TTG TTT-3'<br>(SEQ ID NO: 38) | ptrA-B |
| Sv315 | 5'-GAT ACC AAA CGG AAC TGG CTG TTA TGG-3'<br>(SEQ ID NO: 39) | expression module A |
| Sv318 | 5'-ATC GAC GCA ACC ATC GAA GCA GC-3'<br>(SEQ ID NO: 40) | expression module B |
| Sv337 | 5'-GAT CTT TGC CCG GTG TAT GAA ACC-3'<br>(SEQ ID NO: 41) | gpdA promoter A (-432) |
| Sv338 | 5'-TCG GAG GAG GCC ATG GTG ATG TCT GCT CAA GC-3'<br>(SEQ ID NO: 42) | gpdA promoter B |
| Sv339 | 5'-GAC ATC ACC ATG GCC TCC TCC GAG GAC GTC ATC-3'<br>(SEQ ID NO: 43) | mrfp start |
| Sv340 | 5'-GGC TCC AGC GCC TGC ACC AGC TCC GGC GCC GGT GGA GTG GCG GC-3'<br>(SEQ ID NO: 44) | mrfp stop |
| Sv341 | 5'-GGA GCT GGT GCA GGC GCT GGA GCC ACT GGC GGC AAA TCT GGT GG-3'<br>(SEQ ID NO: 45) | h2A start |
| Sv342 | 5'-ATC TGG AGG GGA CAG GCA GTT TAT-3'<br>(SEQ ID NO: 46) | terminator for h2A |
| GpdA | 5'-GGG TTT CGA ACT ACA TCA AGG GTC CAA GAC CGA CAT CGA GGC TCT GTA CAG TGA CCG GTG-3'<br>(SEQ ID NO: 47) | gpdA promoter |
| Nat2 | 5'-AGG GAA TTC TCA GGG CAG GGC AT GC-3'<br>(SEQ ID NO: 48) | natR stop |

TABLE 3-continued

Oligonucleotides utilized for plasmid generations.

| Designation | Sequence | Feature |
|---|---|---|
| OMN131 | 5'-GAA GGT CGA TGA TGG TGT GAT G-3'<br>(SEQ ID NO: 49) | velB 5' amplify |
| OMN132 | 5'-CTA GAG GTA AAG ATC AAG GTA G-3'<br>(SEQ ID NO: 50) | velB 3' amplify |
| OMN133 | 5'-CTG ATG GCT GAA TGA AGC ACA G-3'<br>(SEQ ID NO: 51) | velB 5' nested |
| OMN134 | 5'-TGC TTT ACG ACG ATA GCC ATG C-3'<br>(SEQ ID NO: 52) | velB 3' nested |
| OMN135 | 5'-ggtg aag agc att gtt tga ggca GCG GCC AGT CTT TAG ACA AAT G-3'<br>(SEQ ID NO: 53) | velB 5' rev with pyrG tail (bold) |
| OMN136 | 5'-agt gcc tcc tct cag aca gaa ta GGA TAA CGA ATA CTA AAG ACC G-3'<br>(SEQ ID NO: 54) | velB 3' for with pyrG tail (bold) |
| OMN125 | 5'-TAT GCA CTG GCA CTC AAG CAA CCG-3'<br>(SEQ ID NO: 55) | velB forward primer for probe |
| OMN126 | 5'-GTG CAT GAC GGT CGT ATC TGG TCC-3'<br>(SEQ ID NO: 56) | velB reverse primer for probe |
| OKH181 | 5'-GGC TGT AGT CGC TTT GTT-3'<br>(SEQ ID NO: 57) | veA forward primer for probe |
| OKH182 | 5'-GCC CAG TGT AAG AAA GGA-3'<br>(SEQ ID NO: 58) | veA reverse primer for probe |
| OJA242 | 5'-GCT GTC GAT CTT TGT ACC CTG-3'<br>(SEQ ID NO: 59) | laeA forward primer for probe |
| OJA243 | 5'-CGT TCC TGG ATG TGG TCG CCT-3'<br>(SEQ ID NO: 60) | laeA reverse primer for probe |
| oNK11 | 5'-ATATAAGCTTAATGGCTACACTTGCAGCACCAC-3'<br>(SEQ ID NO: 61) | veA forward for Y2H |
| oNK12 | 5'-ATATGTCGACTTAACGCATGGTGGCAGGCTTTG-3'<br>(SEQ ID NO: 62) | veA reverse for Y2H |
| oNK13 | 5'-ATATAAGCTTAATGCAGCAGCCCAAGCGCGCGAG-3'<br>(SEQ ID NO: 63) | veA1 forward for Y2H |
| oNK14 | 5'-ATATGAATTCATGAGTGCGGCGAACTATCCAG-3'<br>(SEQ ID NO: 64) | vosA forward for Y2H |
| oNK15 | 5'-ATATGTCGACTCACCGAGGAGTTCCGTTCGCTG-3'<br>(SEQ ID NO: 65) | vosA reverse for Y2H |
| oNK32 | 5'-ATATGAATTCATGTTTGAGATGGGCCCGGTGGGAAC-3'<br>(SEQ ID NO: 66) | laeA forward for Y2H |
| oNK33 | 5'-ATATGTCGACTTATCTTAATGGTTTCCTAGCCTG-3'<br>(SEQ ID NO: 67) | laeA reverse for Y2H |
| oNK74 | 5'-ATATAAGCTTATCAACGAGCATCAGCACAAAC-3'<br>(SEQ ID NO: 68) | veA C-terminal forward for Y2H |
| oNK75 | 5'-ATATGTCGACTCCATATTCCACTGCCGACGGAC-3'<br>(SEQ ID NO: 69) | veA N-terminal reverse for Y2H |
| oNK76 | 5'-ATATGAATTCTCTGATAGGACAGCCATGCAAATC-3'<br>(SEQ ID NO: 70) | vosA C-terminal forward for Y2H |
| oNK78 | 5'-ATATGAATTCATGTACGCTGTTGAGGATAG-3'<br>(SEQ ID NO: 71) | velB forward for Y2H |
| oNK79 | 5'-ATATGTCGACTTAGTATTCGTTATCCAGACCA-3'<br>(SEQ ID NO: 72) | velB reverse for Y2H |
| oNK130 | 5'-ATATGAATTCACGGTAGCGCGGGTATCGGAG-3'<br>(SEQ ID NO: 73) | laeA-121R forward for Y2H |

TABLE 3-continued

Oligonucleotides utilized for plasmid generations.

| Designation | Sequence | Feature |
|---|---|---|
| oNK132 | 5'-ATATGAATTCATGTCTTCATCGTATCCACCAC-3' (SEQ ID NO: 74) | velB-142R forward for Y2H |
| oNK138 | 5'-ATATCTCGAGACCAGGCACCGGGACGGAGATG-3' (SEQ ID NO: 75) | laeA-F231 reverse for Y2H |
| oNK140 | 5'-ATATCTCGAGAGTAGGAATAGTCCCTACTCGTG-3' (SEQ ID NO: 76) | vosA-F239 reverse for Y2H |
| oNK141 | 5'-ATATCTCGAGTCCAGGCCCTGGAGTAACTGGCTG-3' (SEQ ID NO: 77) | velB-F231 reverse for Y2H |
| jwbvelBF | 5'-TTCGCTAGACAGCTCATTCTACG-3' (SEQ ID NO: 78) | velB forward primer for probe |
| jwbvelBR | 5'-TAGTATTCGTTATCCAGACCATCG-3' (SEQ ID NO: 79) | velB reverse primer for probe |
| jwbvelAF | 5'-ATACCTGGATAAACCAAATCGAGC-3' (SEQ ID NO: 80) | veA forward primer for probe |
| jwbvelAR | 5'-AGGTTCATTCGCAGGGCTAGAC-3' (SEQ ID NO: 81) | veA reverse primer for probe |
| jwblaeAF | 5'-ACCACTACAGCTACCACTCTCC-3' (SEQ ID NO: 82) | laeA forward primer for probe |
| jwblaeAR | 5'-TTTCGATGCTCTCTGAGACGGC-3' (SEQ ID NO: 83) | laeA reverse primer for probe |

Yeast two-hybrid analysis. pTLex (Cho et al., 2003; kindly provided by Suhn-Kee Chae at Paichai University, Daejeon, Korea) derived bait and pGAD424 (CLONTECH) derived prey constructs were cotransformed into the *Saccharomyces cerevisiae* reporter strain MO and transformants were selected on -UTL -trp, -leu) containing 2% glucose media. To further confirm the interactions of proteins, several transformants of each combination were tested for their coloration on the medium -UTL containing X-Gal, and the transformants were tested for β-galactosidase activity using the yeast β-galactosidase assay kit (PIERCE).

Recombinant DNA procedures, hybridization techniques and analysis of nucleic acids. For recombinant DNA technology, standard protocols were performed. Taq, Pfu (MBI FERMENTAS) and Platinum Taq DNA polymerase (INVITROGEN) were used in PCR reactions, and cloning steps were confirmed by sequencing. Fungal genomic DNA was prepared from ground mycelia, and Southern blot analyses were conducted as described. Total RNA samples were analyzed by Northern hybridization as described. The STRATAGENE Prime-It II kit was used to radioactively label hybridization probes in the presence of [α-32P]dATP.

To produce autoradiographs, washed membranes were exposed to KODAK X-Omat films. Sequence data were analyzed using the LASERGENE software package from DNASTAR, and alignments were created by the Clustal W method. PEST motifs were analyzed on the web tool and NES patterns were identified on the web tool.

TAP purification. The fungal strains AGB272, AGB273 (veA::ctap*), AGB389 (velB::ctap*) and AGB390 (laeA::ctap*) were grown in liquid culture and transferred onto CMM (minimal medium +0.1% casein hydrolysate) plates, wrapped with parafilm and covered with aluminium foil to induce sexual development or were transferred onto MM and incubated under white fluorescent light without wrapping.

At 48 h post induction of sexual and 24 h post induction of asexual development, the differentiating mycelia were ground in liquid nitrogen to prepare crude extracts in B* buffer (100 mM Tris-HCl pH7.6, 250 mM NaCl, 10% glycerol, 0.05% NP-40, 1 mM EDTA, 2 mM DTT) supplemented with an EDTA-free protease inhibitors mix (ROCHE), phosphatase inhibitors (MERCK) and specified protease inhibitors as recommended in the procedure at the NCRR.

Crude extracts were centrifuged for 20 min at 15000 g and transferred into 50 ml falcon tubes. Protein extracts were incubated for 3 h on a rotator with 300 μl of IgG sepharose 6 Fast Flow (AMERSHAM) at 4° C. After that point, the standard protocol (Step 14) as outlined at the NCRR web site was followed with minor modifications. TEV cleavage was executed under rotation using 350U of AcTEV (INVITROGEN) in the presence of 1 μM E-64 (CALBIOCHEM) protease inhibitor at 4° C. for 5 h; 1 mM PMSF (phenylmethanesulfonylfluoride) was included in the calmoduline binding step on affinity resin (STRATAGENE). The TCA (trichloroacetic acid)-precipitated eluate was loaded onto a 10% polyacrylamide gel and stained with Coomassie Brilliant Blue G (Sigma). Protein bands were cut out and submitted for mass spectrometry.

Immunoblotting. For detection of the VeA::TAP* fusion protein and actin, anti-calmodulin binding peptide antibody (UPSTATE, catalog 07-482) and anti-actin antibody (MP Biomedicals, catalog 69100) were used.

LC-MS/MS Protein Identification. Excised polyacrylamide gel pieces of stained protein bands were digested with trypsin according to Shevchenko et al. Tryptic peptides extracted from each gel slice were injected onto a reversed-phase liquid chromatographic column (Dionex-NAN75-15-03-C18 PM) by using the ultimate HPLC system (Dionex, Amsterdam, Netherlands) to further reduce sample complexity prior to mass analyses with an LCQ DecaXP mass spectrometer (ThermoElectron Corp, San Jose, Calif.) equipped with a nanoelectrospray ion source. Cycles of MS spectra with m/z ratios of peptides and four data-dependent MS2 spectra were recorded by mass spectrometry.

The "peak list" was created with extracts provided by the Xcalibur software package (BioworksBrowser 3.1). The MS2 spectra with a total ion current higher than 10,000 were used to search for matches against a public *A. nidulans* genome-wide protein sequence database of the BROAD INSTITUTE (9542 sequences, December 2005, plus 180 sequences of the most commonly appearing contaminants, e.g., keratins and proteases, provided with the BioworksBrowser package) using the TurboSEQUEST algorithm of the Bioworks software (Version 3.1, Thermo Electron Corp).

The search parameters included based on the TurboSEQUEST algorithm were: (i) precursor ion mass tolerance less than 1.4 amu, (ii) fragment ion mass tolerance less than 1.0 amu, (iii) up to three missed tryptic cleavages allowed, and (iv) fixed cysteine modification by carboxyamidomethylation (plus 57.05 amu) and variable modification by methionine oxidation (plus 15.99 amu) and phosphorylation of serine, threonine, or thyrosine (plus 79.97 amu).

In accordance with the criteria described by Link et al., matched peptide sequences of identified proteins had to pass the following: (i) the cross-correlation scores (Xcorr) of matches must be greater than 2.0, 2.5, and 3.0 for peptide ions of charge state 1, 2, and 3, respectively, (ii) ΔCn values of the best peptide matches must be at least 0.4, and (iii) the primary scores (Sp) must be at least 600.

Protein identification required at least two different peptides matching these criteria. The degree of completeness of the b- and y-ion series for each SEQUEST result was manually checked for every protein identified. Peptides of identified proteins were individually blasted against the NCBI database to ensure their unambiguous assignment to the TurboSEQUEST-specified protein. See also the *Multiple Consensus Reports* for the detailed TurboSEQUEST identifications in the Table 4. The three top scoring peptides are listed for all identifications.

TABLE 4

Mass Spectrometry Data of Protein Identifications.

| Peptide Sequence | MH+ | Charge | XCorr | Delta Cn | Sp | RSp | Ions |
|---|---|---|---|---|---|---|---|
| AN1052.2 (hypothetical protein similar to velvet A) 1[1] | | | | | 1210.3 | 121(121-0-0-0-0) | |
| R.LEVISNPFIVYSAK.K (SEQ ID NO: 84) | 1580.85 | 2 | 5.27 | 0.59 | 1188.8 | 1 | 21/26 |
| R.LEVISNPFIVYSAK.K (SEQ ID NO: 85) | 1425.59 | 2 | 4.52 | 0.32 | 1075.5 | 1 | 18/24 |
| R.LEVISNPFIVYSAK.K (SEQ ID NO: 86) | 2135.24 | 3 | 6.84 | 0.66 | 2085.3 | 1 | 37/72 |
| AN0363.2 (hypothetical protein)[2] | | | | | 1508.3 | 151(150-1-0-0-0) | |
| K.IGVWFVLQDLSVR.T (SEQ ID NO: 87) | 1532.81 | 2 | 5.18 | 0.37 | 1490.4 | 1 | 18/24 |
| K.SVSDLPQSDIAEVINK.G (SEQ ID NO: 88) | 1715.88 | 2 | 5.35 | 0.55 | 803.4 | 1 | 24/30 |
| R.IWSLQVVQQPIR.A (SEQ ID NO: 89) | 1467.74 | 2 | 4.62 | 0.35 | 1568.4 | 1 | 17/22 |
| AN0807.2 (hypothetical protein)[3] | | | | | 186.2 | 19(18-0-2-0-0) | |
| K.EIHAYNILHIYQAR.K (SEQ ID NO: 90) | 1741.98 | 2 | 4.85 | 0.61 | 1789.0 | 1 | 20/26 |
| R.YAVAGGPAPWNR.N (SEQ ID NO: 91) | 1259.40 | 2 | 4.70 | 0.52 | 1632.0 | 1 | 19/22 |
| R.VSESLIYAPHPINGR.F (SEQ ID NO: 92) | 1641.81 | 2 | 4.17 | 0.57 | 930.5 | 1 | 20/28 |
| AN2142.2 (hypothetical protein similar to AF465210_1 karyopherin alpha)[4] | | | | | 660.3 | 66(66-0-0-0-0) | |
| K.IIQVALDGLENILK.V (SEQ ID NO: 93) | 1539.84 | 2 | 5.09 | 0.57 | 2402.5 | 1 | 22/26 |
| K.IQAVIEAGIPR.R (SEQ ID NO: 94) | 1167.38 | 2 | 3.87 | 0.44 | 1618.2 | 1 | 18/20 |
| K.TPQPDWNTIAPALPVLAK.L (SEQ ID NO: 95) | 1933.24 | 2 | 4.40 | 0.64 | 942.9 | 1 | 19/34 |
| AN0363.2 (hypothetical protein)[5] | | | | | 220.2 | 22(22-0-0-0-0) | |
| K.GTAPILASTFSEPFQVFSAK.K (SEQ ID NO: 96) | 2099.37 | 2 | 5.28 | 0.47 | 1045.5 | 1 | 22/38 |
| K.IGVWFVLQDLSVR.T (SEQ ID NO: 97) | 1532.81 | 2 | 4.30 | 0.43 | 1499.0 | 1 | 18/24 |
| K.SVSDLPQSDIAEVINK.G (SEQ ID NO: 98) | 1715.88 | 2 | 5.34 | 0.48 | 846.1 | 1 | 24/30 |
| AN1052.2 (hypothetical protein similar to velvet A)[6] | | | | | 778.4 | 78(77-1-0-0-0) | |
| K.DATEGTQPMPSPVPGK.L (SEQ ID NO: 99) | 1612.79 | 2 | 3.70 | 0.45 | 516.1 | 1 | 18/30 |
| K.KFPGLTTSTPISR.M (SEQ ID NO: 100) | 1405.62 | 2 | 2.61 | 0.53 | 519.5 | 1 | 15/24 |

TABLE 4-continued

Mass Spectrometry Data of Protein Identifications.

| Peptide Sequence | MH+ | Charge | XCorr | Delta Cn | Sp | RSp | Ions |
|---|---|---|---|---|---|---|---|
| K.LMTNQGSPVLTGVPVAGVAYLDKPNR.A (SEQ ID NO: 101) | 2699.12 | 2 | 6.16 | 0.61 | 737.2 | 1 | 35/100 |
| AN0807.2 (hypothetical protein)[7] | | | | | 454.3 | | 46(45-0-0-1-0) |
| K.EIHAYNILHIYQAR.K (SEQ ID NO: 102) | 1741.97 | 2 | 3.01 | 0.59 | 960.3 | 1 | 17/26 |
| R.IQQLAADVK.S (SEQ ID NO: 103) | 986.15 | 2 | 3.12 | 0.33 | 1015.4 | 1 | 15/16 |
| R.YAVAGGPAPWNR.N (SEQ ID NO: 104) | 1259.40 | 2 | 3.39 | 0.58 | 1119.0 | 1 | 17/22 |
| AN1959.2 (hypothetical protein)[8] | | | | | 660.3 | | 66(66-0-0-0-0) |
| K.DVDNTDGGFFVWGDLSIK.V (SEQ ID NO: 105) | 1986.13 | 2 | 4.21 | 0.56 | 931.0 | 1 | 19/34 |
| RLKDVDNTDGGFFVWGDLSIK.V (SEQ ID NO: 106) | 2227.46 | 2 | 4.14 | 0.56 | 1200.5 | 1 | 21/38 |
| AN0807.2 (hypothetical protein)[9] | | | | | 220.2 | | 22(22-0-0-0-0) |
| K.EIHAYNILHIYQAR.K (SEQ ID NO: 107) | 1741.97 | 2 | 4.15 | 0.58 | 1819.4 | 1 | 20/26 |
| R.WYNLAVSESIENLSLAPFSR.V (SEQ ID NO: 108) | 2297.55 | 2 | 4.30 | 0.54 | 1495.0 | 1 | 22/38 |
| R.YAVAGGPAPWNR.N (SEQ ID NO: 109) | 1259.40 | 2 | 3.90 | 0.54 | 1681.7 | 1 | 20/22 |
| AN0363.2 (hypothetical protein)[10] | | | | | 778.4 | | 78(77-1-0-0-0) |
| K.GTAPILASTFSEPFQVFSAK.K (SEQ ID NO: 110) | 2099.37 | 3 | 5.29 | 0.56 | 1021.1 | 1 | 30/76 |
| K.SVSDLPQSDIAEVINK.G (SEQ ID NO: 111) | 1715.88 | 2 | 5.59 | 0.51 | 799.5 | 1 | 21/30 |
| R.IWSLQVVQQPIR.A (SEQ ID NO: 112) | 1467.74 | 2 | 4.29 | 0.45 | 2227.8 | 1 | 18/22 |
| AN1052.2 (hypothetical protein similar to velvet A)[11] | | | | | 454.3 | | 46(45-0-0-1-0) |
| R.LEVISNPFIVYSAK.K (SEQ ID NO: 113) | 1580.85 | 2 | 4.44 | 0.55 | 1269.4 | 1 | 21/26 |
| R.RPDQYAGSDAYANAPERPR.S (SEQ ID NO: 114) | 2135.24 | 3 | 5.25 | 0.65 | 1825.0 | 1 | 36/72 |
| R.RPSAVEYGQPIAQPYQR.P (SEQ ID NO: 115) | 1961.17 | 3 | 3.99 | 0.56 | 1044.4 | 1 | 29/64 |

[1] Avg. Mass: 63831.1; pI: 9.43; Coverage (amino acids): 39.4%
[2] Avg. Mass: 37062.4; pI: 5.97; Coverage (amino acids): 30.4%
[3] Avg. Mass: 41578.2; pI: 5.93; Coverage (amino acids): 28.6%
[4] Avg. Mass: 60627.4; pI: 5.00; Coverage (amino acids): 11%
[5] Avg. Mass: 37062.4; pI: 5.97; Coverage (amino acids): 33.3%
[6] Avg. Mass: 63831.1; pI: 9.43; Coverage (amino acids): 40.6%
[7] Avg. Mass: 41578.2; pI: 5.93; Coverage (amino acids): 18.0%
[8] Avg. Mass: 49010.4; pI: 8.45; Coverage (amino acids): 31.5%
[9] Avg. Mass: 41578.2; pI: 5.93; Coverage (amino acids): 36.6%
[10] Avg. Mass: 37062.4; pI: 5.97; Coverage (amino acids): 32.8%
[11] Avg. Mass: 63831.1; pI: 9.43; Coverage (amino acids): 38.9%

Fluorescence microscopy. *A. nidulans* spores ($5.5 \times 10^5$) were inoculated either on 18 mm×18 mm cover slips submerged in appropriately supplemented liquid medium or on large glass slides covered with a thin layer of medium and incubated at 30° C. overnight. The effect of illumination on localization of VeA and VelB was investigated by growing selected strains in darkness and light on the agar surface or in the submerged culture. Cover slips were mounted on microscope slides using spore storage solution (0.002% Tween, 0.5% NaCl) and fixed with wax.

Fluorescence photographs were taken with a ZEISS Axiovert S100 microscope supported with a HAMAMATSU OCRA-ER digital camera, using the Openlab™ V5.0.1 software package (IMPROVISION, Coventry, UK). For the quantification of the GFP signals, nuclei were defined as ROIs (Area of interest). Pixel intensity within the defined ROIs were analysed by using Openlab tmV5.0.1 software package (IMPROVISION, Coventry, UK). Nuclei were verified by overlaying the GFP and Ds Red signals. Subcellular distribution was observed with a 100× objective using 495 and 558 nm extinction and emission filters. No autofluorescence was observed. All images were taken using the same exposure and microscope settings.

Sterigmatocystin extraction and thin layer chromatography (TLC) analysis. Samples (1.6 cm diameter disc with fungal samples and agar together) were collected after asexual developmental induction. The fungal samples were ground in 3 ml dd$H_2O$ in a homogenizer, and then 3 ml chloroform was added to extract ST from the aqueous phase. About 1.8 ml chloroform containing ST was collected after centrifugation, and air-dried. The dried extracts were resuspended in 50 μl of chloroform, and 10 μl were separated in hexane:ethyl acetate (4:1) or chloroform:acetone (4:1) on TLC plates. ImageQuant TL (Amersham Biosciences Co.)

was used for ST densitometry. Data are presented as graphs with bars which stand for mean+/−standard error (FIG. 2D). For statistical analysis, data were analyzed using the JMP software package (version 3.2.6, SAS Institute, Inc, Cary, N.C.).

According to the Tukey-Kramer multiple comparison test at P≤0.05, the three mean values for WT in the dark are significantly different from WT in the light and velBΔ in the dark after 48 hours (FIG. 5D). The graphs without bars do not produce ST above background noise (indicated by "B").

Example 2

In this example, the inventors created several *A. flavus* isogenic mutants differing only in copy number of veA and laeA genes, including ΔveA, ΔlaeA, multicopy laeA (MClaeA), and MCveA strains and a double MC strain (MCveA-laeA). The respective VeA and LaeA mutants exhibited critical differences in cell density responses and invasion of host tissues, despite gross similarities between sclerotial and aflatoxin production.

Considering the interdependence of oxylipin function with VeA coupled with the VeA-LaeA interaction, we postulated that VeA mutants would also be impaired in seed pathogenesis in a manner similar to that of LaeA mutants and, furthermore, that both mutants could be affected in density-dependent development. To explore these hypotheses, we created several *A. flavus* isogenic mutants differing only in copy number of veA and laeA genes, including ΔveA, ΔlaeA, multicopy laeA (MClaeA), and MCveA strains and a double MC strain (MCveA-laeA). The respective VeA and LaeA mutants exhibited critical differences in cell density responses and invasion of host tissues, despite gross similarities between sclerotial and aflatoxin production.

Fungal strains and growth conditions. The *Aspergillus flavus* strains used and generated in this example are listed in Table 5. ΔveA (SEQ ID NO: 142); containing 5' veA flanking region (nucleotides 1-1314 in SEQ ID NO: 142), *A. fumigatus* pyrG (nucleotides 1315-3264 in SEQ ID NO: 142), and 3' flanking region of the veA open reading frame (nucleotides 3265-4556 in SEQ ID NO: 142). MCveA (SEQ ID NO: 143) was generated by transformation with pSA3.X, and contained *A. flavus* veA (nucleotides 1368-3156 in SEQ ID NO: 143):: *A. fumigatus* pyrG (nucleotides 3700-5681 in SEQ ID NO: 143) in TOPO-TA cloning plasmid (TOPO-TA pCR2.1); *A.flavus* 5' (nucleotides 259-1367 in SEQ ID NO: 143) and 3'flank (nucleotides 3157-3674 in SEQ ID NO: 143); nucleotides 258, 3675-3679, 3699, 5682-5686 in SEQ ID NO: 143 are restriction sites (EcoRI or SpeI). ΔlaeA (SEQ ID NO: 144) was generated by transformation with PLRM5, and contained *A. fumigatus* pyrG (nucleotides 1535-3547 in SEQ ID NO: 144), *A. flavus* 5' (nucleotides 46-1531 in SEQ ID NO: 144) and 3'flank (nucleotides 3554-4933 in SEQ ID NO: 144); nucleotides 43-45, 1532-1534, 3548-3553, and 4934 in SEQ ID NO: 144 are restriction sites. MClaeA (SEQ ID NO: 145) was generated by transformation with pLRM11, and contained *A. parasiticus* niaD (nucleotides 2-5128 in SEQ ID NO: 145):: *A. flavus* laeA (nucleotides 5134-9452 in SEQ ID NO: 145) in Invitrogen pCR bluntII TOPO plasmid (pLRM9); nucleotides 1, and 5129-5133 in SEQ ID NO: 145 are restriction sites. MCveA-laeA was prepared by co-transformation with pSA2.8 and PLRM11 plasmids using *A. flavus* laeA (SEQ ID NO: 146).

TABLE 5

*Aspergillus flavus* strains.

| Strain | Genotype* | Source |
|---|---|---|
| NRRL 3357 | Wild type | Horowitz Brown et al. 2008. Appl. Environ. Microbiol. 74: 5674-5685. |
| NRRL 3357.5 | pyrG⁻ | Horowitz Brown et al. 2008. Appl. Environ. Microbiol. 74: 5674-5685. |
| TSA 1.54 (ΔveA) | pyrG⁻ ΔveA::AfpyrG | This study |
| TSA 2.46 (MCveA) | pyrG⁻ AfpyrG veA | This study |
| TJW 71.1(ΔlaeA) | pyrG⁻ ΔlaeA::AfpyrG | Kale, et al.. 2008. Fungal Genet. Biol. 45: 1422-1429. |
| TJW 79.13 (MClaeA) | pyrG⁻ ΔlaeA::AfpyrG niaD⁻ niaD laeA | Kale, et al.. 2008. Fungal Genet. Biol. 45: 1422-1429. |
| TSA 2.8 (MCveA-laeA) | pyrG⁻ AfpyrG veA niaD laeA | Horowitz Brown et al. 2008. Appl. Environ. Microbiol. 74: 5674-5685. |

*Af, *A. fumigatus*

All strains were maintained as stocks in glycerol and grown at 29° C. on glucose minimal medium (GMM) (36) amended with appropriate supplements for spore production.

Fusion PCR and vector construction. All primers used in this example are listed in Table 6.

TABLE 6

Primer sequences.

| Primer | Sequence (5'-3') |
|---|---|
| 5'F veA For | ACAACCCTGGACTCTGGAAT (SEQ ID NO: 118) |
| 5'F veA Rev | CGAAGAGGGTGAAGAGCATTGTTTGAGGCA GAGGACGCGTTGACTGTGATG (SEQ ID NO: 119) |
| 3'F veA For | TGACGACAATACCTCCCGACGATACC TGGGTTGATTCCTGCTTTTCCTCC (SEQ ID NO: 120) |
| 3'F veA Rev | TCTCGTTCTCCCATTTACCT (SEQ ID NO: 121) |
| A. fumigatus pyrG For | TGCCTCAAACAATGCTCTTC (SEQ ID NO: 122) |
| A. fumigatus pyrG Rev | CAAGGTATCGTCGGGAGGT (SEQ ID NO: 123) |
| Nested For | AATCACGGACCTCGAAGCAG (SEQ ID NO: 124) |
| Nested Rev | GGGGTCTTGATATGGCGAAT (SEQ ID NO: 125) |

TABLE 6-continued

Primer sequences.

| Primer | Sequence (5'-3') |
|---|---|
| Int veA For | CAACAAGACCGACATCACCTTC (SEQ ID NO: 126) |
| Int veA Rev | CCATTCTTGGGATAGCTGCAAC (SEQ ID NO: 127) |
| MC veA For | CAACGAACTAGTCCGCCTGCCCTTAACCTCCA (SEQ ID NO: 128) |
| MC veA Rev | GCATACACTAGTCTCGCATGCCAGTGGATGGG (SEQ ID NO: 129) |
| veA-pyrG Rev | CATCGGTTGACTACGCTCGCA (SEQ ID NO: 130) |
| laeA-niaD For | GACCTGTGGTGAAACCTGAGG (SEQ ID NO: 131) |
| veA Northern For | CTAGCTGGTCATTATTTGATCTCG (SEQ ID NO: 132) |
| veA Northern Rev | GTTGTAGAGTGGACGATCATCATG (SEQ ID NO: 133) |
| laeA Northern For | CCTTGTATGATGTATGTATGATGAGC (SEQ ID NO: 134) |
| laeA Northern Rev | GACAGCGAAAGTGAAGAGGACATC (SEQ ID NO: 135) |
| actin Northern For | GAAGCGGTCTGAATCTCCTG (SEQ ID NO: 136) |
| actin Nothern Rev | ACAGTCCAAGCGTGGTATCC (SEQ ID NO: 137) |
| aflR Northern For | AGAGTCTTCCTTCAGCCAGGTC (SEQ ID NO: 138) |
| aflR Northern Rev. | GTGGGGCTTTTCTTCATTCTCG (SEQ ID NO: 139) |

* Bold characters flag restriction enzyme (SpeI) site.

The veA replacement PCR products were constructed using fusion PCR following Szewczyk et al. Starting with wild type A. flavus veA (SEQ ID NO: 141, containing 1314 bp of the 5' flanking region and 1292 by of the 3' flanking region of the veA open reading frame), the 1.3-kb fragments upstream and downstream of the veA coding region were amplified by PCR with primers 5'F veA For and Rev for the upstream fragment and primers 3'F veA For and Rev for the downstream fragment, using NRRL 3357 (prototroph) genomic DNA as a template. Next, a 1.9-kb fragment of the pyrG auxotrophy marker gene was amplified from A. fumigatus AF293 genomic DNA using primers A. fumigatus pyrG For and Rev. These three amplified PCR products were cleaned with a QIAquick gel extraction kit (Qiagen), quantified, and fused using published procedures. The PCR product was amplified with primers Nested For and Rev. All PCR steps were performed using an Expand long template PCR system (Roche Diagnostics GmbH, Mannheim, Germany) according to the manufacturer's instructions.

The final construct was confirmed with endonuclease digestion and PCR using primers Int veA For and Rev for internal veA and primers A. fumigatus pyrG For and Rev for pyrG. The veA complementation vector was constructed in two steps. First, the 1.9-kb A. fumigatus pyrG PCR fragment was amplified and ligated into the pCR2.1-TOPO vector (Invitrogen) to create pSA2.4. Next, a 4.4-kb SpeI fragment containing the A. flavus veA gene was amplified from A. flavus NRRL 3357 genomic DNA with primers MC veA For and Rev and ligated into the SpeI site of pSA2.4 to create the veA complementation vector, pSA3.13. The vector was confirmed by PCR with primers MC veA For and veA-pyrG Rev and endonuclease digestion.

Fungal transformation procedure and mutant confirmation. For fungal transformation, protoplasts were produced from freshly germinated conidia of NRRL 3357.5 (pyrG auxotroph) and transformed using a polyethylene glycol method. The final fusion PCR product (5 µg) was used for replacement of veA with pyrG after gel purification using a QIAquick gel extraction kit (Qiagen) to create strain TSA 1.54 (SEQ ID NO: 142; containing 1314 bp of the 5' veA flanking region, 1950 bp of A. fumigatus pyrG, and 1292, by of the 3' flanking region of the veA open reading frame). The veA::pyrG vector, pSA3.13, was used alone or else cotransformed with pLRM11.1, a vector containing both laeA and niaD, to create MC strains with multiple copies of veA alone and MC strains with multiple copies of both veA and laeA (TSA 2.46 and TSA 2.8, respectively, were used for these studies).

Correct transformants were identified by analyzing genomic DNA using PCR screens followed by Southern analyses. Primers Int veA For and Rev, Nested For and Rev (4.3 kb for the wild type and 4.6 kb for transformants), and A. fumigatus pyrG For and Rev were used to identify pyrG replacement of veA. MC transformants were identified by PCR with primers MC veA For and veA-pyrG Rev and primers laeA-niaD For and laeA Northern Rev. Southern analysis was performed for each PCR-identified transformant to confirm single gene replacement of veA in TSA 1.54, at least 2 copies of veA in TSA 2.46, and at least 2 copies of veA and laeA in TSA 2.8. Probes were created with primers Nested For and Rev for the veA open reading frame (ORF) and primers laeA Northern For and Rev for the laeA ORF.

Northern analysis. To examine the expression of veA and laeA transcripts, Northern analysis was performed. Fifty-milliliter amounts of liquid GMM were inoculated with $10^6$ spores/ml of appropriate strains and incubated with shaking at 250 rpm at 29° C. under dark conditions. After 48 h, the mycelium was collected and total RNA was extracted by using the Trizol method (Invitrogen). Blots were hybridized with a veA fragment amplified using the primers Northern For and Rev, an laeA fragment amplified using the primers Northern For and Rev, an actin fragment amplified using the primers actin Northern For and Rev, and an aflR fragment amplified using the primers aflR Northern For and Rev from NRRL3357 genomic DNA. Detection of signals was carried out with a Phosphorimager-SI (Molecular Dynamics).

Physiological experiments. Conidial production, sclerotial formation, and colony diameter were measured for fungal strains following the methods of Horowitz Brown et al. Briefly, 8-ml amounts of 1.6% GMM plus 2% sorbitol agar were overlaid with 3-ml amounts of 0.7% agar GMM plus 2% sorbitol agar containing $10^2$, $10^4$, and $10^6$ spores/plate of each A. flavus strain for culture. For conidial counts, three 1.5-cm plugs from each plate were homogenized in 5 ml of 0.01% Tween 80 (vol/vol) water, diluted to 1 x, and counted with a hematocytometer. To visualize sclerotium formation, plates were sprayed with 70% ethanol to kill and wash away conidia. The exposed sclerotia were then collected, lyophilized, and weighed (dry weight per plate). Growth diameter was measured following a point inoculation of 5 µl of $10^6$ spores/ml for each strain on 30 ml of 1.6% GMM. Cultures were grown at 29° C. under continuous dark or light conditions for 3 days (conidia production), 7 days (sclerotia formation), and 3 and 6 days (colony diameter). Each treatment was replicated four times.

To assay for growth on different fatty acids, the wild-type, ΔlaeA, and ΔveA strains were examined for growth on (i) 20 mM hexanoic acid (6 C), 6 mM oleic acid (18 C), and 4.9 mM erucic acid (22 C) as the sole carbon source, with the fatty acids substituting for the glucose in GMM, or (ii) GMM supplemented with these same molarities of fatty acids, following the method of Maggio-Hall and Keller. Growth diameter was measured following a point inoculation of 5 µl of $10^6$ spores/ml for each strain on 30 ml of medium. Each treatment was replicated four times. The experiment was repeated twice.

Seed infections. For seed/fungal studies, two cultivars (SunRunner and Flo-Runner) of peanut (*Arachis hypogaea*) and one (Northup King N33-P3) of non-fungicide treatment maize (*Zea mays* L.) were used. All the steps were aseptically performed as described by Kale et al. Briefly, mature peanuts (20 peanut cotyledons) and maize (10 seeds) were surface sterilized and inoculated with suspensions of $10^5$ spores/ml of each respective strain, as well as with a water control (mock inoculation). Seeds were placed in 50-ml Falcon tubes containing either sterile water or the spore suspensions and shaken for 30 min in a rotary shaker at 50 rpm, after which they were placed in a high-humidity chamber. Peanut cotyledons were incubated for 3 days for peanut cultivar SunRunner or 5 days for cultivar FloRunnner at 29° C. under dark conditions, and maize kernels for 3 days. All seed experiments were repeated three times.

Histological study. Infected and control peanut cotyledons of cultivar Sun-Runner were collected after 3 days of inoculation and sliced with a razor blade into 2-cm pieces which were immersed in ice-cold fixative FAA (3.7% formaldehyde, 5% acetic acid, 47.5% ethanol in water) in vials with vacuum pressure for 30 min. Tissues were then removed, incubated with fresh FAA overnight, dehydrated through a tert-butanol series following the method of Cseke et al., and embedded in paraffin (Paraplast Plus). Paraffin blocks were sectioned in 10-µm slices, and serial sections were placed on glass slides and incubated at 37° C. at least overnight, until tissues adhered to the slides. Dewaxing of tissues and staining with Gomori methenamine-silver were performed in the University of Wisconsin—Madison School of Veterinary Medicine histology services laboratory. For lipid staining in peanut tissues, Nile red was applied to tissues following the method of Tsitsigiannis et al. A tetramethyl rhodamine 5-isothiocyanate filter in a fluorescent microscope (Olympus BX-60 with 546-nm excitation and 585-nm emission filters) was used to observe Nile red-stained tissues.

Aflatoxin extraction from medium. Eight-milliliter amounts of 1.6% GMM-2% sorbitol agar were overlaid with 3-ml amounts of 0.7% GMM agar plus 2% sorbitol agar containing $10^2$, $10^4$, and $10^6$ spores/plate of each fungal strain. Cultures were grown for 3 days at 29° C. under dark or light conditions. Three 1.5-cm plugs from each plate were homogenized in 3 ml of 0.01% Tween 80 (vol/vol) water and vortexed vigorously for 1 min. One milliliter of chloroform was added, and the sample vortexed and incubated at room temperature for 30 min. The mixture was vortexed again and then centrifuged for 15 min. The lower layer was collected, allowed to dry for 3 days, and then resuspended in 100 µl of chloroform, and 40 µl of the suspension was spotted onto TLC plates (Whatman, Maidstone, England) using a chloroform/acetone (95:5, vol/vol) solvent system. Each treatment was repeated three times.

Aflatoxin extraction from seed. Peanut cotyledons and maize kernels inoculated as described above were collected in 50-ml Falcon tubes with the addition of 5 ml of 0.01% Tween 80 and vortexed vigorously for 1 min. One milliliter was removed from each sample for conidium counting prior to aflatoxin extraction. Five milliliters of acetone was then added to the samples, followed by shaking for 10 min in a rotary shaker at 150 rpm. Samples were allowed to stand for 5 min at room temperature, and then 5 ml of chloroform was added to each sample, followed by shaking for 10 min at 150 rpm. Samples were allowed to stand for an additional 10 min at room temperature, vortexed briefly, and centrifuged for 15 min at 2,000 rpm to collect the organic lower phase. This phase was placed in a new tube and then dried completely for 3 days. Five milliliters of 0.1 M NaCl methanol/water (55:45) and 2.5 ml of hexane were added to each tube, and the mixture vortexed vigorously at high speed for 1 min. Samples were centrifuged at 2,000 rpm for 5 min. The hexane layer was collected, the remaining aqueous phase was washed with 2.5 ml of hexane, and then the collection process repeated as described above. The hexane extracts were combined, allowed to dry, and then resuspended in 500 µl of chloroform, and 10 µl of each extract was separated on a silica gel TLC plate using the chloroform/acetone (95:5 vol/vol) solvent system. Each treatment was repeated three times.

Statistical analysis. Statistical differences were analyzed using the JMP software package, version 3.2.6 (SAS Institute, Inc., Cary, N.C.). Multiple comparisons of results for all strains were calculated for growth diameter, lipase activity, and sporulation on seed. To assess the density-dependent development of each strain, sclerotial and conidial numbers were compared at three population levels. Statistically significant mean values, indicated with different letters in the figures, are significant at $P<0.05$.

Results. Creation of veA and laeA mutant strains in *A. flavus*. This study required creating near-isogenic strains varying in the number of laeA and veA alleles in the same *A. flavus* isolate. As ΔlaeA and MC strains of the genome-sequenced strain *A. flavus* 3357 already existed, the first goal was to obtain near-isogenic strains of *A. flavus* 3357 with loss of or overexpression of veA.

Figure 13:
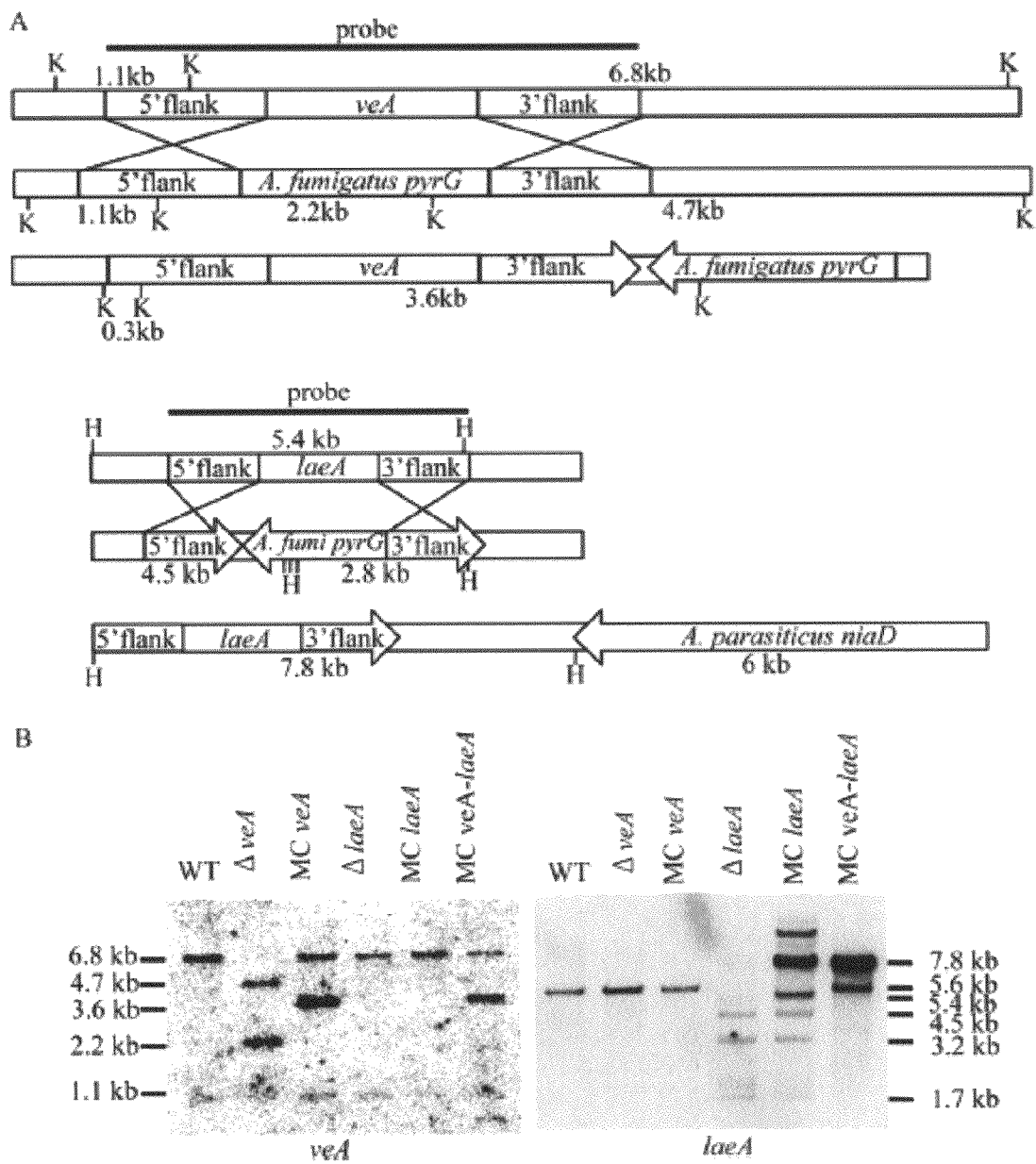
FIG. 13. Deletion, MCveA, and MClaeA mutants of *A. flavus*. (A) Diagram of the strategy of replacement of *A. flavus* NRRL 3357.5 veA with *A. fumigatus* AF293 wild-type pyrG gene shows the restriction enzyme digestion sites of KpnI for Southern analysis with veA probe. To confirm gene replacement or MC transformants using Southern analysis, at least two restriction enzymes for each probe were utilized, KpnI (K) and SapI (data not shown) for veA and HindIII (H) and BamHI (data not shown) for laeA. *A. fumi, A. fumigatus*. (B) Southern analysis. The KpnI digest shows 6.8-kb and 1.1-kb veA fragments in the wild type and 4.7-kb, 2.2-kb, and 1.1-kb fragments in the ΔveA strain. The MCveA strain shows both wild-type 6.8-kb and 1.1-kb fragments, as well as 3.6-kb and 0.3-kb (not shown) fragments. The laeA probe presented a 5.6-kb fragment in the wild type; 4.5-kb, 3.2-kb, and 1.7-kb fragments in the ΔlaeA strain; and several extra bands in the MClaeA strain. The laeA mutants have been described before, in reference 21. WT, wild type.

The sequence of the *A. flavus* 3357 veA ortholog was obtained by designing primers from the *A. flavus* ATCC MYA384 veA gene (GenBank DQ296645, SEQ ID NO: 140). The sequences of the two genes were found to be 99% identical. All primers and probes in this study were designed from this sequence (Table 6). FIG. 13A shows the strategy of replacement of veA with *A. fumigatus* pyrG. Transformants were first screened for loss of production of sclerotia on GMM plus 2% sorbitol medium, a phenotype associated with the *A. flavus* ATCC MYA384 ΔveA mutant. Several asclerotial *A. flavus* 3357 transformants were identified and their DNA extracted and analyzed by PCR and Southern analysis. Seventeen out of 100 transformants were found to contain the 4.6-kb and 4.3-kb fragments expected of KpnI (FIG. 13B) and SapI (data not shown) digests, respectively, as expected for a veA replacement with *A. fumigatus* pyrG. One of these strains, TSA 1.54, was chosen for further studies (FIG. 13B). A strain with at least two copies of veA was obtained by transforming NRRL 3357.5 with plasmid pSA3.13. Several strains were obtained, as determined by Southern analysis, and one, the MCveA strain TSA 2.46, was chosen for further studies (FIG. 13B). Next, a strain with at least two copies of both veA and laeA was obtained by transforming NRRL 3357.5 with plasmids pSA3.13 and pLRM11.1. One of these transformants, the MCveA-laeA strain TSA2.8, was chosen for further studies (FIG. 13B).

Figure 14:
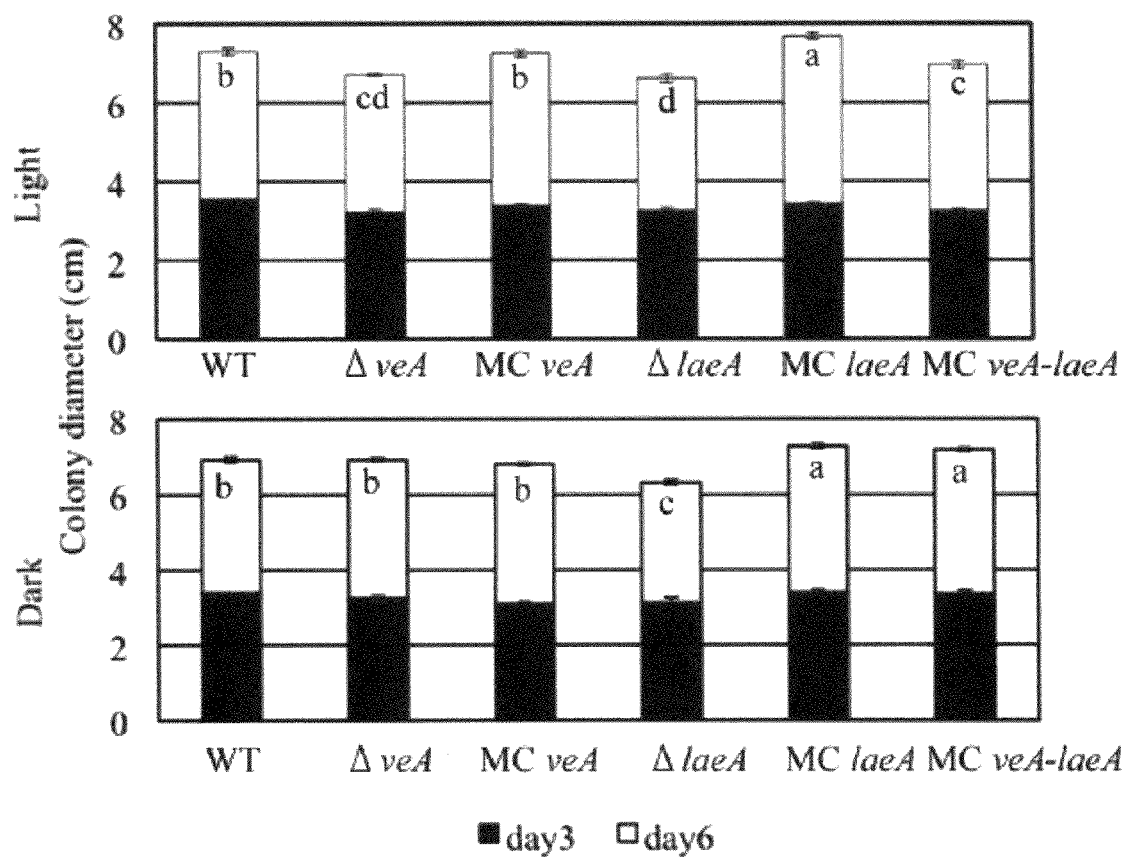
FIG. 14. Colony diameters of veA and laeA mutants of *A. flavus*. A 5-µl amount of a suspension of $10^6$ spores/ml of each strain was point inoculated on 30 ml of 1.6% GMM. Cultures were grown at 29° C. under continuous dark or light conditions, and growth diameters measured at 3 and 6 days after inoculation. Letters indicate differences between strains that were statistically significant ($P<0.05$) according to the Tukey-Kramer multiple comparison test. Error bars show the standard deviations of the results of four replications. Strains were grown in both light and dark conditions. WT, wild type.
Figure 15:
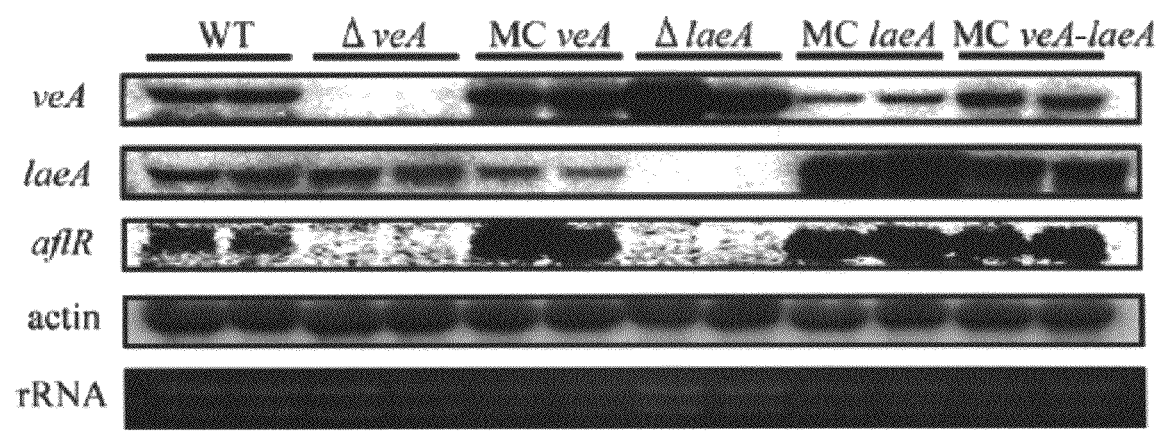
FIG. 15. Gene expression levels of veA and laeA in *A. flavus* mutants. Each strain was grown in liquid GMM culture with shaking (250 rpm at 29° C.) under dark conditions. Total RNA was extracted from two replicates at 48 hrs after inoculation. Northern blots were probed with internal or ORF fragments of each gene (Table 2). rRNA and actin were the loading and expression controls. WT, wild type.

The strains with the six genotypes (the wild type and five mutants) exhibited clear differences in development and morphology, as described below, and additionally, the ΔlaeA strain showed a statistically significant inhibition in growth diameter compared to the growth of most other strains under both light and dark conditions. Conversely, the MClaeA strain's growth diameter was greater than the growth diameters of most other strains in both light and dark regimes (FIG. 14).

veA and laeA affect each other's transcription. Kale et al. recently found that laeA expression negatively affects transcription of veA in *A. flavus*; this result was replicated in our work (FIG. 15). We also found evidence for veA regulation of laeA expression. Although Northern analysis revealed that the ΔveA strain did not show an increase of laeA expression, the MCveA strain had decreased laeA expression compared to that of the wild type. The MCveA-laeA strain showed relatively high levels of expression of both veA and laeA but not as high as the individual MC strains. We also examined the expression of the aflatoxin-specific transcription factor aflR in all strains. As expected and as previously described, there was no aflR expression in ΔveA and ΔlaeA strains. Similarly to the MClaeA strain, both the MCveA and MCveA-laeA strain showed higher levels of aflR expression than the wild type with this treatment.

Conidial and sclerotial density-dependent production is affected by VeA and LaeA. A recent study has shown that conidial and sclerotial production is density dependent in *A. flavus*, for which low cell densities resulted in high sclerotial formation and high cell densities in low sclerotial formation, with an inverse effect on conidial production. This quorum-like signaling system regulating the sclerotial-to-conidial shift was impaired in oxylipin-generating oxygenase mutants. Because VeA has been shown to be important in oxylipin signaling responses and forms a complex with LaeA in the nucleus, we now show that changes in veA and laeA expression could affect the density-dependent sclerotial-to-conidial shift.

Figure 16:
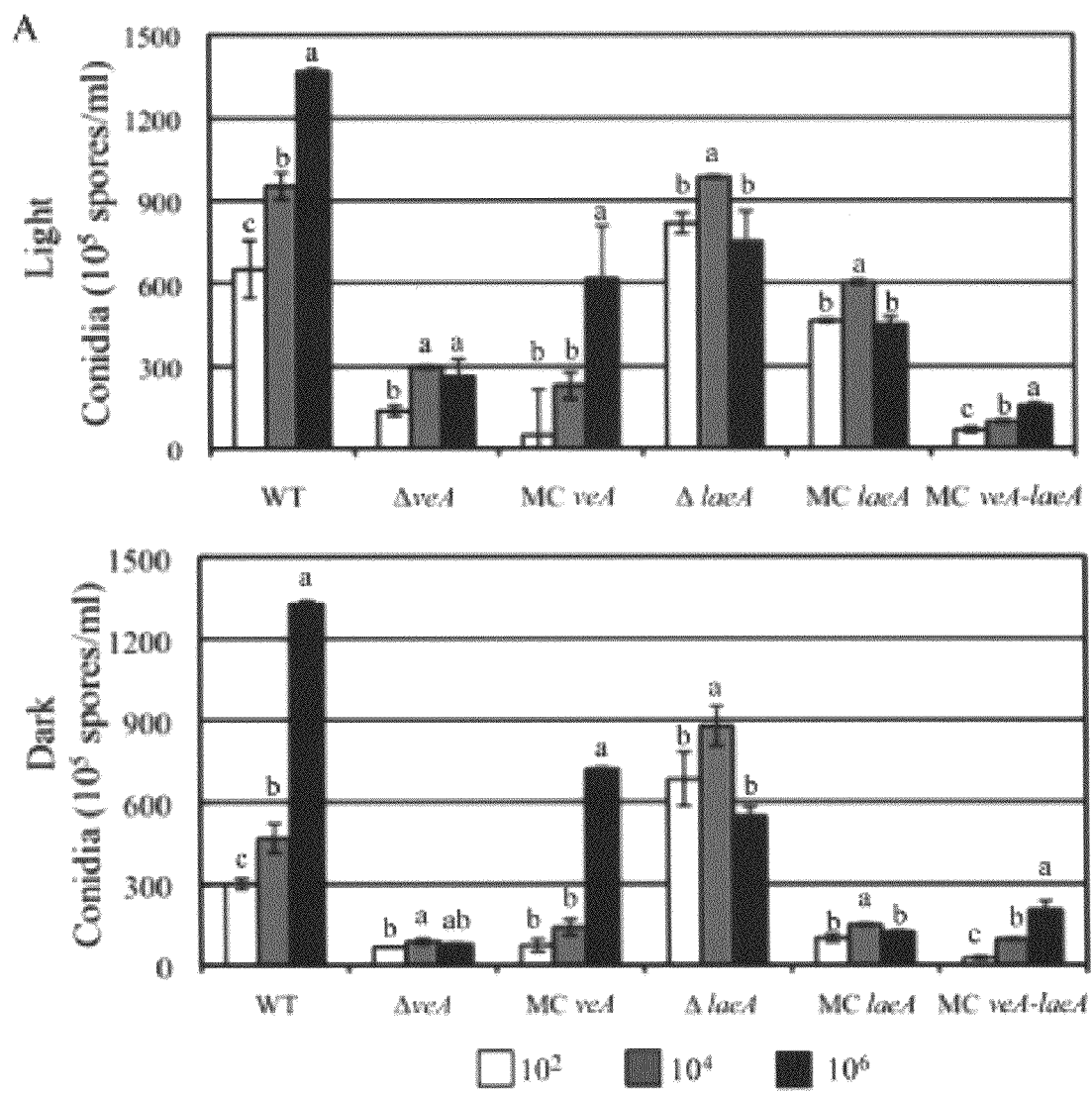
FIG. 16. Effects of veA and laeA allele numbers on density-dependent conidial and sclerotial production in *A. flavus*. Each strain was grown from $10^2$, $10^4$, and $10^6$ spores/plate as described in Materials and Methods. (A) Conidial counts. (B) Sclerotial weight. Letters indicate statistically significant differences ($P<0.05$) for each strain at different population levels according to the Tukey-Kramer multiple comparison test. Error bars show standard deviations of the results of four replications. WT, wild type.
Figure 16:
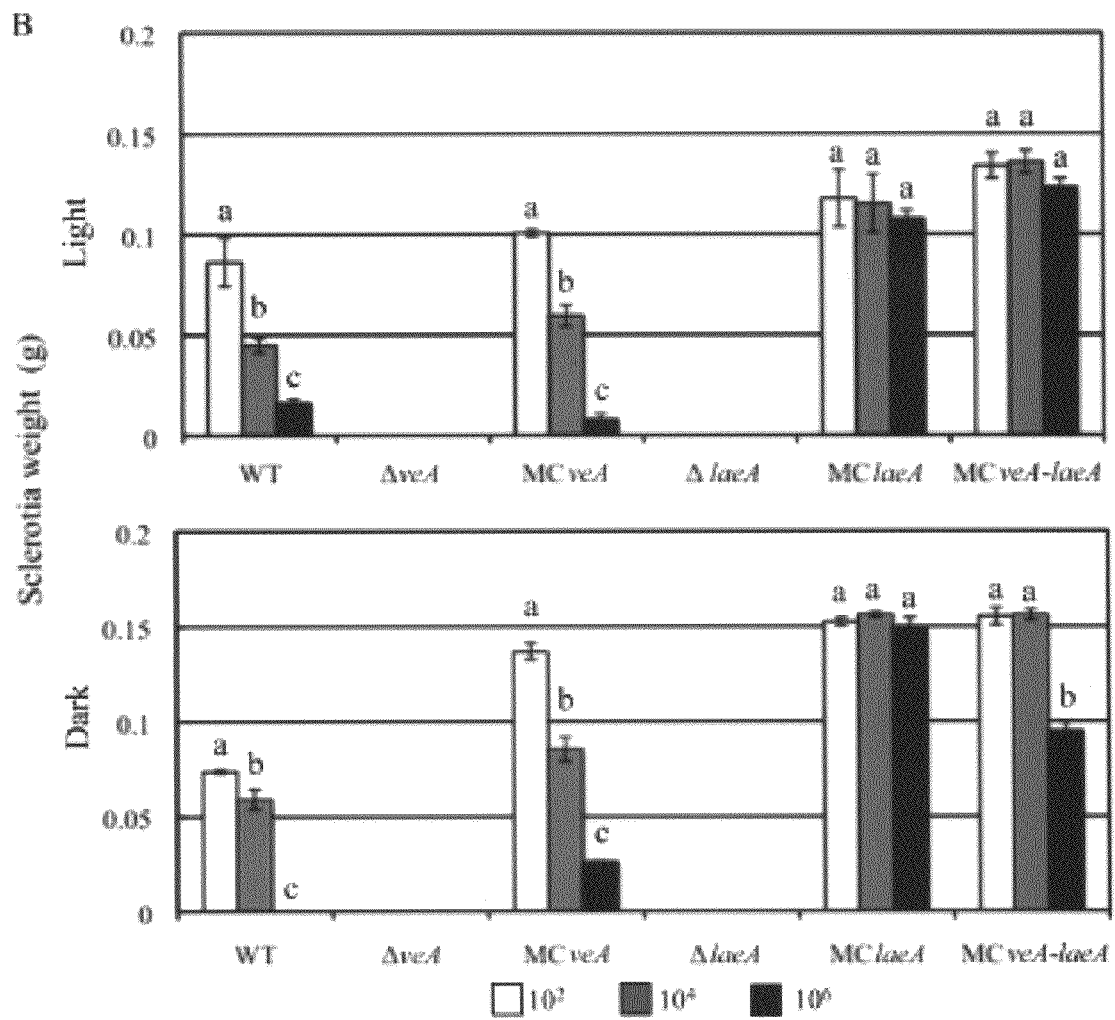

The relative abilities of the wild type and the veA and laeA mutants to form sclerotia and conidia were determined by inoculating $10^2$, $10^4$, and $10^6$ conidia onto GMM plus 2% sorbitol plates which were placed in constant dark at 29° C. for 3 (conidia) and 7 (sclerotia) days. Similar to prior results, sclerotial production diminished and conidial production increased in the wild type with increasing cell population levels (FIGS. 16A and B). The veA and laeA null mutants were incapable of producing sclerotia at any population level and yielded relatively constant levels of conidial production regardless of population levels (FIGS. 16A and B).

However, clear differences between effects of loss of or overexpression (MC) of veA compared to the results for cognate laeA mutants emerged in both conidial and sclerotial development. Previous studies have suggested a "balance" in sclerotial and conidial production, i.e., when sclerotial production is low, conidial is high and vice versa. This appeared to hold true for the ΔlaeA strain (no sclerotial production at any cell density and high conidial counts at all densities) but not the ΔveA strain, for which conidial counts were very low at all population levels (FIG. 16A) despite the lack of sclerotial production (FIG. 16B). The MC mutants also showed clear differences in their density-dependent responses. The MCveA strain still exhibited a density-dependent response in sclerotial production with declining numbers in both light and dark regimes at high population levels (FIG. 16B). This was in contrast to the MClaeA strain, which maintained constant sclerotial numbers at all population levels (FIG. 16B). The MCveA-laeA double mutant exhibited an intermediate response. The trend to increased conidial numbers at high population levels was maintained in the MCveA and MCveA-laeA strains but not in the MClaeA strain (FIG. 16A). These results are summarized in Table 7.

TABLE 7

Summary of density-dependnent phenomena in *A. flavus* mutants, morphological differentiations under indicated conditions.

| Mutation | Light-Conidia | Light-Sclerotia | Dark-Conidia | Dark-Sclerotia |
|---|---|---|---|---|
| None (WT) | + | + | + | + |
| ΔveA | ± | − | ± | − |
| ΔlaeA | − | − | − | − |
| MCveA | ± | + | ± | + |
| MClaeA | − | − | − | − |
| MCveA-laeA | + | ± | + | ± |

Figure 17:
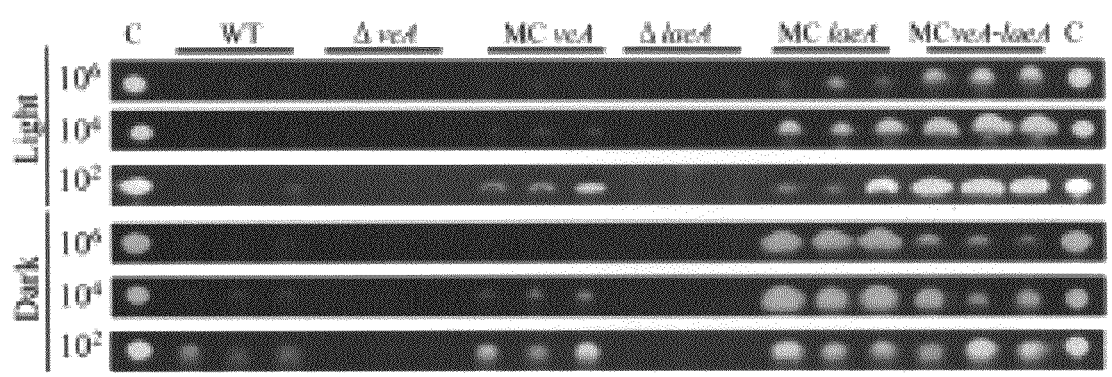
FIG. 17. Aflatoxin production of veA and laeA mutants. Aflatoxin from each strain was assessed at three different spore inoculation levels. The experiment was replicated three times, as shown. C, aflatoxin B1 control; WT, wild type.

+ indicates the presence of density-dependent development.
± indicates an intermediate response.
− indicates the absence of density-dependent development Density-dependent production of aflatoxin is controlled by LaeA. We also examined the strains for possible effects of laeA and veA expression on aflatoxin production at all cell densities, as aflatoxin production in the wild type is highest at low population levels. Regardless of cell densities, the ΔveA and ΔlaeA strains never produced observable aflatoxin under the growth conditions used here, whereas all the MC strains produced aflatoxin in all treatments (FIG. 17). The MCveA strain also showed a density-dependent decrease of aflatoxin with increasing cell population, similar to the wild type, whereas the MClaeA strain did not, and the double mutant showed an intermediate result. Aflatoxin production correlated with sclerotial production.

VeA and LaeA are important factors for seed colonization. Recently, Kale et al. reported that laeA mutants were aberrant in host colonization and aflatoxin production on both peanut and maize seed, but there are no reports for the role of VeA in *A. flavus* pathogenicity. Here, we examined and contrasted colonization attributes of the different veA and laeA mutants on two peanut cultivars and one maize hybrid.

Figure 18:
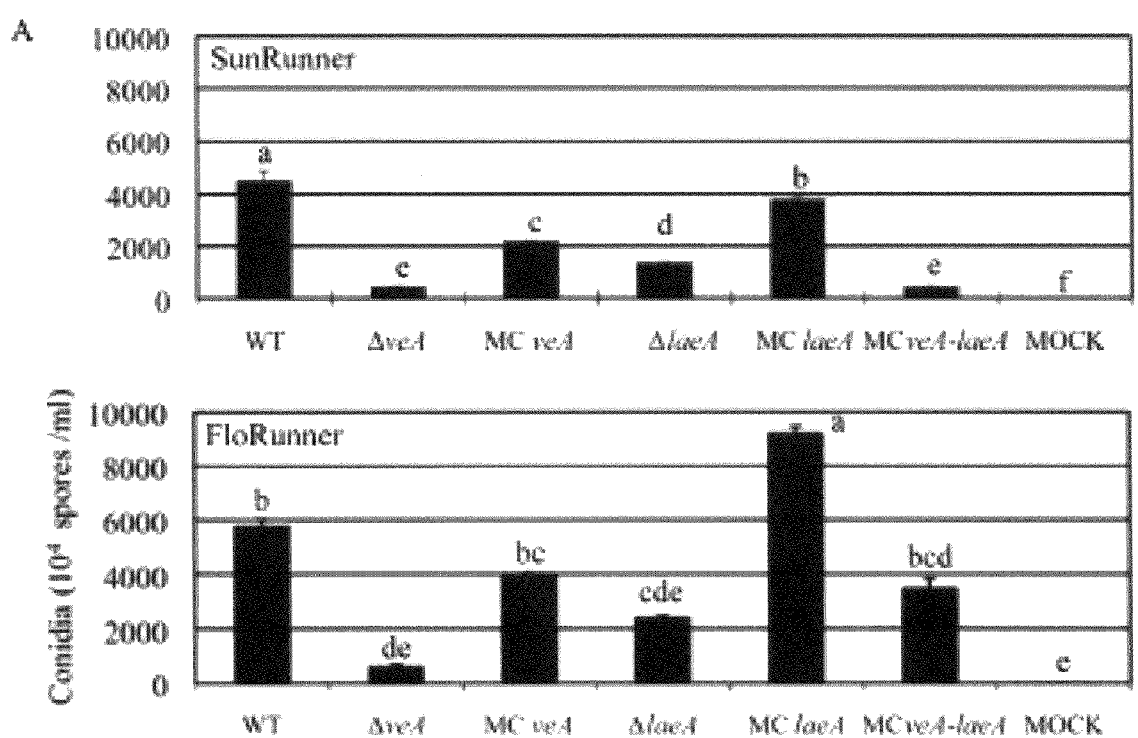
FIG. 18. Conidium production and aflatoxin production on peanut and maize seeds. Seeds of two peanut cultivars and one maize line were inoculated with $10^5$ spores/ml of the wild type and the veA and laeA mutants and incubated for either 3 days (peanut cultivar SunRunnner and maize kernels) or 5 days (peanut cultivar FloRunner) after inoculation at 29° C. under dark conditions. (A) For conidium counting, 1-ml amounts of homogenized suspensions of five peanut cotyledons or maize kernels of inoculated seeds were diluted to 1× and conidia counted. Letters indicate statistically significant differences ($P<0.05$) of different strains, according to Tukey-Kramer multiple comparison test. Error bars show the standard deviations of the results of three replications. (B) Aflatoxin was extracted from inoculated peanut cotyledons and maize kernels and resuspended in 500 µl of chloroform, and 10 µl of each extract was spotted on a TLC plate and separated with chloroform/acetone (95:5, vol/vol). C, aflatoxin B1 control; WT, wild type; MOCK, control inoculated with water.
Figure 18:
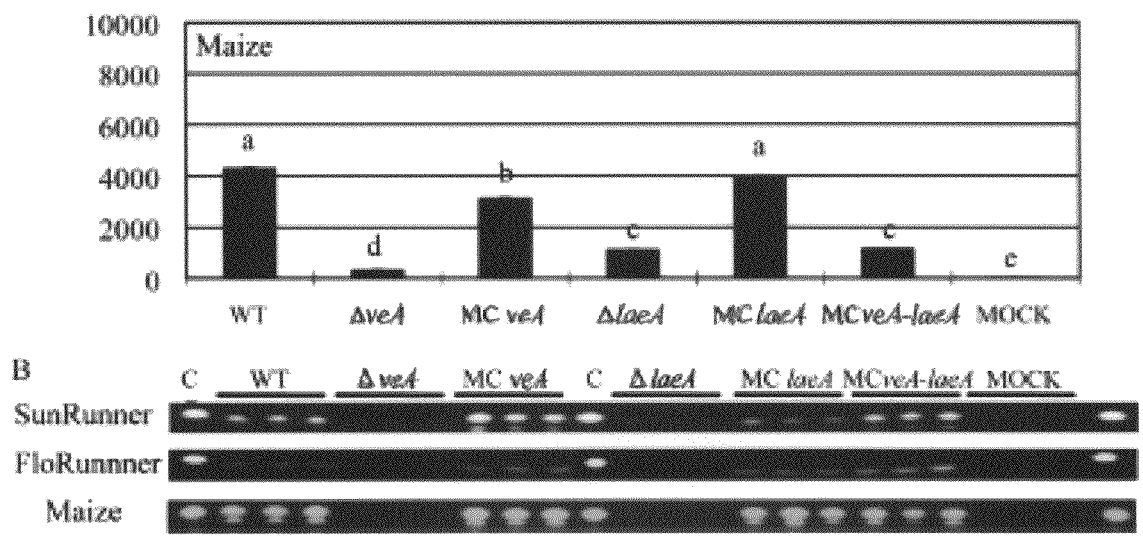

Each fungal strain maintained similar growth patterns regardless of the host seed. FIG. 18A shows that both null mutants produced fewer conidia than the wild type during growth on seeds, with the ΔveA strain developing significantly fewer conidia than the ΔlaeA strain. Visually, the ΔveA strain was most crippled in its ability to grow on any seed (data not shown). The MCveA and MCveA-laeA strains also produced fewer conidia than the wild type; however, the MClaeA strain was similar to the wild type in conidial production, depending on the host seed, as reported earlier. The MC strains also formed sclerotia on the seeds (data not shown).

The colonized seeds were next examined for aflatoxin contamination. All MC strains and the wild type produced aflatoxin in all hosts, in contrast to the lack of aflatoxin production by both the ΔveA and ΔlaeA strain (FIG. 18B). The considerably higher aflatoxin production by some MC mutants in vitro (FIG. 17), however, was not replicated in growth on seed under the conditions in this study.

Figure 19:
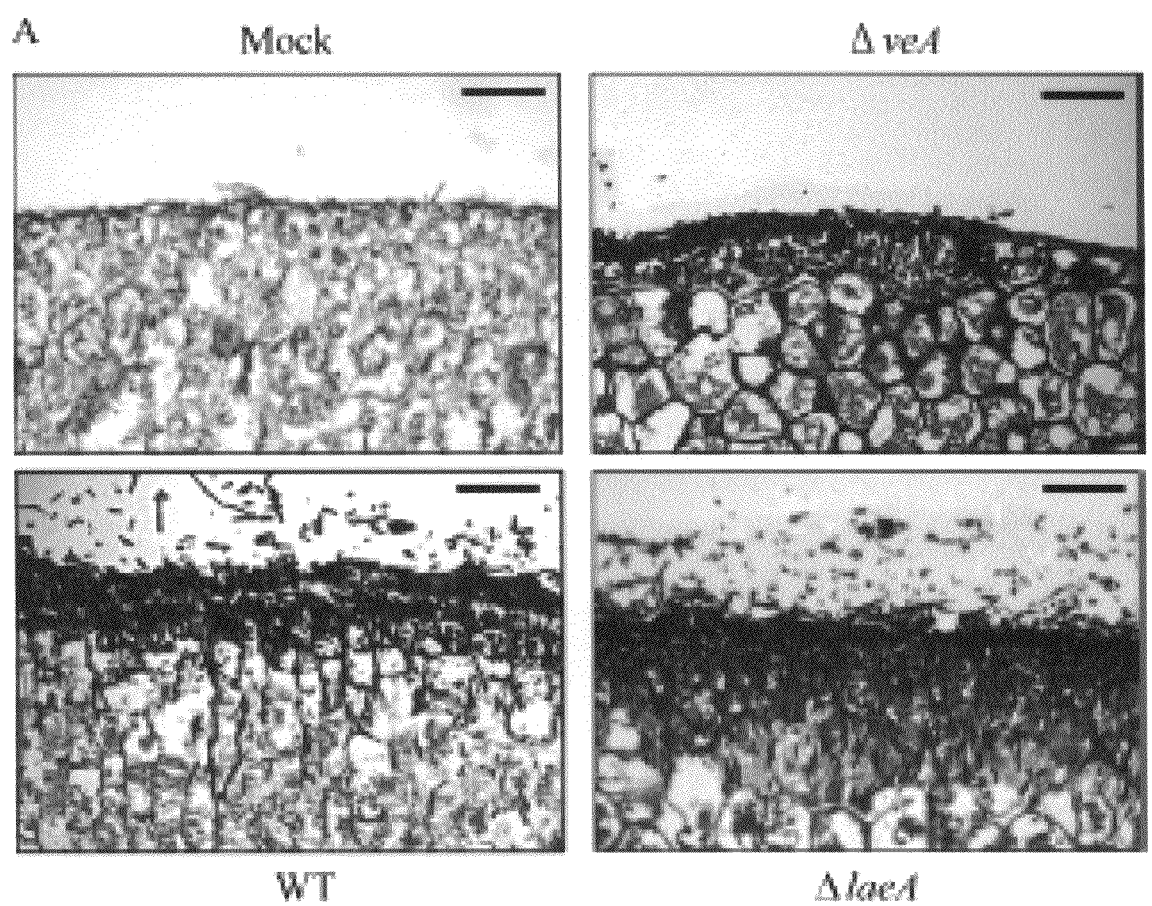
FIG. 19. Histological examination reveals differences in seed ingress and lipid utilization of ΔveA and ΔlaeA strains compared to these functions in the wild type. (A) Tissues were stained with Gomori methenamine-silver for detection of fungal hyphae. (B) Tissues were stained with Nile red for lipid body detection in seeds. To observe tissues, a bright-field microscope was used for Gomori stain and a tetramethyl rhodamine 5-isothiocyanate filter in a fluorescent microscope was used for Nile red. Seeds infected with the wild-type fungus show diminishment of lipid bodies near the surface (white line) of the seed. Scale bars=100 µm. WT, wild type; Mock, control inoculated with water.
Figure 19:
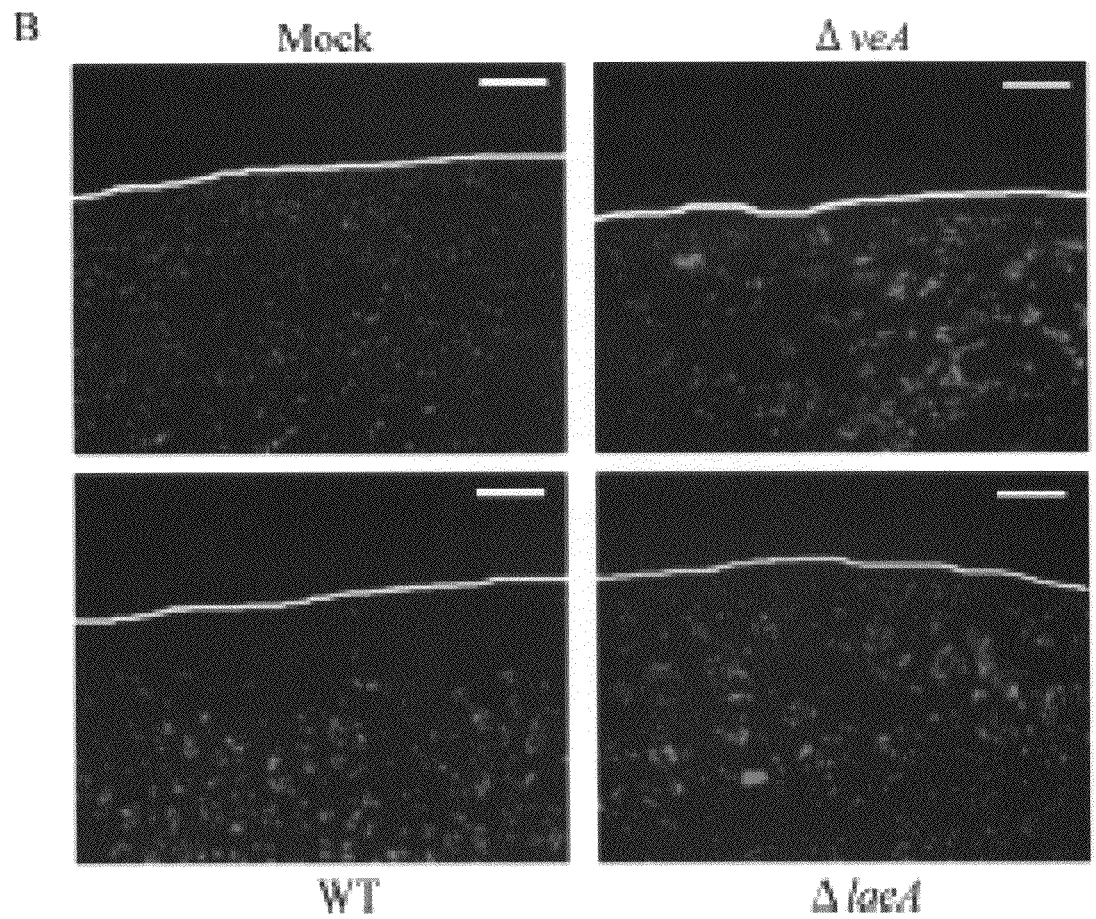

To further investigate the ability of the strains to colonize seed, histological studies were performed. We were specifically interested in assaying for maceration effects and reasoned that this could be partially measured by host cell lipid utilization. The staining techniques did not show any obvious difference in host penetration by MC strains compared to that of the wild type (data not shown). However, the two null mutants exhibited different host invasion patterns. The results in FIGS. 19A and B show that wild-type hyphae penetrated several layers of host epidermal and mesophyll cells, with accompanying dissolution of host lipid reserves. Although the ΔlaeA strain also penetrated the host cells intracellularly, host lipid reserves were largely intact and the cell integrity appeared less damaged (FIGS. 19A and B). In contrast, hyphae of the ΔveA strain grew intercellularly in epidermal cells and did not appear to penetrate peanut cells as well as hyphae of other strains (FIG. 19A). This mutant, like the ΔlaeA mutant, was also less able to degrade host cell lipid reserves than the wild type (FIG. 19B). However, an in vitro assay for general lipase activity revealed no significant difference between these strains (data not shown).

Figure 20:
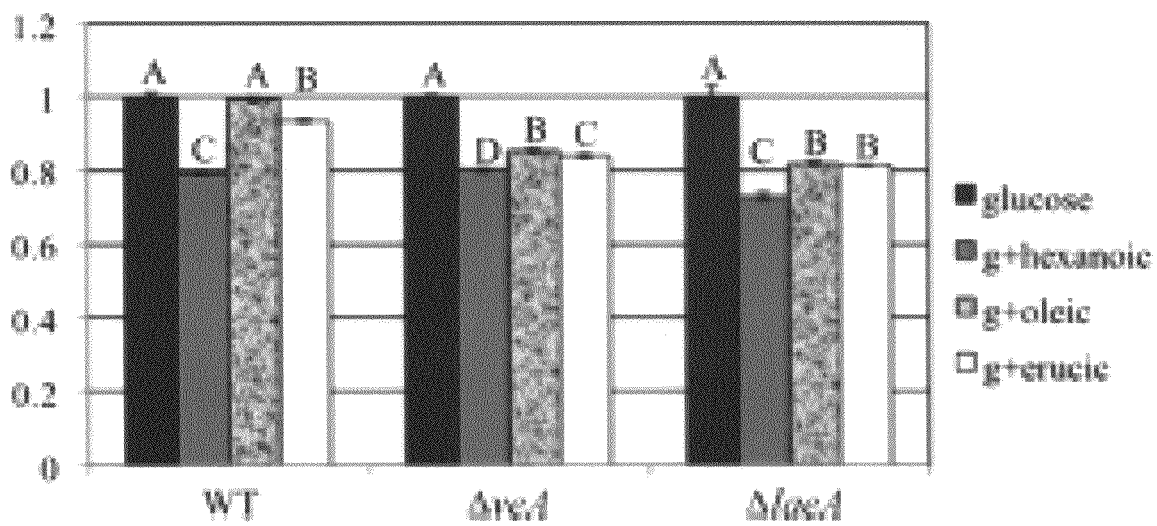
FIG. 20. Loss of veA and laeA sensitizes the fungus to oleic acid. Inhibition of colony diameters of ΔveA and ΔlaeA mutants but not the wild type is observed when GMM is supplemented with 6 mM oleic acid at 3 (data not shown) and 6 days after inoculation. Letters indicate statistically significant differences ($P<0.05$) at 6 days after inoculation with different strains, according to Tukey-Kramer multiple comparison test. Error bars show the standard deviations of the results of four replications. WT, wild type; g, glucose; hexanoic, hexanoic acid; oleic, oleic acid; erucic, erucic acid.

The wild type and the ΔlaeA and ΔveA strains were then grown on media amended with different fatty acids either as sole carbon source or supplemented with glucose to determine if there might be any gross difference in the ability to utilize or be inhibited by short-, medium-, or long-chain fatty acids. The results did not support any critical difference between the wild type and the two mutants when grown on a fatty acid as the sole carbon source, but the two mutants showed significant inhibition of growth compared to that of the wild type when cultured on GMM amended with oleic acid (FIG. 20). This experiment was repeated twice with similar results (data not shown).

Discussion. In this study, we characterized the function and crossregulation of VeA and LaeA in *A. flavus* development and pathogenesis. The results, while confirming that VeA and LaeA share functions in regulating aflatoxin and sclerotial production, also demonstrate distinct roles of VeA and LaeA in terms of vegetative growth, conidiation, density-dependent responses, and pattern of colonization of host tissues.

A requirement for LaeA in density-dependent sensing. Quorum-sensing systems in bacteria contribute to the production of virulence factors and biofilm formation in interactions between bacteria and host. In fungi, a quorum-sensing system governing morphological shifts and virulence has been uncovered in the human pathogen *Candida albicans*. Recently, oxylipin-deficient lipoxygenase and dioxygenase mutants have been found to affect a newly discovered quorum-sensing-like, density-dependent sclerotial-to-conidial morphology shift in *A. flavus*. Because oxylipin signaling is dependent on VeA function and VeA is part of a nuclear complex with LaeA, we asked if VeA or LaeA mutants could be affected in this quorum-like morphology shift in *A. flavus*. Both null mutants were blocked in sclerotial formation regardless of cell population, and perhaps due to an inability to produce sclerotia, conidial production was relatively stable for each mutant at all three population levels, although it was much higher in the ΔlaeA strain.

The MC strains showed clear differences in density-dependent development in that an extra copy of LaeA but not VeA abolished this quorum-like phenomenon (FIGS. 16A and B). To date, there are no chemical data identifying molecules regulating the sclerotial-to-conidial switch in *A. flavus*, although oxylipins are hypothesized to fulfill this function at least in part. Quorum-sensing molecules for *Candida albicans* (farnesol and tyrosol) and *Saccharomyces cerevisiae* (phenylethanol and tryptophol) are aromatic alcohols and control the morphological switch from the yeast to filamentous growth in these fungi.

Interestingly, the yeast-to-filamentous growth switch in the fungus *Ceratocystis ulmi* is attenuated by lipoxygenase inhibitors and may implicate oxylipins in quorum sensing in this tree pathogen. We speculate that *A. flavus* MClaeA mutants are aberrant in oxylipin production and/or sensing but that this can be remediated to some degree when VeA levels also increase, as demonstrated by the intermediate density-dependent phenotype of the MCveA-laeA strain. The effects of gene loss and gain on density-dependent development are summarized in Table 7.

VeA and LaeA feedback regulation. Both veA and laeA have been reported to be global regulators of secondary metabolites in *A. flavus*, as well as in other aspergilli. Here, the results indicate that the MCveA and MClaeA strains—particularly the MClaeA strain—produce more aflatoxin and sclerotia than the wild type. The MCveA-laeA double mutant did not show increased toxin production compared to that of the single mutants or an additive effect on sclerotial production. Prior work indicated that LaeA negatively regulated veA expression, and here, we show evidence for VeA regulation of LaeA (FIG. 15), as was described for *A. nidulans*. These results support a mechanism of mutual repression of veA and laeA expression and may explain, in part, a dampening of the expression of both genes in the MCveA-laeA strain compared to the expression of the single genes in the MCveA and MClaeA strains which, in turn, may affect aflatoxin and sclerotial output in the double mutant.

Requirement for VeA and LaeA in host cell penetration and degradation. Host lipid reserves are depleted during seed colonization by *Aspergillus*, with lipase and esterase activities implicated in seed pathogenesis. Both null mutants were impaired in seed colonization, where neither strain could degrade lipid reserves despite hyphal penetration of at least some layers of the host seeds (FIGS. 19A and B). The crippled ability of both null mutants to utilize lipid reserves brings to mind several lipid biosynthesis mutants also impaired in *Aspergillus* colonization of seed, including β-oxidation mutants, odeA mutants [(delta)12-desaturase], and the oxylipin oxygenase mutants in *A. nidulans* and *A. flavus*. The inhibition of both null mutants by oleic acid (not seen in the wild type) (FIG. 20) suggests a possible toxic effect of this fatty acid on these strains which may relate to their impairment in growth on seed. It is less likely that the inhibition is associated with defects in β-oxidation, since the mutants grew equally as well as the wild type on oleic acid as a sole carbon source (data not shown), although we cannot rule out this possibility. Regardless of mechanism, the results of all of these studies together may support lipid utilization and/or signaling as an important factor in *Aspergillus* seed pathogenesis.

Interestingly, the hyphal penetration patterns of the two null mutants as revealed by Gomori staining were quite diverse, whereas hyphae of the ΔveA strain remained largely intercellular (FIG. 19A). This inability to penetrate intracellularly may indicate loss of degradative enzymes in this strain and may explain its poor production of conidia on host seed. However, we note that the strain is crippled in conidial production on medium also. The relative decrease of conidial production by the ΔlaeA strain on seed (compared to its vigorous conidial production in medium) might be attributable to a loss in lipid assimilation or the possible toxicity effects mentioned above.

Histology of the MC strains presented an invasion and lipid degradation pattern similar to that of the wild type. The relatively decreased conidial production on seed from these strains is possibly a function of their skewed sclerotial development rather than an inability to obtain nutrients from the seed.

In conclusion, this example provides additional evidence for distinct roles of LaeA and VeA in the development and pathogenesis of *A. flavus* despite the considerable overlapping of functions previously reported. The loss of both genes blocks the production of sclerotia and aflatoxin, but under our conditions, only laeA overexpression abolishes density-dependent phenomena, including a sclerotial-to-conidial shift and decreased aflatoxin production with cell population increase. The null mutants, while both were reduced in host lipid utilization, displayed distinct cell ingress abilities as reflected in patterns of hyphal penetration of host cells.

Other embodiments and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference.

It is understood that the invention is not confined to the specific reagents, formulations, reaction conditions, etc., herein illustrated and described, but embraces such modified forms thereof as come within the scope of the following claims.

REFERENCES

Adams et al., Microbiol. Mol. Biol. Rev. 62, 35 (1998).
Bayram et al., Fungal Genet Biol 45, 127 (2008).
Bayram et al., Science 320:1504-1506 (2008).
Brakhage, FEMS Microbiol. Lett. 148, 1 (1997).
Bok et al., Eukaryot. Cell 3, 527 (2004).
Bok et al., Eukaryot. Cell 3:527-535 (2004).
Bok et al., Eukaryot. Cell 4:1574-1582 (2005).
Bok et al., Mol. Microbiol. 61, 1636 (2006).
Brodhagen et al., Mol. Microbiol. 67:378-391 (2008).
Busch et al., Mol Microbiol 49, 717 (2003).
Busch et al., Proc. Natl. Acad. Sci. U.S.A. 104, 8089 (2007).
Calvo et al., Microbiol. Mol. Biol. Rev. 66, 447 (2002).
Calvo et al., Appl. Environ. Microbiol. 65:3668-3673 (1999).
Calvo et al., Appl. Environ. Microbiol. 70:4722-4739 (2004).
Chaveroche et al., Nucleic Acids Res 28, E97 (2000).
Cho et al., The Journal of Microbiology 41, 46 (2003).
Champe et al., J. Gen. Microbiol. 133:1383-1387 (1987).
Chen et al., Proc. Natl. Acad. Sci. USA 101:5048-5052 (2004).
Chen et al., Genes Dev. 20:1150-1161 (2006).
Cseke et al., Handbook of molecular/cellular methods in biology and medicine, 2nd ed.
CRC Press, Boca Raton, Fla. (2004).
Dagenais et al., Infect. Immun. 76:3214-3220 (2008).
Diener et al., Annu. Rev. Phytopathol. 25:249-270 (1987).
Dreyer et al., Appl. Environ. Microbiol. 73, 3412 (2007).
Duran et al., Appl. Microbiol. Biotechnol. 73:1158-1168 (2007).
Duran et al., Open Mycol. J. 3:27-36 (2009).
Eng et al., J. Am. Soc. Mass 5, 976 (1994).
Etxebeste et al., Eukaryot Cell (2007).
Feinberg et al., Anal Biochem 132, 6 (1983).
Fernandez-Abalos et al., Mol Microbiol 27, 121 (1998).
Fray, Ann. Bot. 89:245-253 (2002).
Georgianna et al., 2009. Fungal Genet. Biol. 46:113-125 (2009).
Golemis, R. Brent, in Current protocols in molecular biology F. M. Ausubel et al., Eds. (Harvard Medical School, Massachusetts), vol. 3, pp. 429-454 (1996).
Gyuris et al., Cell 75, 791 (1993).
Greenspan et al., 1985. J. Cell Biol. 100:965-973.
Hanahan et al., Methods Enzymol 204, 63 (1991).
Hicks et al., in The Mycota, vol. 11, F. Kempken, Ed. (Springer, Berlin), pp. 55-69 (2002).
Hu et al., Mol. Cell 9, 789 (2002).
Hornby et al., Appl. Environ. Microbiol. 67:2982-2992 (2001).
Horowitz et al., Appl. Environ. Microbiol. 74:5674-5685 (2008).
Horowitz et al., Mol. Plant Microbe Interact., in press.
Jensen et al., Appl. Environ. Microbiol. 58:2505-2508 (1992).
Kale et al., Fungal Genet. Biol. 45:1422-1429 9 (2008).
Kato et al., Eukaryot. Cell 2:1178-1186 (2003).
Kim et al., Fungal Genet. Biol. 37:72-80 (2002).
Klich, Mol. Plant Pathol. 8:713-722 (2007).
Keller et al., Nat. Rev. Microbiol. 3, 937 (2005).
Keller et al., Appl. Environ. Microbiol. 60:1444-1460 (1994).
Kolar et al., Gene 62, 127 (1988).
Krappmann et al, Eukaryot. Cell 4, 1298 (2005).
Krappmann et al., Mol Microbiol 61, 76 (2006).
Kunkel, Proc Natl Acad Sci USA 82, 488 (1985).
Li et al., Mol. Microbiol. 62, 1418 (2006).
Link et al., Nat Biotechnol 17, 676 (1999).
Lillie, Histopathologic technique and practical histochemistry, 3rd ed. McGraw-Hill Book Company, New York, N.Y. (1965).
Maggio-Hall et al., Mol. Microbiol. 54:1173-1185 (2004).
Maggio-Hall et al., Mol. Plant Microbe Interact. 18:783-793 (2005).
Michailides et al., Plant Pathol. 56:352 (2007).
Miller et al., Mol. Cell. Biol. 5:1714-1721 (1985).
Mooney et al., Genes Dev. 4, 1473 (1990).
Muyrers et al., Genet Eng (N Y) 22, 77 (2000).
Muture et al., East Afr. Med. J. 82:275-279 (2005).
Nayak et al., Genetics 172, 1557 (2.006).
Ni et al., PLoS One 2, e970 (2007).
Perrin et al., PLoS Pathog. 3:e50 (2007).
Puig et al., Methods 24, 218 (2001).
Punt et al., Methods Enzymol 216, 447 (1992).
Purschwitz et al., Curr. Biol. 18, 255 (2008).
Pettit, Yellow mold and aflatoxin, p. 35-36. In D. M. Porter, D. H. Smith, and R.
Rodeiguez-Kabana (ed.), Compendium of peanut diseases. The American Phytopathological Society, St. Paul, Minn. (1984).
Rohila et al., Plant J. 38, 172 (2004).
Rubens, J., and K. F. Cardwell. The cost of mycotoxin management in the United States, p. 1-13. In H. K. Abbas (ed.), Aflatoxin and food safety. CRC Press, Boca Raton, Fla. (2005).
Saiki et al., Nature 324, 163(1986).
Sambrook et al., Maniatis, Molecular Cloning: A Laboratory Manual
Seiler, et al., Mol Biol Cell 17, 4080 (2006).
Shevchenko et al., Anal Chem 68, 850 (1996).
Shwab et al., Eukaryot. Cell 6, 1656 (2007).
Southern, J Mol Biol 98, 503 (1975).
Spröte et al., Arch. Microbiol. 188, 69 (2007).
Stinnett et al., Mol. Microbiol. 63, 242 (2007).
Shchepin, et al., Chem. Biol. 10:743-750 92003).
Shimizu, K. et al., Genetics 157: 591-600 (2001).
Smart et al., Phytopathology 80:1287-1294 (1990).
Szewczyk et al., Nat. Protoc. 1:3111-3120 (2006).
Thompson et al., Nucleic Acids Res 22, 4673 (1994).

Tsitsigiannis et al., Mol. Microbiol. 59:882-892 (2006).
Tsitsigiannis et al., Microbiology 151:1809-1821 (2005).
Tsitsigiannis et al., J. Biol. Chem. 279:11344-11353 (2004).
Williams, Microbiology 153:3923-3938 (2007).
Wilson et al., Microbiology 150:2881-2888 (2004).
Woloshuk et al., Appl. Environ. Microbiol. 60, 2408 (1994).
Yu et al., Fungal Genet Biol 41, 973 (2004).
Yu et al., Rev. Iberoam. Micol. 22:194-202 (2005).
Yu et al., Mycotoxin production and prevention of aflatoxin contamination in food and feed. In G. H. Goldman and S. A. Osmani (ed.), The aspergilli. CRC Press, Boca Raton, Fla. (2008).

What is claimed is:

1. A method of producing an isolated *Aspergillus* secondary metabolite comprising the steps of:
    (a) transforming an *Aspergillus* cell or organism with a nucleic acid encoding a veA polypeptide comprising SEQ ID NO:116;
    (b) culturing the transformed *Aspergillus* cell or organism under conditions conducive to production of a secondary metabolite that the *Aspergillus* cell or organism is capable of biosynthesizing; and
    (c) recovering the secondary metabolite from the cultured, transformed *Aspergillus* cell or organism in an isolated form.

2. The method of claim 1 wherein the *Aspergillus* cell or organism is *A. nidulans* or *A. flavus*.

* * * * *